(12) United States Patent
Bentzien

(10) Patent No.: US 6,514,729 B1
(45) Date of Patent: Feb. 4, 2003

(54) RECOMBINANT INTERFERON-BETA MUTEINS

(75) Inventor: Jörg Bentzien, Pasadena, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 09/569,722

(22) Filed: May 11, 2000

Related U.S. Application Data

(60) Provisional application No. 60/133,785, filed on May 12, 1999.

(51) Int. Cl.$^7$ .............................................. C12N 15/00
(52) U.S. Cl. ..................... 435/69.51; 435/442; 435/7.1; 530/351; 424/85.6
(58) Field of Search .............................. 435/69.51, 7.1, 435/442; 530/351; 424/85.6

(56) References Cited

U.S. PATENT DOCUMENTS

| | | | |
|---|---|---|---|
| 4,518,584 A | 5/1985 | Mark et al. | 424/85 |
| 4,588,585 A | 5/1986 | Mark et al. | 424/85 |
| 4,737,462 A | 4/1988 | Mark et al. | 435/253 |
| 4,738,844 A | 4/1988 | Bell et al. | 424/85 |
| 4,738,845 A | 4/1988 | Bell et al. | 424/85 |
| 4,753,795 A | 6/1988 | Bell et al. | 424/85 |
| 4,769,233 A | 9/1988 | Bell et al. | 424/85 |
| 4,793,995 A | 12/1988 | Bell et al. | 424/85.6 |
| 4,885,166 A | * 12/1989 | Meyer et al. | 424/85.7 |
| 4,914,033 A | 4/1990 | Bell et al. | 435/252.3 |
| 4,959,314 A | 9/1990 | Mark et al. | 435/69.1 |
| 5,183,746 A | 2/1993 | Shaked et al. | 435/69.51 |
| 5,376,567 A | 12/1994 | McCormick et al. | 435/320.1 |
| 5,545,723 A | 8/1996 | Goelz et al. | 424/85.6 |
| 5,730,969 A | 3/1998 | Hora et al. | 424/85.1 |
| 5,814,485 A | 9/1998 | Dorin et al. | 435/69.51 |
| 5,869,603 A | 2/1999 | Hoeprich, Jr. | 530/328 |

FOREIGN PATENT DOCUMENTS

| | | |
|---|---|---|
| WO | 98/47089 | 10/1998 |
| WO | 98/48018 | 10/1998 |

OTHER PUBLICATIONS

Shepard et al. A single amino acid change in IFN–b1 abolishes its antiviral activity. 1981. Nature, 294:563–565.*

Runkel et al. Systematic mutational mapping of sites on human IFN–b–1a that are important for receptor binding and functional activity. 2000. Biochemistry, 39:2538–51.*

Lengyel, "Biochemistry of Interferons and Their Actions", *Annu. Rev. Biochem.* 51:251–82 (1982).

Gresser and Tovey, "Antitumor Effects of Interferon", *Biochim. Biophys. Acta* 516(2):231–47 (1978).

Gresser et al., "Effect of Interferon Treatment of L1210 Cells in vitro on Tumour and Colony Formation", *Nature New Biol.* 231(18):20–1 (1971).

Dolei et al., "Interferon Effects on Friend Leukaemia Cells. I. Expression of Virus and Erythroid markers in Untreated and Dimethyl Supphoxide–treated Cells", *J. Gen. Virol.* 46(1):227–36 (1980).

Gresser, "On the Varied Biologic Effects of Interferon", *Cell Immunol* 34(2):406–15 (1977).

Stewart, "Interferon Nomenclature Recommendations", *J. Infect. Dis.* 142(4):643 (1980).

Knight, "Interferon: Purification and initial characterization from human diploid cells", *Proc. Natl. Acad. Sci. U.S.A.* 73(2):520–523 (1976).

Li et al., "Cooperative Binding of Stat1–2 heterodimers and ISGF3 to tandem DNA elements," *Biochemie* 80(8–9):703–10 (1998).

Nadeau et al., "The Proximal Tyrosines of the Cytoplasmic Domain of the β Chain of the Type I Interferon Receptor Are Essential for Signal Transducer and Activator of Transcription (Stat) 2 Activation", *J. Biol. Chem.* 274(7):4045–52 (1999).

Lewerenz et al., "Shared Receptor Components but Distinct Complexes for α and β Interferons", *J. Mol. Biol.* 282(3):585–99 (1998).

Clemens, *Cytokines*, BIOS Scientific Publishers Limited, Oxford, UK, 1991.

De Maeyer et al., "The Interferon Gene Family" in *Interferons and Other Regulatory Cytokines*, Chap. 2, pp. 5–38, Wiley, New York, 1988.

Tanaguchi et al., "The nucleotide sequence of human fibroblast interferon cDNA", *Gene* 10(1):11–15 (1980).

Houghton et al., "The complete amino acid sequence of human fibroblast interferon as deduced using synthetic oligodeoxyribonucleotide primers of reverse transcriptase", *Nucleic Acids Res.* 8(13):2885–94 (1980).

Ohno and Taniguchi, "Inducer–responsive expression of the cloned human interferon $β_1$ gene introduced into cultured mouse cells", *Nucleic Acids Res.* 10(3):967–77 (1982).

Smith et al., "Production of Human Beta Interferon in Insect Cells Infected with a Baculovirus Expression Vector", *Mol. Cell. Biol.* 3(12):2156–65 (1983).

Demolder et al., "Human interferon–β, expressed in *Saccharomyces cerevisiae*, is predominantly directed to the vacuoles. Influence of modified co–expression of secretion factors and chaperone", *J. Biotechnol.* 32(2):179–89 (1994).

Desmyter et al., "Administration of Human Fibroblast Interferon in Chronic Hepatitis–B Infection", *Lancet* 2(7987):645–7 (1976).

Makower and Wadler, "Interferons as Biomodulators of Fluoropyrimidines in the Treatment of Colorectal Cancer", *Semin. Oncol.* 26(6):663–71 (1999).

(List continued on next page.)

Primary Examiner—Lorraine Spector
Assistant Examiner—Dong Jiang
(74) Attorney, Agent, or Firm—Richard F. Trecartin; Robin M. Silva; Renee M. Kosslrk

(57) ABSTRACT

The invention relates to novel interferon-beta activity (IbA) proteins and nucleic acids. The invention further relates to the use of the IbA proteins in the treatment of IFN-β related disorders.

17 Claims, 23 Drawing Sheets

OTHER PUBLICATIONS

Sturzebecher et al., "Pharmacodynamic Comparison of Single Doses on IFN–β1a abd UFB–β1b in Healthy Volunteers", *J. Interferon Cytokine Res.* 19(11):1257–64 (1999).

Zein, "Interferons in the management of viral hepatitis", Cytokines Cell. Mol. Ther. 4(4):229–41 (1998).

Musch et al., "Phase II Clinical Trial of Combined Natural Interferon–β plus Recombinant Interferon–y Treatment of Chronic Hepatitis B", *Hepato–Gastroenterology* 45(24):2282–94 (1998).

Wadler et al., "Sequential Phase II Trials of Fluorouracil and Interferon $\beta_{ser}$ with or without Sargramostim in Patients with Advanced Colorectal Carcinoma", *Cancer J. Sci. Am.* 4(5):331–7 (1998).

Arnason, "Treatment of multiple sclerosis with interferon β", *Biomed Pharmacother* 53(8):344–50, (1999).

Comi et al., "Interferon beta treatment in multiple sclerosis: the European clinical trials", Mult. Scler. 1(6):317–20 (1996).

Kappos, "Multiple Sclerosis trials", *Lancet* 353(9171):2242–3 (1999).

Senda et al., "Three–dimensional crystal structure of recombinant murine interferon–β", EMBO J. 11(9):3193–3201 (1992).

Senda et al., "Refined Crystal Structure of Recominant Murine Interferon–β at 2.15 Å Resolution", *J. Mol. Biol.* 253(1):187–207 (1995).

Mitsui et al., "Structural, Functional and Evolutionary Implications of the Three–Dimensional Crystal Structure of Murine interfereon–β", *Pharmacol. Ther.* 58(1):93–132 (1993).

Mitsui et al., "Elucidation of the Basic Three–Dimensional Structure of Type I Interferons and Its Functional and Evolutionary Implications", *J. Interferon Cytokine Res.* 17(6):319–26 (1997).

Karpusas et al., "The crystal structure of human interferon β at 2.2–Å resolution", *Proc. Natl. Acad. Sci. U.S.A.* 94(22):11813–8 (1997).

Runkel et al., "Structural and Functional Differences Between Glycosylated and Non–glycosylated Forms of Human Interferon–β (IFN–β)", *Pharm. Res.* 15(4):641–9 (1998).

Runkel et al., "Differences in Activity between α and β Type I Interferons Explored by Mutational Analysis", J. Biol. Chem. 273(14):8003–8 (1998).

Hellinga et al., "Construction of New Ligand Binding Sites in Proteins of Known Structure; I. Computer–aided Modeling of Sites with Pre–defined Geometry", *J. Mol. Biol.* 222:763–785 (1991).

Hurley et al., "Design and Structural Analysis of Alternative Hydrophobic Core Packing Arrangements in Bacteriophage T4 Lysozyme", *J. Mol. Biol.* 224:1143–1154 (1992).

Desjarlais and Handel, "De novo design of the hydrophobic cores of proteins", *Protein Science* 4:2006–2018 (1995).

Harbury et al., "Repacing protein cores with backbone freedom: Structure prediction for coiled coils", *Proc. Natl. Acad. Sci. USA* 92:8408–8412 (1995).

Klemba et al., "Novel metal–binding proteins by design", *Struc. Biol.* 2(5):368–373 (1995).

Nautiyal, et al., "A Designed Heterotrimetic Coiled Coil", *Biochemistry* 34:11645–11651 (1995).

Betz and Grado, "Controlling Topology and Native–like Behavior fo de Novo–Designed Peptides: Design and Characerization of Antiparallel Four–Stranded Coiled Coils", *Biochemistry* 35:6955–6962 (1996).

Dahiyat and Mayo, "Protein Design automation", *Protein Science* 5:895–903 (1996).

Dahiyat and Mayo, "De Novo Protein Design: Fully Automated Sequence Selection", *Science* 278:82–87 (1997).

Dahayat et al., "De Novo Protein Design: Towards Fully Automated Sequence Selection", *J. Mol. Biol.* 273:789–796 (1997).

Dahiyat et al., "Automated design of the surface positions of protein helices", *Protein Science* 6:1333–1337 (1997).

Jones, "De novo protein design using pairwise potentials and a genetic algorith", *Protein Science* 3:567–574 (1994).

Kono and Doi, "Energy Minimization Method Using Automata Network for Sequence and Side–Chain Conformation Prediction From Given Backbone Geometry", *Proteins: Structure, Function and Genetics* 19:244–255 (1994).

Runkel, et al., "Systematic Mutational Mapping of Sites on Human Interferon–β–1a That Are Important for Receptor Binding and Functional Activity." *Biochemistry* 39:2538–2551 (2000).

\* cited by examiner

Chain-A: Sequence and Secondary Structure

```
  1 MSYNLLGFLQ RSSNFQCQKL LWQLNGRLEY CLKDRMNFDI PEEIKQLQQF
    HHHHHHHH   HHHHHHHHHH HTTS    SG GGGG           HHHHH

51 QKEDAALTIY EMLQNIFAIF RQDSSSTGWN ETIVENLLAN VYHQINHLKT
    HHHHHHHHH  HHHHHHHHHH TS   GGGT  HHHHHHHHHH HHHHHHHHH

101 VLEEKLEKED FTRGKLMSSL HLKRYYGRIL HYLKAKEYSH CAWTIVRVEI
    HHHHHHTTSS        SSSHH HHHHHHHHHH HHHHHTTT H HHHHHHHHHH

151 LRNFYFINRL TGYLRN
    HHHHHHHHHH HTT
```

FIG._1A

Chain-B: Sequence and Secondary Structure

```
  1 MSYNLLGFLQ RSSNFQCQKL LWQLNGRLEY CLKDRMNFDI PEEIKQLQQF
    HHHHHHHH   HHHHHHHHHH HHH            S        HHHH   S

51 QKEDAALTIY EMLQNIFAIF RQDSSSTGWN ETIVENLLAN VYHQINHLKT
    HHHHHHHHH  HHHHHHHHHH HS   TTT   HHHHHHHHHH HHHHHHHHH

101 VLEEKLEKED FTRGKLMSSL HLKRYYGRIL HYLKAKEYSH CAWTIVRVEI
    HHHHTTTTS         HHHHHHHH HHHHHHHHHH HHHHHTTT H HHHHHHHHHH

151 LRNFYFINRL TGYLRN
    HHHHHHHHHH HTT
```

FIG._1B

Human Interferon-Beta Gene Sequence

```
  1 atgaccaaca agtgtctcct ccaaattgct ctcctgttgt gcttctccac tacagctctt
 61 tccatgagct acaacttgct tggattccta caagaagca gcaattttca gtgtcagaag
121 ctcctgtggc aattgaatgg gaggcttgaa tattgcctca aggacaggat gaactttgac
181 atccctgagg agattaagca gctgcagcag ttccagaagg aggacgccgc attgaccatc
241 tatgagatgc tccagaacat ctttgctatt ttcagacaag attcatctag cactggctgg
301 aatgagacta ttgttgagaa cctcctggct aatgtctatc atcagataaa ccatctgaag
361 acagtcctgg aagaaaaact ggagaaagaa gatttttacca ggggaaaact catgagcagt
421 ctgcacctga aaagatatta tgggaggatt ctgcattacc tgaaggccaa ggagtacagt
481 cactgtgcct ggaccatagt cagagtggaa atcctaagga acttttactt cattaacaga
541 cttacaggtt acctccgaaa ctgaagatct cctagcctgt ccctctggga ctggacaatt
601 gcttcaagca ttcttcaacc agcagatgct gtttaagtga ctgatggcta atgtactgca
661 aatgaaagga cactagaaga ttttgaaatt ttattaaat tatgagttat ttttatttat
721 ttaaatttta ttttggaaaa taaattattt ttggtgc
```

FIG._1C

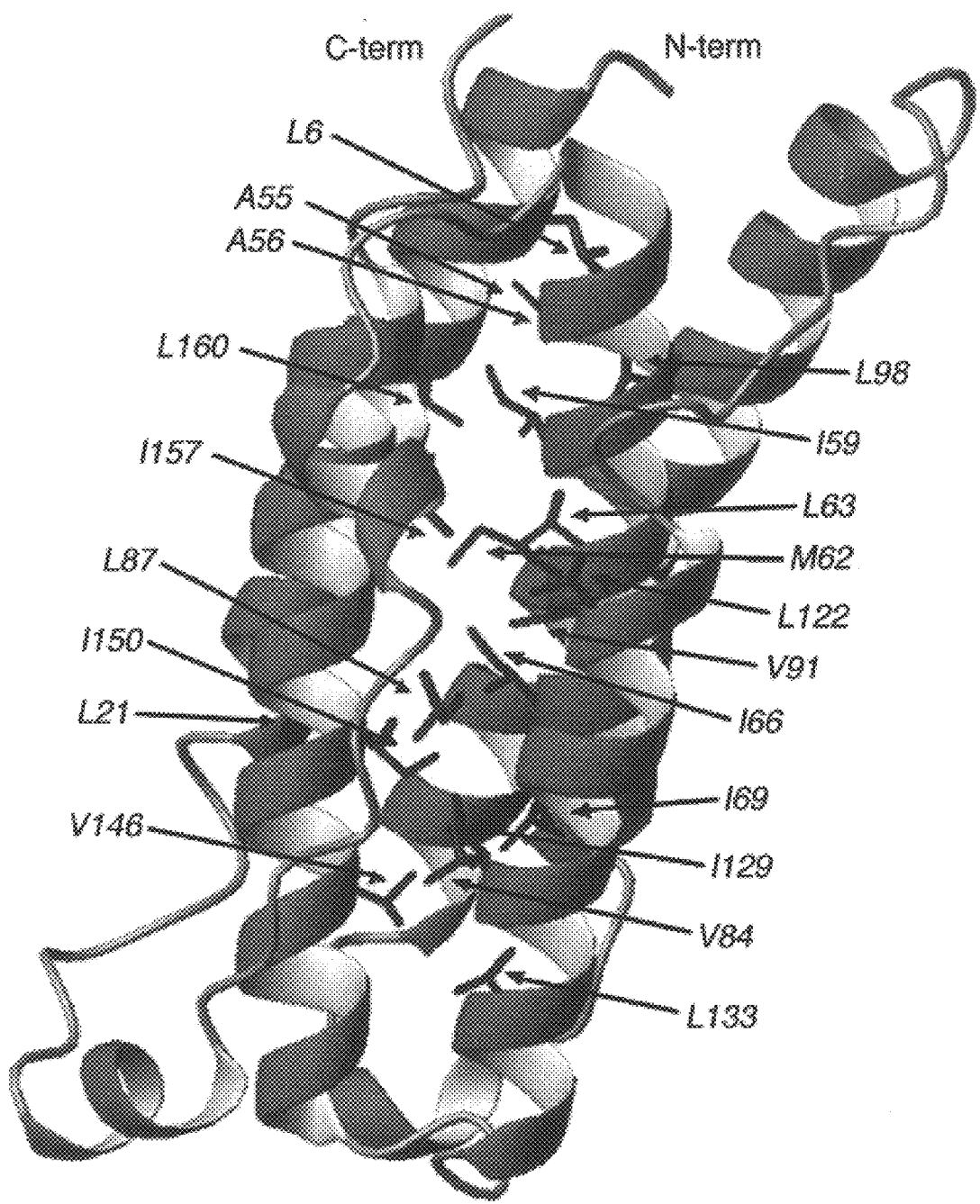
FIG._2

IFNβ Core 1 (A-Chain, B-Chain)

| 6 | 21 | 55 | 56 | 59 | 62 | 63 | 66 | 69 | 84 | 87 | 91 | 98 | 122 | 129 | 133 | 146 | 150 | 157 | 160 |
|---|----|----|----|----|----|----|----|----|----|----|----|----|-----|-----|-----|-----|-----|-----|-----|
| Leu | Leu | Ala | Ala | Ile | Met | Leu | Ile | Ile | Val | Leu | Val | Leu | Leu | Ile | Leu | Val | Ile | Ile | Leu |

IFNβ Core 2 (A-Chain, B-Chain)

| 1 | 6 | 10 | 14 | 17 | 21 | 38 | 50 | 55 | 56 | 58 | 59 | 61 | 62 | 63 | 66 | 69 | 70 | 81 | 84 |
|---|---|----|----|----|----|----|----|----|----|----|----|----|----|----|----|----|----|----|----|
| Met | Leu | Gln | Asn | Cys | Leu | Phe | Ala | Ala | Thr | Ile | Glu | Met | Leu | Ile | Ile | Phe | Glu | Val |
| 87 | 91 | 94 | 95 | 98 | 102 | 115 | 122 | 125 | 126 | 129 | 130 | 133 | 138 | 144 | 146 | 147 | 150 | 151 | 153 |
| Leu | Val | Gln | Ile | Leu | Leu | Lys | Leu | Tyr | Tyr | Ile | Leu | Leu | Tyr | Thr | Val | Arg | Ile | Leu | Asn |
| 154 | 157 | 159 | 160 | 161 | 163 | 164 |
| Phe | Ile | Arg | Leu | Thr | Tyr | Leu |

IFNβ Core 3, Core 4, Core 5, Core 6 (A-Chain); Core 5, Core 6, Core 7 (B-Chain)

| 1 | 6 | 10 | 13 | 14 | 17 | 18 | 21 | 38 | 50 | 55 | 56 | 58 | 59 | 61 | 62 | 63 | 66 | 69 | 70 |
|---|---|----|----|----|----|----|----|----|----|----|----|----|----|----|----|----|----|----|----|
| Met | Leu | Gln | Ser | Asn | Cys | Gln | Leu | Phe | Ala | Ala | Thr | Ile | Glu | Met | Leu | Ile | Ile | Phe |
| 72 | 74 | 76 | 77 | 81 | 84 | 87 | 90 | 91 | 94 | 95 | 98 | 102 | 114 | 115 | 118 | 122 | 125 | 126 | 129 |
| Gln | Ser | Ser | Thr | Glu | Val | Leu | Asn | Val | Gln | Ile | Leu | Leu | Gly | Lys | Ser | Leu | Tyr | Tyr | Ile |
| 130 | 132 | 133 | 136 | 138 | 139 | 142 | 143 | 144 | 146 | 147 | 150 | 151 | 153 | 154 | 157 | 159 | 160 | 161 | 163 |
| Leu | Tyr | Leu | Lys | Tyr | Ser | Ala | Trp | Thr | Val | Arg | Ile | Leu | Asn | Phe | Ile | Arg | Leu | Thr | Tyr |
| 164 |
| Leu |

IFNβ Core 3, Core 4 (B-Chain)

| 1 | 6 | 10 | 13 | 14 | 15 | 17 | 21 | 38 | 50 | 55 | 56 | 58 | 59 | 61 | 62 | 63 | 66 | 69 | 70 |
|---|---|----|----|----|----|----|----|----|----|----|----|----|----|----|----|----|----|----|----|
| Met | Leu | Gln | Ser | Asn | Phe | Cys | Leu | Phe | Ala | Ala | Thr | Ile | Glu | Met | Leu | Ile | Ile | Phe |
| 72 | 74 | 76 | 77 | 81 | 84 | 87 | 90 | 91 | 94 | 95 | 98 | 102 | 114 | 115 | 118 | 122 | 125 | 126 | 129 |
| Gln | Ser | Ser | Thr | Glu | Val | Leu | Asn | Val | Gln | Ile | Leu | Leu | Gly | Lys | Ser | Leu | Tyr | Tyr | Ile |
| 130 | 132 | 133 | 136 | 138 | 139 | 142 | 143 | 144 | 146 | 147 | 150 | 151 | 153 | 154 | 157 | 159 | 160 | 161 | 163 |
| Leu | Tyr | Leu | Lys | Tyr | Ser | Ala | Trp | Thr | Val | Arg | Ile | Leu | Asn | Phe | Ile | Arg | Leu | Thr | Tyr |
| 164 |
| Leu |

FIG._3

```
Res  Cons
Num  Seq   Other Mutations
^^^  ^^^^^ ^^^^^^^^^^^^^^^
  6  L:85.0 A:14.7 F:  .3
 21  L:98.7 I:  .7 V:  .4 A:  .1 Y:  .1
 55  A:100.0
 56  A:100.0
 59  I:66.1 V:32.3 A:  .9 L:  .7
 62  M:96.3 I: 3.3 V:  .4
 63  L:99.6 A:  .4
 66  I:48.9 L:45.5 V: 5.4 A:  .2
 69  I:77.7 V:19.5 L: 2.8
 84  I:40.5 L:39.4 V:19.6 A:  .5
 87  F:78.7 L:18.4 I: 2.1 Y:  .6 V:  .2
 91  V:83.0 I:16.1 A:  .9
 98  L:97.6 A: 2.4
122  L:100.0
129  I:75.6 V:20.7 L: 2.9 A:  .8
133  L:100.0
146  V:83.8 I:15.5 A:  .7
150  I:81.6 V:18.2 A:  .2
157  I:81.5 V:13.4 L: 4.7 A:  .4
160  L:73.5 I:16.5 V: 9.4 A:  .6
```

FIG._4A

```
  1 MSYNLLGFLQ RSSNFQCQKL LWQLNGRLEY CLKDRMNFDI PEEIKQLQQF
 51 QKEDAALTIY EMLQNIFAIF RQDSSSTGWN ETIIENFLAN VYHQINHLKT
101 VLEEKLEKED FTRGKLMSSL HLKRYYGRIL HYLKAKEYSH CAWTIVRVEI
151 LRNFYFINRL TGYLRN
```

FIG._4B

```
Res  Cons
Num  Seq   Other Mutations
^^^  ^^^^  ^^^^^^^^^^^^^^^
  1  M:100.0
  6  L:99.1  A:   .9
 10  Q:100.0
 14  N:100.0
 17  C:100.0
 21  L:59.3  I:39.7  V:   .9  F:   .1
 38  F:100.0
 50  F:100.0
 55  A:100.0
 56  A:100.0
 58  T:100.0
 59  I:93.4  V: 6.4  L:   .2
 61  E:100.0
 62  M:98.4  L: 1.2  I:   .3  V:   .1
 63  L:88.6  F:11.4
 66  L:85.1  L: 9.9  V: 5.0
 69  I:82.7  V:15.7  L: 1.6
 70  F:100.0
 81  E:100.0
 84  I:76.5  L:14.1  V: 8.8  A:   .6
 87  F:69.9  F:11.8  I:10.1  V: 8.0  Y:  .1  A:  .1
 91  I:81.7  V:11.5  L: 6.8
 94  Q:100.0
 95  I:100.0
 98  F:68.8  L:31.2
102  L:100.0
115  K:100.0
122  L:50.7  I:27.4  V:20.9  A: 1.0
125  Y:100.0
126  Y:100.0
129  I:60.7  L:34.8  V: 4.5
130  L:100.0
133  L:100.0
138  Y:100.0
144  T:100.0
146  V:95.2  I: 3.5  A: 1.3
147  R:100.0
150  I:68.3  L:16.5  A:12.2  V: 3.0
151  L:100.0
153  N:100.0
154  F:100.0
157  L:51.4  I:42.7  V: 5.8  A:  .1
159  R:100.0
160  L:86.8  I: 9.9  V: 3.3
161  T:100.0
163  Y:100.0
164  L:100.0
```

FIG._5A

```
  1  MSYNLLGFLQ RSSNFQCQKL LWQLNGRLEY CLKDRMNFDI PEEIKQLQQF
 51  QKEDAALTIY EMLQNIFAIF RQDSSSTGWN ETIIENLLAN IYHQINHEKT
101  VLEEKLEKED FTRGKLMSSL HIKRYYGRIL HYLKAKEYSH CAWTIVRVEI
151  LRNFYFLNRL TGYLRN
```

FIG._5B

```
Res  Cons
Num  Seq   Other Mutations
^^^  ^^^^  ^^^^^^^^^^^^^^^
  1  M:100.0
  6  L:97.6  F:  2.4
 10  Q:100.0
 13  F:67.7  Y:31.4  L:  .7  I:  .2
 14  N:100.0
 17  C:88.7  A: 6.9  L: 3.9  V:  .5
 18  Q:100.0
 21  L:85.4  I:14.0  V:  .5  F:  .1
 38  F:100.0
 50  F:100.0
 55  A:100.0
 56  A:100.0
 58  T:100.0
 59  I:81.4  V:15.9  L: 2.3  A:  .4
 61  E:100.0
 62  M:91.3  I: 8.7
 63  L:69.8  F:29.8  Y:  .4
 66  I:91.6  V: 7.8  L:  .6
 69  I:66.8  V:33.2
 70  F:100.0
 72  Q:100.0
 74  S:100.0
 76  S:100.0
 77  T:100.0
 81  E:100.0
 84  I:98.7  L: 1.3
 87  L:73.8  I:15.1  V:10.4  F:  .7
 90  N:100.0
 91  I:66.4  L:19.2  V:13.8  A:  .3  F:  .3

```
  1 MSYNLLGFLQ  RSFNFQCQKL  LWQLNGRLEY  CLKDRMNFDI  PEEIKQLQQF
 51 QKEDAALTIY  EMLQNIFAVF  RQDSSSTGWN  ETIIENLLAN  IYHQINHFKT
101 VLEEKLEKED  FTRGKLMASL  HIKRYYGRIL  HYLKAKEYSH  CAWTIIRVEI
151 LRNFYFLNRL  AGYLRN
```

FIG._6B

```
  1 MSYNLLGFLQ  RSYNFQCQKL  LWQLNGRLEY  CLKDRMNFDI  PEEIKQLQQF
 51 QKEDAALTIY  EMLQNIFAVF  RQDSSSTGWN  ETIIENLLAN  IYHQINHFKT
101 VLEEKLEKED  FTRGKLMVSL  HVKRYYGRIL  HYLKAKEYSH  CAWTIIRVEI
151 LRNFYFLNRL  AGYLRN
```

FIG._6C

```
  1 MSYNLLGFLQ  RSFNFQCQKL  LWQLNGRLEY  CLKDRMNFDI  PEEIKQLQQF
 51 QKEDAALTIY  EMLQNIFAIF  RQDSSSTGWN  ETIIENLLAN  IYHQINHFKT
101 VLEEKLEKED  FTRGKLMASL  HIKRYYGRIL  HYLKAKEYSH  CAWTIVRVEI
151 LRNFYFLNRL  AGYLRN
```

FIG._6D

```
Res  Cons
Num  Seq  Other Mutations
^^^  ^^^^  ^^^^^^^^^^^^^^^
  1  M:100.0
  6  L:98.1 F:  1.9
 10  Q:100.0
 13  F:67.3 Y:32.7
 14  N:100.0
 17  D:82.9 T:  7.1 A:  4.5 L:  4.1 V:  1.4
 18  Q:100.0
 21  L:85.8 I:13.7 V:   .5
 38  F:100.0
 50  F:100.0
 55  A:100.0
 56  A:100.0
 58  T:100.0
 59  I:77.8 V:19.1 L:  2.6 A:   .5
 61  E:100.0
 62  M:92.1 I:  7.9
 63  L:73.2 F:25.9 Y:   .9
 66  H:93.3 V:  5.9 L:   .8
 69  H:67.7 V:32.3
 70  F:100.0
 72  Q:100.0
 74  S:100.0
 76  S:100.0
 77  T:100.0
 81  E:100.0
 84  I:99.9 L:   .1
 87  L:75.1 I:14.7 V:  8.8 F:  1.4
 90  N:100.0
 91  I:75.0 V:14.6 L:10.3 A:   .1
```

```
  1 MSYNLLGFLQ RS<u>F</u>NFQ<u>D</u>QKL LWQLNGRLEY CLKDRMNFDI PEEIKQLQQF
 51 QKEDAALTIY EMLQNIFA<u>V</u>F RQDSSSTGWN ETI<u>I</u>ENLLAN <u>I</u>YHQINH<u>F</u>KT
101 VLEEKLEKED FTRGKLM<u>A</u>SL H<u>I</u>KRYYGRIL HYLKAKEYSH CAWTI<u>I</u>RVEI
151 LRNFYF<u>L</u>NRL <u>A</u>GYLRN
```

FIG._7B

```
  1 MSYNLLGFLQ RS<u>Y</u>NFQ<u>D</u>QKL LWQLNGRLEY CLKDRMNFDI PEEIKQLQQF
 51 QKEDAALTIY EMLQNIFA<u>V</u>F RQDSSSTGWN ETI<u>I</u>ENLLAN <u>I</u>YHQINH<u>F</u>KT
101 VLEEKLEKED FTRGKLM<u>V</u>SL H<u>V</u>KRYYGRIL HYLKAKEYSH CAWTI<u>I</u>RVEI
151 LRNFYF<u>L</u>NRL <u>A</u>GYLRN
```

FIG._7C

```
  1 MSYNLLGFLQ RS<u>F</u>NFQ<u>D</u>QKL LWQLNGRLEY CLKDRMNFDI PEEIKQLQQF
 51 QKEDAALTIY EMLQNIFAIF RQDSSSTGWN ETI<u>I</u>ENLLAN <u>I</u>YHQINH<u>F</u>KT
101 VLEEKLEKED FTRGKLM<u>A</u>SL H<u>I</u>KRYYGRIL HYLKAKEYSH CAWTIVRVEI
151 LRNFYF<u>L</u>NRL <u>A</u>GYLRN
```

FIG._7D

```
Res  Cons
Num  Seq   Other Mutations
^^^  ^^^^  ^^^^^^^^^^^^^^^^
  1  M:100.0
  6  L:96.2  F: 3.8
 10  Q:100.0
 13  E:63.4  A:34.0  S: 1.3  G:  .8  T: 3  C: .2
 14  N:100.0
 17  C:55.8  D:38.7  A: 5.5
 18  Q:100.0
 21  L:85.3  I:13.7  V:  .8  A: .2
 38  F:100.0
 50  F:100.0
 55  A:100.0
 56  A:100.0
 58  T:100.0
 59  I:71.6  V:27.9  L:  .5
 61  E:100.0
 62  M:77.4  I:14.4  L: 8.2
 63  L:59.8  F:40.2
 66  I:85.8  V:13.5  L:  .7
 69  I:73.1  V:26.9
 70  F:100.0
 72  Q:100.0
 74  S:100.0
 76  S:100.0
 77  T:100.0
 81  E:100.0
 84  I:99.5  L:  .5
 87  L:75.4  I:16.7  V: 7.9
 90  N:100.0
 91  I:63.6  L:25.0  V:11.4
 94  Q:100.0
 95  I:100.0
 98  L:94.5  A: 5.5
102  L:100.0
114  G:100.0
115  K:100.0
118  C:100.0
122  L:77.2  I:22.8
125  Y:100.0
126  Y:100.0
129  I:100.0
130  L:100.0
132  Y:100.0
133  L:100.0
136  K:100.0
138  Y:100.0
139  S:100.0
142  A:100.0
143  W:100.0
144  T:100.0
146  I:100.0
147  R:100.0
150  I:98.2  L: 1.5  V:  .3
151  L:100.0
153  N:100.0
154  F:97.9  Y: 1.1  L: 1.0
157  I:43.8  V:41.7  L:13.9  A: .6
159  R:100.0
160  L:78.6  I:21.4
161  C:99.8  A:  .2
163  Y:100.0
164  L:100.0
```

FIG._8A

```
  1 MSYNLLGFLQ RS<u>E</u>NFQ<u>D</u>QKL LWQLNGRLEY CLKDRMNFDI PEEIKQLQQF
 51 QKEDAALTIY EMLQNIFAIF RQDSSSTGWN ETI<u>I</u>ENLLAN <u>I</u>YHQINHLKT
101 VLEEKLEKED FTRGKLM<u>C</u>SL HLKRYYGRIL HYLKAKEYSH CAWTI<u>I</u>RVEI
151 LRNFYFINRL <u>C</u>GYLRN
```

FIG._8B

```
  1 MSYNLLGFLQ RS<u>A</u>NFQCQKL LWQLNGRLEY CLKDRMNFDI PEEIKQLQQF
 51 QKEDAALTIY EMLQNIFAIF RQDSSSTGWN ETI<u>I</u>ENLLAN <u>I</u>YHQINHLKT
101 VLEEKLEKED FTRGKLM<u>C</u>SL HLKRYYGRIL HYLKAKEYSH CAWTI<u>I</u>RVEI
151 LRNFYF<u>L</u>NRL <u>C</u>GYLRN
```

FIG._8C

```
  1 MSYNLLGFLQ RS<u>E</u>NFQ<u>D</u>QKL LWQLNGRLEY CLKDRMNFDI PEEIKQLQQF
 51 QKEDAALTIY EMLQNIFAIF RQDSSSTGWN ETI<u>I</u>ENLLAN <u>I</u>YHQINHLKT
101 VLEEKLEKED FTRGKLM<u>C</u>SL HLKRYYGRIL HYLKAKEYSH CAWTIVRVEI
151 LRNFYFINRL <u>C</u>GYLRN
```

FIG._8D

| Res Num | Cons Seq | Other Mutations | | | | | |
|---|---|---|---|---|---|---|---|
| 1 | M:100.0 | | | | | | |
| 6 | L:96.8 | F: 3.2 | | | | | |
| 10 | Q:100.0 | | | | | | |
| 13 | E:66.7 | A:31.9 | S: 1.2 | T: .1 | G: .1 | | |
| 14 | N:100.0 | | | | | | |
| 17 | D:80.8 | A:10.1 | T: 9.1 | | | | |
| 18 | Q:100.0 | | | | | | |
| 21 | L:88.1 | I:11.6 | V: .3 | | | | |
| 38 | F:100.0 | | | | | | |
| 50 | F:100.0 | | | | | | |
| 55 | A:100.0 | | | | | | |
| 56 | A:100.0 | | | | | | |
| 58 | T:100.0 | | | | | | |
| 59 | I:69.4 | V:29.2 | L: 1.3 | A: .1 | | | |
| 61 | E:100.0 | | | | | | |
| 62 | M:85.3 | I:14.7 | | | | | |
| 63 | L:52.9 | F:47.1 | | | | | |
| 66 | I:90.9 | V: 8.6 | L: .5 | | | | |
| 69 | H:79.1 | V:20.9 | | | | | |
| 70 | F:100.0 | | | | | | |
| 72 | Q:100.0 | | | | | | |
| 74 | S:100.0 | | | | | | |
| 76 | S:100.0 | | | | | | |
| 77 | T:100.0 | | | | | | |
| 81 | E:100.0 | | | | | | |
| 84 | I:99.6 | L: .4 | | | | | |
| 87 | L:77.8 | I:15.1 | V: 7.1 | | | | |
| 90 | N:100.0 | | | | | | |
| 91 | I:72.1 | L:16.2 | V:11.7 | | | | |
| 94 | Q:100.0 | | | | | | |
| 95 | I:100.0 | | | | | | |
| 98 | L:96.6 | A: 3.4 | | | | | |
| 102 | L:100.0 | | | | | | |
| 114 | G:100.0 | | | | | | |
| 115 | K:100.0 | | | | | | |
| 118 | A:100.0 | | | | | | |
| 122 | L:84.2 | I:15.8 | | | | | |
| 125 | Y:100.0 | | | | | | |
| 126 | Y:100.0 | | | | | | |
| 129 | I:100.0 | | | | | | |
| 130 | L:100.0 | | | | | | |
| 132 | Y:100.0 | | | | | | |
| 133 | L:100.0 | | | | | | |
| 136 | K:100.0 | | | | | | |
| 138 | Y:100.0 | | | | | | |
| 139 | S:100.0 | | | | | | |
| 142 | A:100.0 | | | | | | |
| 143 | W:100.0 | | | | | | |
| 144 | T:100.0 | | | | | | |
| 146 | I:100.0 | | | | | | |
| 147 | R:100.0 | | | | | | |
| 150 | I:99.1 | L: .9 | | | | | |
| 151 | L:100.0 | | | | | | |
| 153 | N:100.0 | | | | | | |
| 154 | F:98.5 | Y: 1.1 | L: .4 | | | | |
| 157 | I:43.3 | V:36.3 | L:19.5 | A: .9 | | | |
| 159 | R:100.0 | | | | | | |
| 160 | L:79.6 | I:20.4 | | | | | |
| 161 | A:55.1 | T:23.9 | D:21.0 | | | | |
| 163 | Y:100.0 | | | | | | |
| 164 | L:100.0 | | | | | | |

FIG._9A

```
  1 MSYNLLGFLQ RSENFQDQKL LWQLNGRLEY CLKDRMNFDI PEEIKQLQQF
 51 QKEDAALTIY EMLQNIFAVF RQDSSSTGWN ETIIENLLAN IYHQINHLKT
101 VLEEKLEKED FTRGKLMASL HIKRYYGRIL HYLKAKEYSH CAWTIIRVEI
151 LRNFYFLNRL AGYLRN
```

FIG._9B

```
  1 MSYNLLGFLQ RSENFQDQKL LWQLNGRLEY CLKDRMNFDI PEEIKQLQQF
 51 QKEDAALTIY EMLQNIFAIF RQDSSSTGWN ETIIENLLAN IYHQINHLKT
101 VLEEKLEKED FTRGKLMASL HLKRYYGRIL HYLKAKEYSH CAWTIIRVEI
151 LRNFYFLNRL TGYLRN
```

FIG._9C

```
  1 MSYNLLGFLQ RSENFQDQKL LWQLNGRLEY CLKDRMNFDI PEEIKQLQQF
 51 QKEDAALTIY EMLQNIFAIF RQDSSSTGWN ETIIENLLAN IYHQINHLKT
101 VLEEKLEKED FTRGKLMASL HIKRYYGRIL HYLKAKEYSH CAWTIVRVEI
151 LRNFYFLNRL AGYLRN
```

FIG._9D

```
Res  Cons
Num  Seq   Other Mutations
^^^  ^^^^^ ^^^^^^^^^^^^^^
  6  L:98.4 A: 1.6
 21  L:100.0
 55  A:100.0
 56  A:100.0
 59  I:78.0 V:21.1 A:  .6 L:   .3
 62  M:84.7 I:14.4 V:  .9
 63  L:84.3 F:15.7
 66  I:53.1 L:42.4 V: 4.5
 69  I:91.2 V: 8.8
 84  I:62.3 V:25.4 L:11.7 A:  .6
 87  F:74.6 L:21.5 W: 1.9 Y: 1.3 I:  .6 V:  .1
 91  I:54.7 V:43.6 L: 1.5 A:  .2
 98  L:98.1 A: 1.9
122  L:82.8 F:13.6 I: 3.6
129  I:77.5 V:22.5
133  L:100.0
146  V:99.7 A:  .3
150  I:88.5 V:11.0 L:  .5
157  I:78.4 V:15.1 L: 6.5
160  L:59.2 F:39.4 Y: 1.3 A:  .1
```

FIG._10A

```
  1 MSYNLLGFLQ RSSNFQCQKL LWQLNGRLEY CLKDRMNFDI PEEIKQLQQF
 51 QKEDAALTIY EMLQNIFAIF RQDSSSTGWN ETIIENFLAN VYHQINHLKT
101 VLEEKLEKED FTRGKLMSSL HLKRYYGRIL HYLKAKEYSH CAWTIVRVEI
151 LRNFYFINRL TGYLRN
```

FIG._10B

```
Res Cons  Other Mutations
Num Seq   ^^^^^^^^^^^^^^^^
^^^ ^^^^
  1 M:100.0
  6 L:98.5 A: 1.5
 10 Q:100.0
 14 N:100.0
 17 C:100.0
 21 L:84.6 F:15.4
 38 F:100.0
 50 F:100.0
 55 A:100.0
 56 L:97.6 A: 2.4
 58 T:100.0
 59 I:89.3 V: 8.6 A: 2.1
 61 E:100.0
 62 M:84.6 L:11.1 I: 3.4 V:   .9
 63 L:67.2 F:32.4 Y: .4
 66 I:93.1 L: 3.6 V: 3.3
 69 I:90.4 V: 9.6
 70 F:100.0
 81 E:100.0
 84 I:74.9 V:15.5 L: 8.4 A: 1.2
 87 F:69.3 L:24.4 I: 5.5 V: .4 Y: .4
 91 I:68.5 L:27.7 V: 3.8

```
  1 MSYNLLGFLQ RSSNFQCQKL LWQLNGRLEY CLKDRMNFDI PEEIKQLQQF
 51 QKEDALLTIY EMFQNIFAIF RQDSSSTGWN ETIIENFLAN IYHQINHLKT
101 VLEEKLEKED FTRGKLMSSL HFKRYYGRIL HYLKAKEYSH CAWTIVRVEI
151 LRNFYFINRL TGYLRN
```

```
Res  Cons  Other Mutations
Num  Seq   ^^^^^^^^^^^^^^^^
^^^  ^^^^
  1  M:100.0
  6  L:100.0
 10  Q:100.0
 13  L:92.7  A: 7.3
 14  N:100.0
 15  F:100.0
 17  C:64.8  A:25.8  V: 6.1  L: 2.2  I: 1.1
 21  L:85.8  F:14.1  Y:  .1
 38  F:100.0
 50  F:100.0
 55  A:100.0
 56  L:99.8  A:  .2
 58  T:100.0
 59  H:98.0  A: 1.9  L:  .1
 61  E:100.0
 62  M:79.9  I:12.2  L: 7.4  V:  .5
 63  L:75.4  F:22.9  Y: 1.7
 66  H:73.8  L:15.4  V:10.8
 69  H:96.7  A: 1.7  L: 1.6
 70  F:100.0
 72  Q:100.0
 74  S:100.0
 76  S:100.0
 77  T:100.0
 81  E:100.0
 84  H:100.0
 87  F:46.8  L:45.0  I: 7.1  V:  .6  Y:  .4  W:  .1
 90  N:100.0
 91  I:52.6  L:27.8  V:15.1  F: 4.3  Y:  .1  A:  .1

94  Q:100.0
 95  I:100.0
 98  L:97.8  F: 2.2
102  L:100.0
114  F:100.0
115  K:100.0
118  L:100.0
122  I:39.9  L:39.0  F:21.1
125  Y:100.0
126  Y:100.0
129  I:99.1  L:  .9
130  L:100.0
132  Y:100.0
133  L:100.0
136  K:100.0
138  Y:100.0
139  S:100.0
142  A:100.0
143  W:100.0
144  T:100.0
146  V:99.1  I:  .9
147  R:100.0
150  I:71.6  L:14.2  V:12.5  F: 1.7
151  L:100.0
153  N:100.0
154  F:89.9  L: 8.9  Y: 1.2
157  R:62.2  L:28.0  V: 9.7  A:  .1
159  R:100.0
160  L:97.3  F: 2.7
161  A:100.0
163  Y:100.0
164  L:100.0
```

```
  1 MSYNLLGFLQ RSLNFQCQKL LWQLNGRLEY CLKDRMNFDI PEEIKQLQQF

51 QKEDALLTIY EMLQNIFAIF RQDSSSTGWN ETIIENLLAN IYHQINHLKT

101 VLEEKLEKED FTRFKLMLSL HIKRYYGRIL HYLKAKEYSH CAWTIVRVEI

151 LRNFYFINRL AGYLRN
```

```
Res Cons  Other Mutations
Num ^^^^  ^^^^^^^^^^^^^^^
^^^
  1 M:100.0
  6 L: 98.6 F: 1.4
 10 Q:100.0
 13 L: 42.5 E: 25.4 S: 25.1 T: 3.1 D: 2.4 A: 1.5
 14 N:100.0
 15 F:100.0
 17 A: 53.0 T: 24.0 V: 7.6 I: 6.5 L: 5.7 D: 3.1 E: .1
 21 L: 94.2 F: 5.8
 38 F:100.0
 50 A:100.0
 55 L: 97.7 A: 2.3
 56 T:100.0
 58 H: 92.0 V: 8.0
 59 E:100.0
 61 M: 82.1 L: 11.6 I: 6.0 V: .3
 62 L: 75.3 F: 24.7
 63 H: 85.2 L: 12.2 V: 2.6
 66 H:100.0
 70 F:100.0
 72 S:100.0
 74 S:100.0
 76 T:100.0
 77 E:100.0
 81 H:100.0
 84 F: 80.7 L: 14.1 I: 4.8 Y: .4
 87 N:100.0
 90 I: 53.7 L: 35.3 V: 9.8 A: .9 F: .3
 91
 94  Q:100.0
 95  I:100.0
 98  L: 97.9 A: 2.1
102  L:100.0
114  F:100.0
115  K:100.0
118  L:100.0
122  I: 46.0 L: 30.0 F: 24.0
125  Y:100.0
126  H:100.0
129  L:100.0
130  L:100.0
132  Y:100.0
133  K:100.0
136  Y:100.0
138  S:100.0
139  A:100.0
142  W:100.0
143  T:100.0
144  V:100.0
146  R:100.0
147  I: 92.3 V: 5.0 L: 2.7
150  L:100.0
151  N:100.0
153  F: 88.6 L: 11.4
154  I: 72.3 L: 21.2 V: 6.5
157  R:100.0
159  L: 74.2 F: 25.8
160  E: 85.0 T: 15.0
161  Y:100.0
163  L:100.0
```

FIG. 13A

```
  1 MSYNLLGFLQ RSLNFQAQKL LWQLNGRLEY CLKDRMNFDI PEEIKQLQQF
 51 QKEDALLTIY EMLQNIFAIF RQDSSSTGWN ETIENFLAN  LYHQINHLKT
101 VLEEKLEKED FTRFKLMLSL HIKRYYGRIL HYLKAKEYSH CAWTIVRVEI
151 LRNFYFINRL EGYLRN
```

```
Res  Cons
Num  Seq  Other Mutations
<<<  <<<  <<<<<<<<<<<<<<<<
  1  M:100.0
  6  L:99.0  F: .8  A: .2
 10  Q:100.0
 13  E:38.9  C:36.6  S:21.7  D: 2.8
 14  N:100.0
 17  C:91.2  A: 5.1  D: 3.1  T: .6
 18  Q:100.0
 21  L:72.1  F:27.9
 38  F:100.0
 50  F:100.0
 55  A:100.0
 56  L:97.6  A: 2.4
 58  T:100.0
 59  I:98.5  V: 1.5
 61  E:100.0
 62  M:81.8  L:10.2  I: 8.0
 63  L:83.9  F:16.1
 66  H:89.6  L: 8.0  V: 2.4
 69  H:99.6  A: .2  L: .2
 70  F:100.0
 72  Q:100.0
 74  S:100.0
 76  S:100.0
 77  T:100.0
 81  E:100.0
 84  I:82.4  V:13.8  L: 3.8
 87  L:93.9  I: 6.0  V: .1
 90  N:100.0
 91  I:58.7  L:19.0  F:17.2  V: 5.1
 94  Q:100.0
 95  I:100.0
 98  L:98.9  A: 1.1
102  L:100.0
114  L:100.0
115  K:100.0
118  E:92.8  C: 7.2
122  L:40.7  I:31.4  F:27.1  W: .8
125  Y:100.0
126  Y:100.0
129  I:99.8  L: .2
130  L:100.0
132  Y:100.0
133  K:100.0
136  Y:100.0
138  Y:100.0
139  S:100.0
142  A:100.0
143  W:100.0
144  T:100.0
146  V:99.8  I: .2
147  R:100.0
150  I:91.3  L: 8.3  F: .2
151  L:100.0
153  N:100.0
154  F:82.7  L:17.3
157  R:69.1  L:24.5  V: 6.4
159  R:100.0
160  L:87.6  F:10.9  I: 1.5
161  E:84.3  T:15.7
163  Y:100.0
164  L:100.0
```

FIG. 14B

```
  1 MSYNLLGFLQ RSENFQCQKL LWQLNGRLEY CLKDRMNFDI PEEIKQLQQF
 51 QKEDALLTIY EMLQNIFAIF RQDSSSTGWN ETIIENLLAN IYHQINHLKT
101 VLEEKLEKED FTRLKLMESL HLKRYYGRIL HYLKAKEYSH CAWTIVRVEI
151 LRNFYFINRL EGYLRN
```

```
Res Cons Other Mutations
Num Seq  ^^^^^^^^^^^^^^^^
^^^ ^^^
  1 M:100.0
  6 L: 98.7 F:  1.3
 10 Q:100.0
 13 S: 49.4 E:33.2 T: 7.9 D: 5.2 A: 4.3
 14 N:100.0
 17 T: 36.3 D:29.4 A:29.3 E: 4.3 S:  .7
 18 Q:100.0
 21 L: 78.3 F:21.6 Y:  .1
 38 F:100.0
 50 F:100.0
 55 A:100.0
 56 L: 98.1 A: 1.9
 58 T:100.0
 59 I: 98.6 V: 1.4
 61 E:100.0
 62 M: 82.4 L:12.1 I: 5.5
 63 L: 78.7 F:21.3
 66 I: 90.4 L: 6.0 V: 3.6
 69 I:100.0
 70 F:100.0
 72 Q:100.0
 74 S:100.0
 76 S:100.0
 77 T:100.0
 81 E:100.0
 84 I: 94.0 L: 6.0
 87 L: 93.4 I: 6.6
 90 N:100.0
 91 I: 76.4 L:11.7 F: 8.1 V: 3.8
 94 Q:100.0
 95 I:100.0
 98 L: 97.9 A: 2.1
102 L:100.0
114 L:100.0
115 K:100.0
118 E: 99.4 A:  .6
122 L: 41.3 I:38.6 F:19.2 W:  .6
125 Y:100.0
126 Y:100.0
129 I:100.0
130 L:100.0
132 L:100.0
133 K:100.0
136 K:100.0
138 Y:100.0
139 S:100.0
142 A:100.0
143 W:100.0
144 T:100.0
146 V:100.0
147 R:100.0
150 I: 83.4 L:15.6 V: 1.0
151 L:100.0
153 N:100.0
154 F: 87.2 L:12.6 Y:  .2
157 I: 65.6 L:27.6 V: 6.8
159 R:100.0
160 E: 89.6 F:10.4
161 E: 86.4 T:12.1 G: 1.5
163 Y:100.0
164 L:100.0
```

} *FIG._15A*

```
  1 MSYNLLGFLQ RSSNFQTQKL LWQLNGRLEY CLKDRMNFDI PEEIKQLQQF
 51 QKEDALLTIY EMLQNIFAIF RQDSSSTGWN ETIENLLAN  IYHQINHLKT
101 VLEEKLEKED FTRLKLMESL HLKRYYGRIL HYLKAKEYSH CAWTIVRVEI
151 LRNFYFINRL EGYLRN
```

```
Res Cons Other Mutations
Num Seq
^^^ ^^^^ ^^^^^^^^^^^^^^^
  1 M:100.0
  6 L: 96.9  F: 3.1
 10 Q:100.0
 13 S: 47.4  E:35.2  T: 7.7  D: 6.1  A: 3.6
 14 N:100.0
 17 T: 32.8  A:31.0  D:29.0  E: 5.0  S: 1.4  G: .8
 18 Q:100.0
 21 L: 77.9  F:22.0  Y: .1
 38 F:100.0
 50 F:100.0
 55 A: 97.6  A: 2.4
 56 L: 97.6
 58 T:100.0
 59 H: 99.9  V: .1
 61 E:100.0
 62 M: 78.5  L:13.5  I: 8.0
 63 L: 80.7  F:19.3
 66 L: 85.6  L: 7.8  V: 6.6
 69 H: 98.8  A: 1.2
 70 F:100.0
 72 Q:100.0
 74 S:100.0
 77 T:100.0
 81 E:100.0
 84 I: 99.7  L: .3
 87 L: 92.7  I: 7.3
 90 N:100.0
 91 I: 73.3  L:13.3  F: 8.7  V: 4.7
 94 Q:100.0
 95 I:100.0
 98 L: 96.4  A: 3.6
102 L:100.0
114 G:100.0
115 K:100.0
118 E:100.0
122 L: 43.6  I:38.0  F:18.4
125 Y:100.0
126 I:100.0
129 H:100.0
130 L:100.0
132 Y:100.0
133 L:100.0
136 K:100.0
138 Y:100.0
139 S:100.0
142 A:100.0
143 W:100.0
144 T:100.0
146 V:100.0
147 E:100.0
150 I: 76.2  L:17.8  V: 5.4  F: .6
151 L:100.0
153 N:100.0
154 F: 85.5  L:14.1  Y: .4
157 I: 65.7  L:26.6  V: 7.7
159 R:100.0
160 L: 95.2  I: 4.8
161 E: 98.1  G: 1.9
163 Y:100.0
164 L:100.0
```

FIG._16B

```
  1 MSYNLLGFLQ RSSNFQTQKL LWQLNGRLEY CLKDRMNFDI PEEIKQLQQF
 51 QKEDALLTIY EMLQNIFAIF RQDSSSTGWN ETIIENLLAN IYHQINHLKT
101 VLEEKLEKED FTRGKLMESL HLKRYYGRIL HYLKAKEYSH CAWTIVRVEI
151 LRNFYFINRL EGYLRN
```

FIG._17
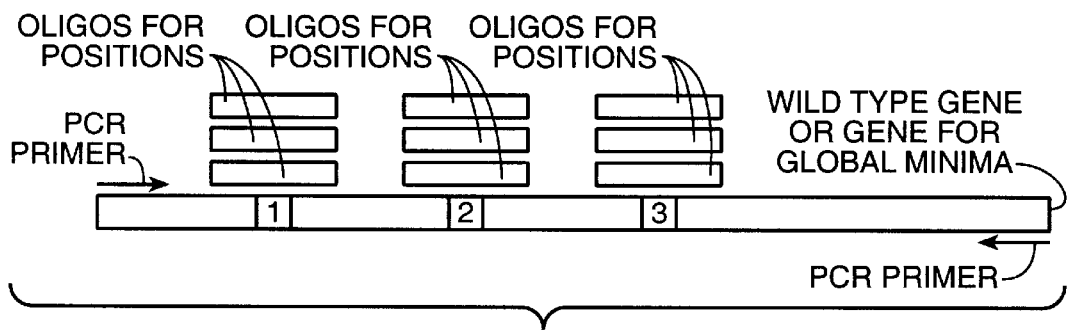
FIG._18

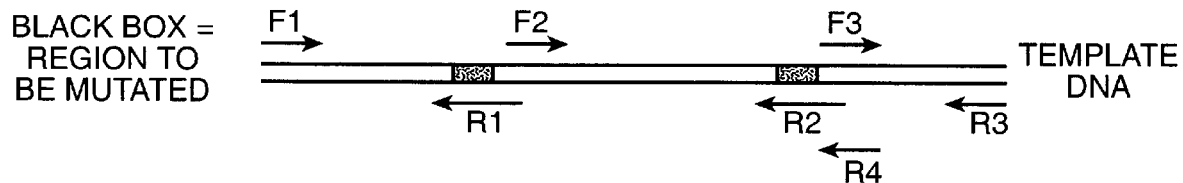
STEP 1: SET UP 3 PCR REACTIONS:
PRODUCTS:
TUBE 1: 
TUBE 2: 
TUBE 3: 
STEP 2: SET UP PCR REACTION WITH PRODUCTS OF TUBE 1 + PRODUCTS TUBE 2 + F1 + R4.
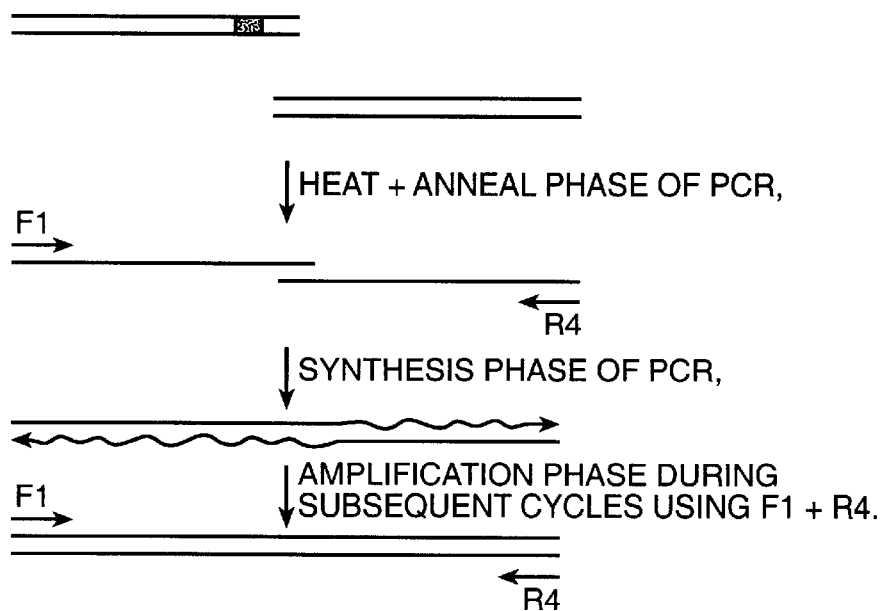
STEP 3: REPEAT STEP 2 USING PRODUCT FROM STEP 2 + PRODUCT FROM STEP 1, TUBE 3 + PRIMERS F1 + R3.
FIG. 19

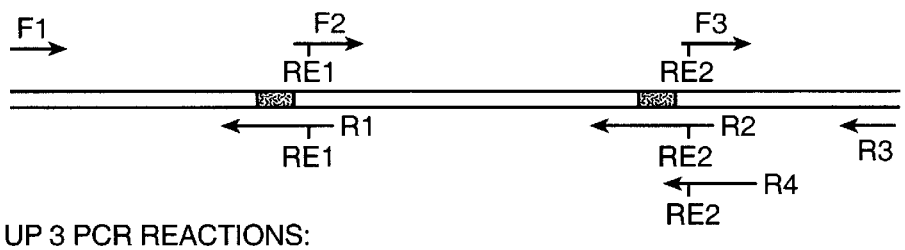

STEP 1: SET UP 3 PCR REACTIONS:

TUBE 1: 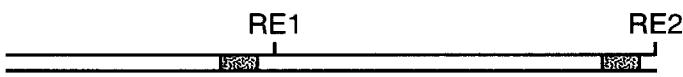

TUBE 2: 

TUBE 3: 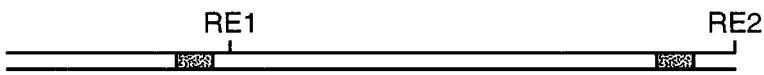

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 3.

STEP 7: AMPLIFY PRODUCT FROM STEP 6 WITH F1 + R3.

FIG._20

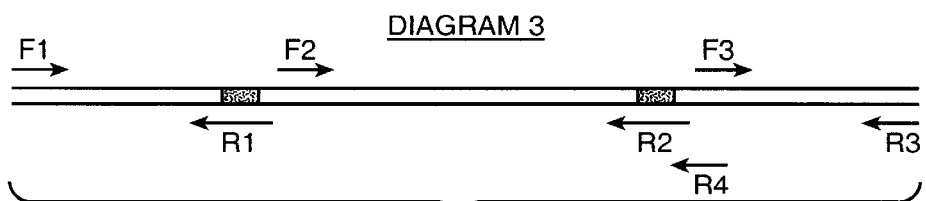

FIG._21

RECOMBINANT INTERFERON-BETA MUTEINS

This application is a continuing application of U.S. Ser. No. 60/133,785, filed May 12, 1999.

FIELD OF THE INVENTION

The invention relates to novel interferon-beta activity (IbA) proteins and nucleic acids. The invention further relates to the use of the IbA proteins in the treatment of interferon-beta (INF-β) related disorders.

BACKGROUND OF THE INVENTION

Human Interferons (IFNs) are members of a biologically potent family of cytokines. Originally, IFNs were identified as agents produced and secreted by virus-infected cells which can protect cells against further viral infections. However, in addition to this antiviral effect, IFNs can elicit many other changes in cellular behavior, including effects on cellular growth and differentiation and modulation of the immune system [e.g., see Lengyel, Annu. Rev. Biochem. 51:251–82 (1982); Gresser and Tovey, Biochim. Biophys. Acta 516(2):231–47 (1978); Gresser et al., Nature New Biol. 231(18):20–1 (1971); Dolei et al., J. Gen. Virol. 46(1) :227–36 (1980); Gresser, Cell Immunol 34(2):406–15 (1977)]. By virtue of their antigenic, biological and physico-chemical properties, IFNs are classified into three groups, INF-α (leukocyte), INF-β (fibroblast) and INF-γ (immune) [Stewart, J. Infect. Dis. 142(4):643 (1980)].

In humans, the IFN-α subtype encompass a multigene family of about 20 genes, encoding proteins of 166–172 amino acids that are all closely related. In contrast to this diversity, there is only one human interferon-beta (IFN-β) gene, also encoding a protein of 166 amino acids. IFN-β has low homology to the IFN-α family and is an N-linked glycoprotein [Knight, Proc. Natl. Acad. Sci. U.S.A. 73(2) :520–523 (1976)]. There is also only one human IFN-γ gene that encodes a polypeptde of 143 amino acids that is glycosylated and forms a dimer in its native state. IFN-γ shows only slight structural similarities to IFN-α or to IFN-β.

All IFN-α and IFN-β (also commonly referred to as type I interferon family) appear to bind to a common high affinity cell surface receptor, a 130 kD glycoprotein that is widely distributed on different cell types and that is distinct from the one bound by IFN-γ. Type-I interferons are recognized by a complex containing the receptor subunits ifnar1 and ifnar2 and their associated Janus tyrosine kinases, Tyk2 and Jak1, that activate the transcription factors STAT1 and STAT2, leading to the formation of the transcription factor complex ISGF3 [interferon-stimulated gene factor 3; Li et al., Biochemie 80(8–9):703–20 (1998); Nadeau et al., J. Biol. Chem. 274(7):4045–52 (1999)]. Three distinct modes of IFN/receptor complex interaction are known: (i) INF-α with ifnar1 and ifnar2; (ii) IFN-β with ifnar1 and ifnar2; and (iii) IFN-β with ifnar2 alone [Lewerenz et al., J. Mol. Biol. 282(3):585–99(1998)]. While Lewerenz et al. suggest that INF-α and IFN-β interact with their receptors in different ways and as such may also signal differently, the events responsible for biological activity beyond receptor binding are poorly understood.

As might be predicted for such a large family of cytokines with almost ubiquitously distributed receptors, IFNs display varied physiological roles. Production of IFN-α or IFN-β is induced by infection, including viral infection or the presence of foreign cell types and antigens. It is not clear what specific molecules are responsible for induction, but double-stranded RNA and cytokines can be good inducers. There is much overlap between different cell types in both the inducers and the species of IFN that is induced. The major cell types that produce IFNs are: lymphocytes, monocytes and macrophages (for IFN-α); fibroblasts and some epithelial cells and lymphoblastoid cells (for IFN-β); and activated T lymphocytes (for IFN-γ).

In addition to the 'classical' anti-viral activities that all IFNs elicit in their target cells, the biological consequences of IFN binding to its receptor can include inhibition of cell proliferation, induction of cell differentiation, changes in cell morphology, enhancement of histocompatibility antigen expression on many cells and stimulation of immunoglobulin-Fc receptor expression on macrophages. B lymphocytes can be induced to increase antibody production by low concentration of IFN-α or IFN-β. An additional effect of IFN-α and IFN-β is activation of natural killer cells that may be responsible for the destruction of virus-infected cells or tumor cells in vivo. Overall, IFNs seem to be of great importance as part of the body's defense against foreign organisms, foreign antigens and abnormal cell types (Clemens, in Cytokines, BIOS Scientific Publishers Limited, 1991; De Maeyer et al., in Interferons and Other Regulatory Cytokines, Wiley, New York, 1988).

INF-α and IFN-β were among the first of the cytokines to be produced by recombinant DNA technology. For example, the amino acid and nucleotide sequence of human IFN-β [Tanaguchi et al., Gene 10(1):11–15 (1980); Houghton et al., Nucleic Acids Res. 8(13):2885–94 (1980)] made it possible to produce recombinant human IFN-β in e.g., mammalian, insect, and yeast cells and in E. coli, that is free from viruses and other contaminants from human sources [e.g., Ohno and Taniguchi, Nucleic Acids Res. 10(3):967–77 (1982); Smith et al., Mol. Cell. Biol. 3(12):2156–65 (1983); Demolder et al., J. Biotechnol. 32(2):179–89 (1994); Dorin et al., U.S. Pat. No. 5,814,485 (1998); Konrad et al., U.S. Pat. No. 4,450,103 (1984)].

IFNs have been shown to have therapeutic value in conditions such as inflammatory, viral, and malignant diseases [e.g., see Desmyter et al., Lancet 2(7987):645–7 (1976); Makower and Wadler, Semin. Oncol. 26(6):663–71 (1999); Sturzebecher et al., J. Interferon Cytokine Res. 19(11):1257–64 (1999); Zein, Cytokines Cell. Mol. Ther. 4(4):229–41 (1998; Musch et al., Hepatogastroeneterology 45(24):2282–94 (1998); Wadler et al., Cancer J. Sci. Am. 4(5):331–7 (1998)]. IFN-β is a marketed drug (Betaseron, manufactured by Berlex and Avonex, manufactured by Biogen) that has been approved for use in treatment of multiple sclerosis (MS) [Arnason, Biomed Pharmacother 53(8):344–50, (1999); Comi et al., Mult. Scler. 1(6):317–20 (1996); Aappos, Lancet 353(9171):2242–3 (1999)]. IFN-β seems to reduce the number of attacks suffered by patients with relapsing and remitting MS. Betaseron, a recombinant IFN-β expressed in E. coli, consists of 165 amino acids (missing the initial methionine) and is genetically engineered so that it contains a serine at position 17, to replace a cysteine. It is a nonglycosylated form of IFN-β. Avonex is a human IFN-β, consisting of 166 amino acids that is produced by recombinant DNA techniques in CHO cells. This is a glycosylated form of IFN-β. Also, recent studies show promising IFN efficacy in treating certain viral diseases, such as Hepatitis B or C, and cancer.

Most cytokines, including IFN-β, have relatively short circulation half-lives since they are produced in vivo to act locally and transiently. To use IFN-β as an effective systemic therapeutic, one needs relatively large doses and frequent administrations. Frequent parenteral administrations are inconvenient and painful. Further, toxic side effects are associated with IFN-β administration which are so severe that some multiple sclerosis patents cannot tolerate the treatment. These side effects are probably associated with administration of a high dosage. In clinical studies it has been found that some patients produce antibodies to IFN-β, which neutralize its biological activity.

Furthermore, it has been observed that dimers and oligomers of microbially produced IFN-β are formed in *E. coli*, rendering purification and separation of IFN-β laborious and time consuming. It also necessitates several additional steps in purification and isolation procedures such as reducing the protein during purification and reoxidizing it to restore it to its original conformation, thereby increasing the possibility of incorrect disulfide bond formation. In addition, and most likely attributable to the above-listed shortcomings, microbially produced recombinant human IFN-β has also been found to exhibit consistently low specific activity. It would be desirable, therefore, to microbially produce a biologically active IFN-β protein that has a reduced or eliminated ability to form intermolecular crosslinks or intramolecular bonds that cause the protein to adopt an undesirable structure.

To this end, variants of IFN-β sequences, applications and production procedures are known; see for example U.S. Pat. Nos. 4,450,103; 4,518,584; 4,588,585; 4,737,462; 4,738,844; 4,738,845; 4,753,795; 4,769,233; 4,793,995; 4,914,033; 4,959,314; 5,183,746; 5,376,567; 5,545,723; 5,730,969; 5,814,485; 5,869,603 and references cited therein.

Recently, the crystal structures of recombinant murine INFβ [Senda et al., EMBO J. 11(9):3193–201 (1992); Mitsui et al., Pharmacol. Ther. 58(1):93–132 (1993); Senda et al., J. Mol. Biol. 253(1):187–207 (1995); Mitsui et al., J. Interferon Cytokine Res. 17(6):319–26 (1997); all of which are expressly incorporated by reference] and human INFβ [Karpusas et al., Proc. Natl. Acad. Sci. U.S.A. 94(22):11813–8 (1997); Runkel et al., Pharm. Res. 15(4):641–9 (1998); Runkel et a 273(14):8003–8 (1998); Lewerenz et al., J. Mol. Biol. 282(3):585–99 (1998); all of which are expressly incorporated by reference] have been solved. Karpusas et al. determined the crystal structure of glycosylated human IFN-β at 2.2 Angstrom resolution by molecular replacement. The molecule adopts a fold similar to that of the previously determined structures of murine IFN-β and human IFN-α2b, but displays several, distinct structural features. Like human IFN-α2b, INF-P contains a zinc-binding site at the interface of the two molecules in the asymmetric unit, however, unlike human IFN-α2b, IFN-β dimerizes with contact surfaces from opposite sides of the molecule. Runkel et al. reported structural and functional differences between glycosylated (IFN,β-1a) and non-glycosylated (IFN-β1b) forms of human IFN-β and suggested that the greater biological activity of INF-β-1a is due to the stabilizing effect of the carbohydrate moiety.

The available crystal structure of INFβ allows further protein design and the generation of more stable proteins or protein variants with an altered activity. Several groups have applied and experimentally tested systematic, quantitative methods to protein design with the goal of developing general design algorithms (Hellinga et al., J. Mol. Biol. 222: 763–785 (1991); Hurley et al., J. Mol. Biol. 224:1143–1154 (1992); Desjarlaisl et al., Protein Science 4:2006–2018 (1995); Harbury et al., Proc. Natl. Acad. Sci. U.S.A. 92:8408–8412 (1995); Klemba et al., Nat. Struc. Biol. 2:368–373 (1995); Nautiyal et al., Biochemistry 34:11645–11651 (1995); Betzo et al., Biochemistry 35:6955–6962 (1996); Dahiyat et al., Protein Science 5:895–903 (1996); Dahiyat et al., Science 278:82–87 (1997); Dahiyat et al., J. Mol. Biol. 273:789–96; Dahiyat et al., Protein Sci. 6:1333–1337 (1997); Jones, Protein Science 3:567–574 (1994); Konoi, et al., Proteins: Structure, Function and Genetics 19:244–255 (1994)). These algorithms consider the spatial positioning and steric complementarity of side chains by explicitly modeling the atoms of sequences under consideration. In particular, W098/47089, and U.S. Ser. No. 09/127,926 describe a system for protein design; both are expressly incorporated by reference.

A need still exists for proteins exhibiting both significant stability and interferon-beta activity. Accordingly, it is an object of the invention to provide interferon-beta activity (IbA) proteins, nucleic acids and antibodies for the treatment of multiple sclerosis, cancer and viral infections.

SUMMARY OF THE INVENTION

In accordance with the objects outlined above, the present invention provides non-naturally occurring interferon-beta activity (IbA) proteins (e.g. the proteins are not found in nature) comprising amino acid sequences that are less than about 97% identical to human INF-β. The IbA proteins have at least one altered biological property of an INF-β protein; for example, the IbA proteins will be more stable than IFN-β and bind to cells comprising an interferon receptor complex. Thus, the invention provides IbA proteins with amino acid sequences that have at least about 3–5 amino acid substitutions as compared to the INF-β sequence shown in FIG. 1 (SEQ ID NO:1).

In a further aspect, the present invention provides non-naturally occurring IbA conformers that have three dimensional backbone structures that substantially correspond to the three dimensional backbone structure of INFβ. In one aspect, the three dimensional backbone structure of the IbA conformer corresponds substantially to the three dimensional backbone structure of the A-chain of INFβ. In another aspect, the three dimensional backbone structure of the IbA conformer corresponds substantially to the three dimensional backbone structure of the B-chain of INF-β. The amino acid sequence of the IbA conformer and the amino acid sequence of INF-β are less than about 97% identical. In one aspect, at least about 90% of the non-identical amino acids are in a core region of the conformer. In other aspects, the conformer have at least about 100% of the non-identical amino acids are in a core region of the conformer.

In an additional aspect, the changes are selected from the amino acid residues at positions selected from positions 6, 13, 17, 21, 56, 59, 61, 62, 63, 66, 69, 84, 87, 91, 98, 102, 114, 118, 122, 129, 146, 150, 154, 157, 160, and 161. In a preferred aspect, the changes are selected from the amino acid residues at positions selected from positions 13, 17, 56, 59, 63, 66, 69, 84, 87, 91, 98, 114, 118, 122, 146, 157, and 161. In one aspect, the changes are selected from the amino acid residues at positions selected from positions 13, 17, 69, 84, 87, 91, 98, 118, 122, 146, 157, and 161. In another aspect, the changes are selected from the amino acid residues at positions selected from positions 13, 17, 56, 84, 87, 91, 114, 118, 122, and 161. Preferred embodiments include at least about 3–5 variations.

In a further aspect, the invention provides recombinant nucleic acids encoding the non-naturally occurring IbA proteins, expression vectors comprising the recombinant nucleic acids, and host cells comprising the recombinant nucleic acids and expression vectors.

In an additional aspect, the invention provides methods of producing the IbA proteins of the invention comprising culturing host cells comprising the recombinant nucleic acids under conditions suitable for expression of the nucleic acids. The proteins may optionally be recovered. In a further aspect, the invention provides pharmaceutical compositions comprising an IbA protein of the invention and a pharmaceutical carrier.

In an additional aspect, the invention provides methods for treating an INFβ responsive condition comprising administering an IbA protein of the invention to a patient. The INFβ condition includes multiple sclerosis, viral infection, or cancer.

BRIEF DESCRIPTION OF THE DRAWINGS

FIG. 1A (SEQ ID NO:1) depicts the amino acid sequence of the A-chain of human INFβ as used in the determination of the crystal structure [PDB and GenBank # 1AU1; Karpusas et al., Proc. Natl. Acad. Sci. U.S.A. 94(22):11813–8 (1997)] and secondary structure elements. Secondary structure element legend: H, alpha helix (4-helix); B, residue in isolated beta bridge; E, extended strand, participates in beta ladder; G, 310 helix (3-helix); I, pi helix (5-helix); T, hydrogen bonded turn; S, bend.

FIG. 1B (SEQ ID NO:1) depicts the amino acid sequences of the B-chain of human INF-β as used in the determination of the crystal structure (Karpusas et al., supra) and secondary structure elements.

FIG. 1C (SEQ ID NO:2) depicts the complete DNA sequence encoding wild type human INF-β (GenBank accession number NM_002176). The encoded sequence consists of the signaling sequence, MTNKCLLQIALLLCF-STTALS (SEQ ID NO:3), and the 166 amino acids that constitute the actual protein (see FIGS. 1A and 1B) (SEQ ID NO:1). The DNA sequence of 757 nucleotides includes this coding sequence and a non-translated region. Bases 1 to 63 encode the signaling sequence; bases 64 to 561 encode the actual IFN-β; bases 562 to 564 (TGA) are stop codon; and the rest is untranslated sequence.

FIG. 2 depicts the structure of wild type IFN-β. Presented is the A-chain from the PDB file 1AU1. The amino acid side chains indicated are those positions included in the PDA design of CORE 1.

FIG. 3 depicts the residues for both the A-chain and B-chain of INF-β selected for PDA. The individual sets are described in detail herein.

FIG. 4A depicts the mutation pattern of IFN-β A-chain core 1 sequences based on the analysis of the lowest 1000 protein sequences generated by Monte Carlo analysis of A-chain IFN-β core 1 sequences (only the amino acid residues of positions 6, 21, 55, 56, 59, 62, 63, 66, 69, 84, 87, 91, 98, 122, 129, 133, 146, 150, 157, and 160 are given). All values are given in %. For example, at position 87, the human INF-β amino acid is leucine (see FIG. 1) (SEQ ID NO:1); in IbA proteins, 78.7% of the top 1000 sequences had phenylalanine at this position, and only 18.4% of the sequences had leucine. Similarly, for position 84 (valine in human INFβ, isoleucine (40.5%) and leucine (39.4%) are preferred over valine (19.6%).

FIG. 4B (SEQ ID NO:4) depicts a preferred IbA sequence based on the PDA analysis of IFN-β A-chain core 1 sequence. Amino acid residues different from the human IFN-β (see FIG. 1) (SEQ ID NO:1) are shown in bold and are underlined.

FIG. 5A depicts the mutation pattern of IFN-β A-chain core 2 sequences based on the analysis of the lowest 1000 protein sequences generated by Monte Carlo analysis of A-chain IFN-β core 2 sequences (only the amino acid residues of positions 1, 6,10, 14, 17, 21, 38, 50, 55, 56, 58, 59, 61, 62, 63, 66, 69, 70, 81, 84, 87, 91, 94, 95, 98, 102, 115, 122, 125, 126, 129, 130, 133, 138, 144, 146, 147, 150, 151, 153, 154, 157, 159, 160, 161, 163, and 164 are given). All values are given in %. For example, at position 91, the human IFN-β amino acid is valine (see FIG. 1) (SEQ ID NO:1); in IbA proteins, 81.7% of the top 1000 sequences had isoleucine at this position, and only 11.5% of the sequences had valine. Similarly, for position 98 (leucine in human IFN-β), phenylalanine (68.8%) is preferred over leucine (31.2%).

FIG. 5B (SEQ ID NO:5) depicts a preferred IbA sequence based on the PDA analysis of IFN-β A-chain core 2 sequence. Amino acid residues different from the human IFN-β (see FIG. 1) (SEQ ID NO:1) are shown in bold and are underlined.

FIG. 6A depicts the mutation pattern of IFN-β A-chain core 3 sequences based on the analysis of the lowest 1000 protein sequences generated by Monte Carlo analysis of A-chain IFN-β core 3 sequences (only the amino acid residues of positions 1, 6, 10, 13, 14, 17, 18, 21, 38, 50, 55, 56, 58, 59, 61, 62, 63, 66, 69, 70, 72, 74, 76, 77, 81, 84, 87, 90, 91, 94, 95, 98, 102, 114, 115, 118, 122, 125, 126, 129, 130, 132, 133, 136, 138, 139, 142, 143, 144, 146, 147, 150, 151, 153, 154, 157, 159, 160, 161, 163, and 164 are given). All values are given in %. For example, at position 13, the human IFN-β amino acid is serine (see FIG. 1) (SEQ ID NO: 1); in IbA proteins, 67.7% of the top 1000 sequences had phenylalanine at this position and 31.4% of the sequences had tyrosine. None of the IbA sequences had serine at this position. Similarly, at position 118, the human IFN-β amino acid is serine (see FIG. 1) (SEQ ID NO:1); in IbA proteins, 89.1 % of the top 1000 sequences had alanine at this position and 10.9% of the sequences had tyrosine. None of the IbA sequences had serine at this position.

FIG. 6B (SEQ ID NO:6) depicts a preferred IbA sequence based on the PDA analysis of IFN-β A-chain core 3 sequence. Amino acid residues different from the human IFN-β (see FIG. 1) (SEQ ID NO:1) are shown in bold and are underlined.

FIG. 6C and FIG. 6D (SEQ ID NO:7–8) depict preferred IbA sequences based on the PDA analysis of IFN-β A-chain core 3 sequence, generated not only by the direct MC calculation following DEE, but also those after cleaning the MC list (C) and when running MC over the complete sequence space starting from the ground state generated by the direct MC calculation (D). Amino acid residues different from the human IFN-β (see FIG. 1) (SEQ ID NO:1) are shown in bold and are underlined.

FIG. 7A depicts the mutation pattern of IFN-β A-chain core 4 sequences based on the analysis of the lowest 1000 protein sequences generated by Monte Carlo analysis of A-chain IFN-β core 4 sequences. See FIG. 6A for details of figure legend. For example, at position 17, the human IFN-β amino acid is cysteine (see FIG. 1) (SEQ ID NO:1); in IbA proteins, 82.9% of the top 1000 sequences had aspartic acid at this position, 7.1% had threonine, 4.5% had alanine, 4.1% had leucine and 1.4% had valine. None of the IbA sequences had cysteine at this position.

FIG. 7B (SEQ ID NO:9) depicts a preferred IbA sequence based on the PDA analysis of IFN-β A-chain core 4 sequence. Amino acid residues different from the human IFN-β (see FIG. 1) (SEQ ID NO:1) are shown in bold and are underlined.

FIG. 7C and FIG. 7D (SEQ ID NOS:10–11) depict preferred IbA sequences based on the PDA analysis of IFN-β

A-chain core 4 sequence, generated not only by the direct MC calculation following DEE, but also those after cleaning the MC list (C) and when running MC over the complete sequence space starting from the ground state generated by the direct MC calculation (D). Amino acid residues different from the human IFN-β (see FIG. 1) (SEQ ID NO:1) are shown in bold and are underlined.

FIG. 8A depicts the mutation pattern of IFN-β A-chain core 5 sequences based on the analysis of the lowest 1000 protein sequences generated by Monte Carlo analysis of A-chain IFN-β core 5 sequences. See FIG. 6A for details of figure legend. For example, at position 84, the human IFN-β amino acid is valine (see FIG. 1) (SEQ ID NO:1); in IbA proteins, 99.5% of the top 1000 sequences had isoleucine at this position and 0.5% had leucine. None of the IbA sequences had valine at this position.

FIG. 8B (SEQ ID NO:12) depicts a preferred IbA sequence based on the PDA analysis of IFN-β A-chain core 5 sequence. Amino acid residues different from the human IFN-p (see FIG. 1) (SEQ ID NO:1) are shown in bold and are underlined.

FIG. 8C and FIG. 8D (SEQ ID NOS:13–14) depict preferred IbA sequences based on the PDA analysis of IFN-β A-chain core 5 sequence, generated not only by the direct MC calculation following DEE, but also those after cleaning the MC list (C) and when running MC over the complete sequence space starting from the ground state generated by the direct MC calculation (D). Amino acid residues different from the human IFN-β (see FIG. 1) (SEQ ID NO:1) are shown in bold and are underlined.

FIG. 9A depicts the mutation pattern of IFN-β A-chain core 6 sequences based on the analysis of the lowest 1000 protein sequences generated by Monte Carlo analysis of A-chain IFN-β core 6 sequences. See FIG. 6A for details of figure legend. For example, at position 118, the human IFN-β amino acid is serine (see FIG. 1) (SEQ ID NO:1); in IbA proteins, 100% of the top 1000 sequences had alanine. None of the IbA sequences had serine at this position.

FIG. 9B (SEQ ID NO:15) depicts a preferred IbA sequence based on the PDA analysis of IFN-β A-chain core 6 sequence. Amino acid residues different from the human IFN-β (see FIG. 1) (SEQ ID NO:1) are shown in bold and are underlined.

FIG. 9C and FIG. 9D (SEQ ID NOS:16–17) depict preferred IbA sequences based on the PDA analysis of IFN-β A-chain core 6 sequence, generated not only by the direct MC calculation following DEE, but also those after cleaning the MC list (C) and when running MC over the complete sequence space starting from the ground state generated by the direct MC calculation (D). Amino acid residues different from the human IFN-β (see FIG. 1) (SEQ ID NO:1) are shown in bold and are underlined.

FIG. 10A depicts the mutation pattern of IFN-β B-chain core 1 sequences based on the analysis of the lowest 1000 protein sequences generated by Monte Carlo analysis of B-chain IFN-β core 1 sequences (only the amino acid residues of positions 6, 21, 55, 56, 59, 62, 63, 66, 69, 84, 87, 91, 98, 122, 129, 133, 146, 150, 157, and 160 are given). All values are given in %. For example, at position 87, the human IFN-β amino acid is leucine (see FIG. 1) (SEQ ID NO:1); in IbA proteins, 74.6% of the top 1000 sequences had phenylalanine at this position, and only 21.5% of the sequences had leucine. Similarly, for position 84 (valine in human IFN-β), isoleucine (62.3%) is preferred over valine (25.4%).

FIG. 10B (SEQ ID NO:18) depicts a preferred IbA sequence based on the PDA analysis of IFN-β B-chain core 1 sequence. Amino acid residues different from the human IFN-β (see FIG. 1) SEQ ID NO:1) are shown in bold and are underlined.

FIG. 11A depicts the mutation pattern of IFN-β B-chain core 2 sequences based on the analysis of the lowest 1000 protein sequences generated by Monte Carlo analysis of B-chain IFN-β core 2 sequences (only the amino acid residues of positions 1, 6, 10, 14, 17, 21, 38, 50, 55, 56, 58, 59, 61, 62, 63, 66, 69, 70, 81, 84, 87, 91, 94, 95, 98, 102, 115, 122, 125, 126, 129, 130, 133, 138, 144, 146, 147, 150, 151, 153, 154, 157, 159, 160, 161, 163, and 164 are given). All values are given in %. For example, at position 56, the human IFN-β amino acid is alanine (see FIG. 1) (SEQ ID NO:1); in IbA proteins, 97.6% of the top 1000 sequences had leucine at this position, and only 2.4% of the sequences had alanine. Similarly, for position 91 (valine in human IFN-β), isoleucine (68.5%) and leucine (27.7%) are preferred over valine (3.8%).

FIG. 11B (SEQ ID NO:19) depicts a preferred IbA sequence based on the PDA analysis of IFN-β B-chain core 2 sequence. Amino acid residues different from the human IFN-β (see FIG. 1) (SEQ ID NO:1) are shown in bold and are underlined.

FIG. 12A depicts the mutation pattern of IFN-β B-chain core 3 sequences based on the analysis of the lowest 1000 protein sequences generated by Monte Carlo analysis of B-chain IFN-β core 3 sequences (only the amino acid residues of positions 1, 6, 10, 13, 14, 15, 17, 21, 38, 50, 55, 56, 58, 10 59, 61, 62, 63, 66, 69, 70, 72, 74, 76, 77, 81, 84, 87, 90, 91, 94, 95, 98, 102, 114, 115, 118, 122, 125, 126, 129, 130, 132, 133, 136, 138, 139, 142, 143, 144, 146, 147, 150, 151, 153, 154, 157, 159, 160, 161, 163, and 164 are given). All values are given in %. For example, at position 13, the human IFN-β amino acid is serine (see FIG. 1); in IbA proteins, 92.7% of the top 1000 sequences had leucine at this position and 7.3% of the sequences had alanine. None of the IbA sequences had serine at this position. Similarly, at position 118, the human IFN-β amino acid is serine (see FIG. 1) (SEQ ID NO:1); in IbA proteins, 100% of the top 1000 sequences had leucine at this position.

FIG. 12B (SEQ ID NO:20) depicts a preferred IbA sequence based on the PDA analysis of IFN-β B-chain core 3 sequence. Amino acid residues different from the human IFN-β (see FIG. 1) (SEQ ID NO:1) are shown in bold and are underlined.

FIG. 13A depicts the mutation pattern of IFN-β B-chain core 4 sequences based on the analysis of the lowest 1000 protein sequences generated by Monte Carlo analysis of B-chain IFN-β core 4 sequences. See FIG. 12A for details of figure legend. For example, at position 56, the human IFN-β amino acid is alanine (see FIG. 1) (SEQ ID NO:1); in IbA proteins, 97.7% of the top 1000 sequences had leucine at this position and only 2.3% had alanine. Similarly, at position 114, the human IFN-β amino acid is glycine (see FIG. 1) (SEQ ID NO:1); in IbA proteins, 100% of the top 1000 sequences had phenylalanine at this position.

FIG. 13B (SEQ ID NO:21) depicts a preferred IbA sequence based on the PDA analysis of IFN-β B-chain core 4 sequence. Amino acid residues different from the human IFN-β (see FIG. 1) (SEQ ID NO:1) are shown in bold and are underlined.

FIG. 14A depicts the mutation pattern of IFN-β B-chain core 5 sequences based on the analysis of the lowest 1000 protein sequences generated by Monte Carlo analysis of B-chain IFN-β core 5 sequences (only the amino acid residues of positions 1, 6, 10, 13, 14, 17, 18, 21, 38, 50, 55, 56, 58, 59, 61, 62, 63, 66, 69, 70, 72, 74, 76, 77, 81, 84, 87, 90, 91, 94, 95, 98, 102, 114, 115, 118, 122, 125, 126, 129, 130, 132, 133, 136, 138, 139, 142, 143, 144, 146, 147, 150, 151, 153, 154, 157, 159, 160, 161, 163, and 164 are given). For example, at position 56, the human IFN-β amino acid is alanine (see FIG. 1) (SEQ ID NO:1); in IbA proteins, 97.6% of the top 1000 sequences had leucine at this position and only 2.4% had alanine. Similarly, at position 114, the human IFN-β amino acid is glycine (see FIG. 1) (SEQ ID NO:1); in IbA proteins, 100% of the top 1000 sequences had leucine at this position.

FIG. 14B (SEQ ID NO:1) depicts a preferred IbA sequence based on the PDA analysis of IFN-β B-chain core 5 sequence. Amino acid residues different from the human IFN-β (see FIG. 1) (SEQ ID NO:1) are shown in bold and are underlined.

FIG. 15A depicts the mutation pattern of IFN-β B-chain core 6 sequences based on the analysis of the lowest 1000 protein sequences generated by Monte Carlo analysis of B-chain IFN-β core 6 sequences. See FIG. 14A for details of figure legend. For example, at position 118, the human IFN-β amino acid is serine (see FIG. 1) (SEQ ID NO:1); in IbA proteins, 99.4% of the top 1000 sequences had glutamic acid at this position and 0.6% had alanine. None of the IbA sequences had serine at this position. Similarly, for position 161 (threonine in human IFN-β), glutamic acid (86.4%) is preferred over threonine (12.1 %).

FIG. 15B (SEQ ID NO:23) depicts a preferred IbA sequence based on the PDA analysis of IFN-β B-chain core 6 sequence. Amino acid residues different from the human IFN-β (see FIG. 1) (SEQ ID NO:1) are shown in bold and are underlined.

FIG. 16A depicts the mutation pattern of IFN-β, B-chain core 7 sequences based on the analysis of the lowest 1000 protein sequences generated by Monte Carlo analysis of B-chain IFN-β core 7 sequences. See FIG. 14A for details of figure legend. For example, at position 17, the human IFN-β amino acid is cysteine (see FIG. 1) (SEQ ID NO:1); in IbA proteins, 32.8% of the top 1000 sequences had threonine at this position, 31 % had alanine, 29% had aspartic acid, 5% had glutamic acid, 1.4% had serine, and 0.8% had glycine. None of the IbA sequences had cysteine at this position.

FIG. 16B (SEQ ID NO:24) depicts a preferred IbA sequence based on the PDA analysis of IFN-β B-chain core 7 sequence. Amino acid residues different from the human IFN-β (see FIG. 1) (SEQ ID NO:1) are shown in bold and are underlined.

FIG. 17 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotdes results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 18 depicts a preferred scheme for synthesizing an IbA library of the invention. The wild type gene, or any starting gene, such as the gene for the global minima gene, can be used. Oligonucleotides comprising sequences that encode different amino acids at the different variant positions (indicated in the Figure by box 1, box 2, and box 3) can be used during PCR. Those primers can be used in combination with standard primers. This generally requires fewer oligonucleotides and can result in fewer errors.

FIG. 19 depicts an overlapping extension method. At the top of FIG. 19 is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. Thus, as shown in this example, oligos R1 and F2 comprise a region of homology and so do oligos R2 and F3. In this example, three separate PCR reactions are done for step 1. The first reaction contains the template plus oligos F1 and R1. The second reaction contains template plus oligos F2 and R2, and the third contains the template and oligos F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers, F1 and R4. In Step 3, the purified product from Step 2 is used in a third PCR reaction, together with the product of Step 1, tube 3 and the primers F1 and R3. The final product corresponds to the full length gene and contains the required mutations. Alternatively, Step 2 and Step 3 can be performed in one PCR reaction.

FIG. 20 depicts a ligation of PCR reaction products to synthesize the libraries of the invention. In this technique, the primers also contain an endonuclease restriction site (RE), either generating blunt ends, 5' overhanging ends or 3' overhanging ends. We set up three separate PCR reactions for Step 1. The first reaction contains the template plus oligos F1 and R1. The second reaction contains template plus oligos F2 and R2, and the third contains the template and oligos F3 and R3. The reaction products are shown. In Step 2, the products of Step 1 are purified and then digested with the appropriate restriction endonuclease. The digestion products from Step 2, tube 1 and Step 2, tube 2 are ligated together with DNA ligase (Step 3). The products are then amplified in Step 4 using oligos F1 and R4. The whole process is then repeated by digesting the amplified products, ligating them to the digested products of Step 2, tube 3, and then amplifying the final product using oligos F1 and R3. It would also be possible to ligate all three PCR products from Step 1 together in one reaction, providing the two restriction sites (RE1 and RE2) were different.

FIG. 21 depicts blunt end ligation of PCR products. In this technique, oligos such as F2 and R1 or R2 and F3 do not overlap, but they abut. Again three separate PCR reactions are performed. The products from tube 1 and tube 2 (see FIG. 20, Step 1) are ligated, and then amplified with outside primers F1 and R4. This product is then ligated with the product from Step 1, tube 3. The final products are then amplified with primers F1 and R3.

DETAILED DESCRIPTION OF THE INVENTION

The present invention is directed to novel proteins and nucleic acids possessing interferon-beta activity (sometimes referred to herein as "IbA proteins" and "IbA nucleic acids"). The proteins are generated using a system previously described in WO98/47089 and U.S. Ser. Nos. 09/058,459, 09/127,926, 60/104,612, 60/158,700, 09/419,351, 60/181,630, 60/186,904, and U.S patent application, entitled *Protein Design Automation For Protein Libraries* (Filed: Apr. 14, 2000; Inventor: Bassil Dahiyat), all of which are expressly incorporated by reference in their entirety, that is a computational modeling system that allows the generation of extremely stable proteins without necessarily disturbing the biological functions of the protein itself. In this way, novel IbA proteins and nucleic acids are generated, that can have a plurality of mutations in comparison to the wild-type enzyme yet retain significant activity.

Generally, there are a variety of computational methods that can be used to generate the IbA proteins of the invention. In a preferred embodiment, sequence based methods are used. Alternatively, structure based methods, such as PDA, described in detail below, are used.

Similarly, molecular dynamics calculations can be used to computationally screen sequences by individually calculating mutant sequence scores and compiling a rank ordered list.

In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(5016):164–70 (1991), incorporated by reference) and/or potentials of mean force (Hendlich et al., J. Mol. Biol. 216(1):167–180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1-8 (1998), hereby expressly incorporated by reference). Similarly, scoring functions can be used to screen for sequences that would create disulfide bonds in the protein. These potentials attempt to specifically modify a protein structure to introduce a new structural motif.

In a preferred embodiment, sequence and/or structural alignment programs can be used to generate the IbA proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

As is known in the art, there are a number of sequence alignment methodologies that can be used. For example, sequence homology based alignment methods can be used to create sequence alignments of proteins related to the target structure (Altschul et al., J. Mol. Biol. 215(3):403–410 (1990), Altschul et al., Nucleic Acids Res. 25:3389–3402 (1997), both incorporated by reference). These sequence alignments are then examined to determine the observed sequence variations. These sequence variations are tabulated to define a set of IbA proteins.

Sequence based alignments can be used in a variety of ways. For example, a number of related proteins can be aligned, as is known in the art, and the "variable" and "conserved" residues defined; that is, the residues that vary or remain identical between the family members can be defined. These results can be used to generate a probability table, as outlined below. Similarly, these sequence variations can be tabulated and a secondary library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused library of IbA proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) can be randomized, either using all or a subset of amino acids. Similarly, outlier residues, either positional outliers or side chain outliers, may be eliminated.

Similarly, structural alignment of structurally related proteins can be done to generate sequence alignments (Orengo et al., Structure 5(8):1093–108 (1997); Holm et al., Nucleic Acids Res. 26(1):316–9 (1998), both of which are incorporated by reference). These sequence alignments can then be examined to determine the observed sequence variations. Libraries can be generated by predicting secondary structure from sequence, and then selecting sequences that are compatible with the predicted secondary structure. There are a number of secondary structure prediction methods such as helix-coil transition theory (Munoz and Serrano, Biopolymers 41:495, 1997), neural networks, local structure alignment and others (e.g., see in Selbig et al., Bioinformatics 15:1039–46, 1999).

Similarly, as outlined above, other computational methods are known, including, but not limited to, sequence profiling [Bowie and Eisenberg, Science 253(5016):164–70, (1991)], rotamer library selections [Dahiyat and Mayo, Protein Sci. 5(5):895–903 (1996); Dahiyat and Mayo, Science 278(5335):82–7 (1997); Desjarlais and Handel, Protein Science 4:2006–2018 (1995); Harbury et Proc. Natl. Acad. Sci. U.S.A. 92(18):8408–8412 (1995); Kono et al., Proteins: Structure, Function and Genetics 19:244–255 (1994); Hellinga and Richards, Proc. Natl. Acad. Sci. U.S.A. 91:5803–5807 (1994)]; and residue pair potentials [Jones, Protein Science 3: 567–574, (1994)]; PROSA [Heindlich et al., J. Mol. Biol. 216:167–180 (1990)]; THREADER [Jones et al., Nature 358:86–89 (1992)], and other inverse folding methods such as those described by Simons et al. [Proteins, 34:535–543, (1999)], Levitt and Gerstein [Proc. Natl. Acad. Sci. U.S.A., 95:5913–5920, (1998)], Godzik and Skolnick [Proc. Natl. Acad. Sci. U.S.A., 89:12098–102, (1992)], Godzik et al. [J. Mol. Biol. 227:227–38, (1992)], and other profile methods [Gribskov et al. Proc. Natl. Acad. Sci. U.S.A. 84:4355–4358 (1987) and Fischer and Eisenberg, Protein Sci. 5:947–955 (1996), Rice and Eisenberg J. Mol. Biol. 267:1026–1038(1997)], all of which are expressly incorporated by reference. In addition, other computational methods such as those described by Koehl and Levitt (J. Mol. Biol. 293:1161–1181 (1999); J. Mol. Biol. 293:1183–1193 (1999); expressly incorporated by reference) can be used to create a protein sequence library which can optionally then be used to generate a smaller secondary library for use in experimental screening for improved properties and function. In addition, there are computational methods based on forcefield calculations such as SCMF that can be used as well for SCMF, see Delarue et al. Pac. Symp. Biocomput. 109–21 (1997); Koehl et al., J. Mol. Biol. 239:249–75 (1994); Koehl et al., Nat. Struct. Biol. 2:163–70 (1995); Koehl et al., Curr. Opin. Struct. Biol. 6:222–6 (1996); Koehl et al., J. Biol. 293:1183–93 (1999); Koehl et al., J. Mol. Biol. 293:1161–81 (1999); Lee J., Mol. Biol.236:918–39 (1994); and Vasquez Biopolymers 36:53–70 (1995); all of which are expressly incorporated by reference. Other forcefield calculations that can be used to optimize the conformation of a sequence within a computational method, or to generate de novo optimized sequences as outlined herein include, but are not limited to, OPLS-AA [Jorgensen et al., J. Am. Chem. Soc. 118:11225–11236 (1996); Jorgensen, W. L.; BOSS, Version 4.1; Yale University: New Haven, CT (1999)]; OPLS [Jorgensen et al., J. Am. Chem. Soc.110:1657ff (1988); Jorgensen et al., J. Am. Chem. Soc.112:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A. 96:5482–5485 (1999)]; ECEPP/3 [Liwo et al., J Protein Chem. 13(4):375–80 (1994)]; AMBER 1.1 force field (Weiner et a Am. Chem. Soc. 106:765–784); AMBER 3.0 force field [U. C. Singh et al., Proc. Natl. Acad. Sci. U.S.A. 82:755–759 (1985)]; CHARMM and CHARMM22 (Brooks et al., J. Comp. Chem. 4:187–217); cvff3.0 [Dauber-Osguthorpe et al., Proteins: Structure, Function and Genetics, 4:31–47 (1988)]; cff99:1 (Maple et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference. In fact, as is outlined below, these forcefield methods may be used to generate the secondary library directly; that is, no primary library is generated; rather, these methods can be used to generate a probability table from which the secondary library is directly generated.

In a preferred embodiment, the computational method used to generate the primary library is Protein Design Automation (PDA), as is described in U.S. Ser. Nos. 60/061,097, 60/043,464, 60/054,678, 09/127,926, 60/104,612, 60/158,700, 09/419,351, 60/181,630, 60/186,904, U.S patent application, entitled Protein Design Automation For Protein Libraries (Filed: Apr. 14, 2000; Inventor: Bassil Dahiyat) and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Similarly, for all the sampling techniques, the acceptance criteria of whether a sampling jump is accepted can be altered.

As outlined in U.S. Ser. No. 09/127,926, the protein backbone (comprising (for a naturally occuring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization [Mayo et al., J. Phys. Chem. 94:8897 (1990)] of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occuring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in their amino acid identity and a single rotamer conformation, or "floated", which only fixes the identity but not the rotamer conformation.

Similarly, residues which may be chosen as variable residues may be those that confer undesirable biological attributes, such as susceptibility to proteolytic degradation, dimerization or aggregation sites, glycosylabon sites which may lead to immune responses, unwanted binding activity, unwanted allostery, undesirable enzyme activity but with a preservation of binding, etc.

In a preferred embodiment, each variable position is classified as either a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modelling. Alternatively, a preferred embodiment utilizes an assessment of the orientation of the C$\alpha$-C$\beta$ vectors relative to a solvent accessible surface computed using only the template C$\alpha$ atoms, as outlined in U.S. Ser. Nos. 60/061,097, 60/043,464, 60/054,678, 09/127,926 60/104,612, 60/158,700, 09/419,351, 60/181,630, 60/186,904, U.S patent application, entitled *Protein Design Automation For Protein Libraries* (Filed: Apr. 14, 2000; Inventor: Bassil Dahiyat) and PCT US98/07254. Alternatively, a surface area calculation can be done.

Suitable core and boundary positions for IbA proteins are outlined below.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the a scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occuring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multmerize, or have ligand binding sites, may contain hydrophobic surface residues, etc. In addition, residues that do not allow helix "capping" or the favorable interaction with an a-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127, 926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec} \quad \text{Equation 1}$$

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926, 60/104,612, 60/158,700, 09/419, 351, 60/181,630, 60/186,904, U.S patent application, entitled *Protein Design Automation For Protein Libraries* (Filed: Apr. 14, 2000; Inventor: Bassil Dahiyat) and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered. The term "portion", or similar grammatical equivalents thereof, as used herein, with regard to a protein refers to a fragment of that protein. This fragment may range in size from 5–10 amino acid residues to the entire amino acid sequence minus one amino acid. Accordingly, the term "portion", as used herein, with regard to a nucleic refers to a fragment of that nucleic acid. This fragment may range in size from 6–10 nucleotides to the entire nucleic acid sequence minus one nucleotide.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

In addition, as will be appreciated by those in the art, a variety of force fields that can be used in the PDA calculations can be used, including, but not limited to, Dreiding I and Dreiding II [Mayo et al, J. Phys. Chem. 94:8897 (1990)], AMBER [Weiner et al., J. Amer. Chem. Soc. 106:765 (1984) and Weiner et al., J. Comp. Chem. 106:230 (1986)], MM2 [Allinger, J. Chem. Soc. 99:8127 (1977), Liljefors et al., J. Com. Chem. 8:1051 (1987)]; MMP2 [Sprague et al., J. Comp. Chem. 8:581 (1987)]; CHARMM [Brooks et al., J. Comp. Chem. 106:187 (1983)]; GROMOS; and MM3 [Allinger et al., J. Amer. Chem. Soc. 111:8551 (1989)], OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc.110:1657ff (1988); Jorgensen et al., J Am. Chem. Soc. 112:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A 96:5482–5485 (1999)]; ECEPP/3 [Liwo et al., J Protein Chem. 13(4):375–80 (1994)]; A field (Weiner, et al., J. Am. Chem. Soc. 106:765–784); AMBER 3.0 force field (U.C. Singh et al., Proc. Natl. Acad. Sci. U.S.A. 82:755–759); CHARMM and CHARMM22 (Brooks et al., J. Comp. Chem. 4:187–217); cvff3.0 [Dauber-Osguthorpe, et al., Proteins: Structure, Function and Genetics, 4:31–47 (1988)]; cff91 (Maple, et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Ser. No. 09/127,926 and PCT US98/07254, preferred embodiments utilize a Dead End Elimination (DEE) step, and preferably a Monte Carlo step.

PDA, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild-type or homolog residues may be used. Similarly, the entire protein or a fragment of it may be biased; for example, the active site may be biased towards wild-type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompabbility Complex) can be used to rescore a library in order to eliminate proteins containing sequences which can potentially bind to MHC, i.e. potentially immunogenic sequences.

In a preferred embodiment, a variety of filtering techniques can be done, including, but not limited to, DEE and its related counterparts. Additional filtering techniques include, but are not limited to branch-and-bound techniques for finding optimal sequences (Gordon and Mayo, Structure Fold. Des. 7:1089–98, 1999), and exhaustive enumeration of sequences.

As will be appreciated by those in the art, once an optimized sequence or set of sequences is generated, a variety of sequence space sampling methods can be done, either in addition to the preferred Monte Carlo methods, or instead of a Monte Carlo search. That is, once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example, etc.). Jumps where multiple residue positions are coupled (two residues always change together, or never change together), jumps where whole sets of residues change to other sequences (e.g., recombination). Similarly, for all the sampling techniques, the acceptance criteria of whether a sampling jump is accepted can be altered.

In addition, it should be noted that the preferred methods of the invention result in a rank ordered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzman sampling is done. As will be appreciated by those in the art, the temperature criteria for Boltzman sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artifical Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps can occur with different crossover positions and more than one recombination at a time, and can involve recombination of two or more sequences. Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. [Science, 220:671–680 (1983)]. Simulated annealing alters the cutoff for accepting good or bad jumps by altering the temperature. That is, the stringency of the cutoff is altered by altering the temperature. This allows broad searches at high temperature to new areas of sequence space, altering with narrow searches at low temperature to explore regions in detail.

In addition, as outlined below, these sampling methods can be used to further process a first set to generate additional sets of IbA proteins.

The computational processing results in a set of optimized IbA protein sequences. These optimized IbA protein sequences are generally significantly different from the wild-type IFN-β sequence from which the backbone was taken. That is, each optimized IbA protein sequence preferably comprises at least about 3–10% variant amino acids from the starting or wild type sequence, with at least about 10–15% being preferred, with at least about 15–20% changes being more preferred and at least 25% being particularly preferred.

In a preferred embodiment, the IbA proteins of the invention have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different residues from the human IFN-β sequence.

Thus, in the broadest sense, the present invention is directed to IbA proteins that have IFN-β activity. By "IFN-β activity" or "IbA" herein is meant that the IbA protein exhibits at least one, and preferably more, of the biological functions of an IFN-β, as defined below. In one embodiment, the biological function of an IbA protein is altered, preferably improved, over the corresponding biological activity of an IFN-β.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20:9367–71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes amino acid residues such as proline and hydroxyproline. In addition, any amino acid representing a component of the IbA proteins can be replaced by the same amino acid but of the opposite chirality. Thus, any amino acid naturally occurring in the L-conflguration (which may also be referred to as the R or S, depending upon the structure of the chemical entity) may be replaced with an amino acid of the same chemical structural type, but of the opposite chirality, generally referred to as the D- amino acid but which can additionally be referred to as the R- or the S-, depending upon its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Left 428:(1–2) 68–70 May 22, 1998 and Tang et al., Abstr. Pap Am. Chem. S218:U138-U138 Part 2 Aug. 22, 1999, both of which are expressly incorporated by reference herein.

Additionally, modified amino acids or chemical derivatives of amino acids of consensus or fragments of IbA proteins, according to the present invention may be provided, which polypeptides contain additional chemical moieties or modified amino acids not normally a part of the protein. Covalent and non-covalent modifications of the protein are thus included within the scope of the present invention.

Such modifications may be introduced into an IbA polypeptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)alanine, (phosphono) glycine, (phosphono)leucine, (phosphono)isoleucine, (phosphono)threonine, or (phosphono)senne; or sulfated (e.g., —$SO_3H$) threonine, serine, tyrosine.

Other substitutions may include unnatural hyroxylated amino acids that may be made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Preferred alkyl groups herein contain 1 to 12 carbon atoms. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, and nitrogen being preferred. Alkyl includes substituted alkyl groups. By "substituted alkyl group" herein is meant an alkyl group further comprising one or more substitution moieties. A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—$NH_2R$), secondary (—NHR), or tertiary (—$NR_3$). Basic amino acids may be substituted with alkyl groups at any position of the naturally occurring amino acids lysine, arginine, ornithine, citrulline, or (guanidino)-acetic acid, or other (guanidino) alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the IbA polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of IbA polypeptides of the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatzed by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The IFN-β may be from any number of organisms, with IFN-β s from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans (this is sometimes referred to herein as hIFN-β, the sequence of which is depicted in FIG. 1). As will be appreciated by those in the art, IFN-β s based on IFN-β s from mammals other than humans may find use in animal models of human disease. The GenBank accession numbers for a variety of mammalian IFN-β species is as follows: bovine 69689, 124465 (IFN-β-1 precursor), 69688, 124467 (IFN-β-3 precursor), 69687, 124466 (IFN-β-2 precursor); dog 442673; sheep 310382; cat CAA69853, 1754718; pig 2411469, 164517; mouse 69686, 6754304, 51551, 124470, 494203; rat 7438651, 2497434, 1616939; Macaca fascicularis 3766295; horse 69685, 124468, 164229; human 69684, 124469, 4504603, 3318961, 3318960.

The IbA proteins of the invention exhibit at least one biological function of an IFN-β. By "interferon-beta" or "IFN-β" herein is meant a wild type IFN-β or an allelic variant thereof. Thus, IFN-β refers to all forms of IFN-β that are active in accepted IFN-β assays.

The IbA proteins of the invention exhibit at least one biological function of an IFN-β. By "biological function" or "biological property" herein is meant any one of the properties or functions of an IFN-β, including, but not limited to, the ability to effect cellular growth, in particular inhibition of cell proliferation; the ability to effect cellular differentiation, in particular induction of cell differentiation; the ability to induce changes in cell morphology; the ability to modulate the immune system; the ability to enhance histocompafibility antigen expression; the ability to stimulate immunoglobulin-Fc receptor expression on macrophages; the ability to induce antibody production in B lymphocytes, the ability to activate natural killer cells; the ability to bind to an IFN receptor; the ability to bind to a cell comprising an IFN receptor, the ability to treat multiple sclerosis; the ability to treat idiopathic pulmonary fibrosis; the ability to treat inflammatory diseases; the ability to treat viral diseases, including treatment of infections caused by papilloma viruses, such as genital warts and condylomata of the uterine cervix; hepatitis viruses, such as acute/chronic hepatitis B and non-A, non-B hepatitis (hepatitis C); herpes viruses, such as herpes genitalis, herpes zoster, herpes keratitis, and herpes simplex; viral encephalitis; cytomegalovirus pneumonia; and prophylaxis of rhinovirus; the ability to treat cancer, including treatment of several malignant diseases such as osteosarcoma, basal cell carcinoma, cervical dysplasia, glioma, acute myeloid leukemia, multiple myeloma, Hodgkin's disease, melanoma, renal cancer, liver cancer, and breast cancer.

All of these IbA proteins will exhibit at least 50% of the receptor binding or biological activity as the wild type IFN-β. More preferred are IbA proteins that exhibit at least 75%, even more preferred are IbA proteins that exhibit at least 90%, and most preferred are IbA proteins that exhibit more than 100% of the receptor binding or biological activity as the wild type IFN-β. Biological assays, receptor binding assays, anti-viral and anti-proliferation assays are described in U.S. patents 4,450,103; 4,518,584; 4,588,585; 4,737,462; 4,738,844; 4,738,845; 4,753,795; 4,769,233; 4,793,995; 4,914,033; 4,959,314; 5,183,746; 5,376,567; 5,545,723; 5,730,969; 5,814,485; 5,869,603 and in e.g., Anderson et al., J. Biol. Chem. 257(19):11301–4 (1982); Herberman et al., Nature 277(5693):221–3 (1979); Williams et al., Nature 282(5739):582–6 (1979); Branca and Baglioni, Nature 294(5843):768–70 (1981); Proc. Natl. Acad. Sci. U.S.A. 81(18):5662–6 (1984); Fellous et al., Proc. Natl. Acad. Sci. U.S.A. 79(10):3082–6 (1982); and Runkel et al., J. Biol. Chem. 273(14):8003–8 (1998), all of which are expressly incorporated by reference.

In one embodiment, at least one biological property of the IbA protein is altered when compared to the same property of IFN-β. As outlined above, the invention provides IbA nucleic acids encoding IbA polypeptides. The IbA polypeptide preferably has at least one property, which is substantially different from the same property of the corresponding naturally occurring IFN-β polypeptide. The property of the IbA polypeptide is the result the PDA analysis of the present invention.

The term "altered property" or grammatical equivalents thereof in the context of a polypeptide, as used herein, refer to any characteristic or attribute of a polypeptide that can be selected or detected and compared to the corresponding property of a naturally occurring protein. These properties include, but are not limited to oxidative stability, substrate specificity, substrate binding or catalytic activity, thermal stability, alkaline stability, pH activity profile, resistance to proteolytic degradation, Km, kcat, Km/kcat ratio, kinetic association ($K_{on}$) and dissociation ($K_{off}$) rate, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylabon or glycosylation, ability to treat disease.

Unless otherwise specified, a substantial change in any of the above-listed properties, when comparing the property of an IbA polypeptide to the property of a naturally occurring IFN-β protein is preferably at least a 20%, more preferably, 50%, more preferably at least a 2-fold increase or decrease.

A change in oxidative stability is evidenced by at least about 20%, more preferably at least 50% increase of activity of an IbA protein when exposed to various oxidizing conditions as compared to that of IFN-β. Oxidative stability is measured by known procedures.

A change in alkaline stability is evidenced by at least about a 5% or greater increase or decrease (preferably increase) in the half life of the activity of an IbA protein when exposed to increasing or decreasing pH conditions as compared to that of IFN-β. Generally, alkaline stability is measured by known procedures.

A change in thermal stability is evidenced by at least about a 5% or greater increase or decrease (preferably increase) in the half life of the activity of an IbA protein when exposed to a relatively high temperature and neutral pH as compared to that of IFN-β. Generally, thermal stability is measured by known procedures.

Similarly, IbA proteins, for example are experimentally tested and validated in in vivo and in in vitro assays. Suitable assays include, but are not limited to, e.g., examining their binding affinity to natural occurring or variant receptors and to high affinity agonists and/or antagonists. In addition to cell-free biochemical affinity tests, quantitative comparison are made comparing kinetic and equilibrium binding constants for the natural receptor to the naturally occurring IFN-β and to the IbA proteins. The kinetic association rate ($K_{on}$) and dissociation rate ($K_{off}$), and the equilibrium binding constants ($K_d$) can be determined using surface plasmon resonance on a BlAcore instrument following the standard procedure in the literature [Pearce et al., Biochemistry 38:81–89 (1999)]. Comparing the binding constant between a natural receptor and its corresponding naturally occurring IFN-β with the binding constant of a natural occurring receptor and an IbA protein are made in order to evaluate the sensitivity and specificity of the IbA protein. Preferably, binding affinity of the IbA protein to natural receptors and agonists increases relative to the naturally occurring IFN-β, while antagonist affinity decreases. IbA proteins with higher affinity to antagonists relative to the IFN-β may also be generated by the methods of the invention.

As described above, one biological function of an IbA protein is the ability of the IbA protein to bind to cells comprising an interferon receptor.

In a preferred embodiment, the assay system used to determine IbA is an in vitro system using cells that either express endogenous interferon receptors or cells stably transfected with the gene encoding the human interferon receptor. In this system, cell proliferation is measured as a function of BrdU incorporation, which is incorporated into the nucleic acid of proliferating cells. A decrease above background of at least about 10%, with at least about 20% being preferred, with at least about 30% being more preferred and at least about 50%, 75% and 90% being especially preferred is an indication of IbA.

In a preferred embodiment, the antigenic profile in the host animal of the IbA protein is similar, and preferably identical, to the antigenic profile of the host IFN-β; that is, the IbA protein does not significantly stimulate the host organism (e.g. the patient) to an immune response; that is, any immune response is not clinically relevant and there is no allergic response or neutralization of the protein by an antibody. That is, in a preferred embodiment, the IbA protein does not contain additional or different epitopes from the IFN-β. By "epitope" or "determinant" herein is meant a portion of a protein which will generate and/or bind an antibody. Thus, in most instances, no significant amount of antibodies are generated to a IbA protein. In general, this is accomplished by not significantly altering surface residues, as outlined below nor by adding any amino acid residues on the surface which can become glycosylated, as novel glycosylation can result in an immune response.

The IbA proteins and nucleic acids of the invention are distinguishable from naturally occurring IFN-ps. By "naturally occurring" or "wild type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, herein is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention. Representative amino acid and nucleotide sequences of a naturally occurring human IFN-β are shown in FIG. 1. It should be noted that unless otherwise stated, all positional numbering of IbA proteins and IbA nucleic acids is based on these sequences. That is, as will be appreciated by those in the art, an alignment of IFN-β proteins and IbA proteins can be done using standard programs, as is outlined below, with the identification of "equivalent" positions between the two proteins. Thus, the IbA proteins and nucleic acids of the invention are non-naturally occurring; that is, they do not exist in nature.

Thus, in a preferred embodiment, the IbA protein has an amino acid sequence that differs from a wild-type IFN-β sequence by at least 3% of the residues. That is, the IbA proteins of the invention are less than about 97% identical to an IFN-β amino acid sequence. Accordingly, a protein is an "IbA protein" if the overall homology of the protein sequence to the amino acid sequence shown in FIG. 1A or FIG. 1B (SEQ ID NO:1) is preferably less than about 97%, more preferably less than about 95%, even more preferably less than about 90% and most preferably less than 85%. In some embodiments the homology will be as low as about 75 to 80%. Stated differently, based on the human IFN-β sequence of 166 residues (see FIG. 1A) (SEQ ID NO:1), IbA proteins have at least about 5 residues that differ from the human IFN-β sequence (3%), with IbA proteins having from 5 residues to upwards of 62 residues being different from the human IFN-β sequence. Preferred IbA proteins have 5–30 different residues with from about 5 to about 15 being particularly preferred (that is, 3–9% of the protein is not identical to human IFN-β).

In another preferred embodiment, IbA proteins have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different residues from the human IFN-β sequence.

Homology in this context means sequence similarity or identity, with identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Dooliftle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403–410, (1990); Altschul et al., Nucleic Acids Res. 25:3389–3402 (1997); and Karlin et al., Proc. Natl. Acad. Sci. U.S.A. 90:5873–5787 (1993). A particularly useful BLAST program is the WU-BLAST-2 program which was obtained from Altschul et al., Methods in Enzymology, 266:460–480 (1996); http:flblast.wustl/edu/blastt README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucl. Acids Res., 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleofide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1, it is understood that in one embodiment, the percentage of sequence identity will be determined based on the number of identical amino acids in relation to the total number of amino acids. Thus, for example, sequence identity of sequences shorter than that shown in FIG. 1, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, IbA proteins of the present invention may be shorter or longer than the amino acid sequence shown in FIG. 1A (SEQ ID NO:1). Thus, in a preferred embodiment, included within the definition of IbA proteins are portions or fragments of the sequences depicted herein. Fragments of IbA proteins are considered IbA proteins if a) they share at least one antigenic epitope; b) have at least the indicated homology; c) and preferably have IbA biological activity as defined herein.

In a preferred embodiment, as is more fully outlined below, the IbA proteins include further amino acid variations, as compared to a wild type IFN-β, than those outlined herein. In addition, as outlined herein, any of the variations depicted herein may be combined in any way to form additional novel IbA proteins.

In addition, IbA proteins can be made that are longer than those depicted in the figures, for example, by the addition of epitope or purification tags, as outlined herein, the addition of other fusion sequences, etc. For example, the IbA proteins of the invention may be fused to other therapeutic proteins such as IL-11 or to other proteins such as Fc or serum albumin for pharmacokinetic purposes. See for example U.S. Pat. No. 5,766,883 and 5,876,969, both of which are expressly incorporated by reference.

In a preferred embodiment, the IbA proteins comprise variable residues in core residues.

Human IFN-β core residues are as follows: positions 1, 6, 10, 13, 14, 15, 17, 18, 21, 38, 50, 55, 56, 58, 59, 61, 62, 63, 66, 69, 70, 72, 74, 76, 77, 81, 84, 87, 90, 91, 94, 95, 98, 102, 114, 115, 118, 122, 125, 126, 129, 130, 132, 133, 136, 138, 139, 142, 143, 144, 146, 147, 150, 151, 153, 154, 157, 159, 160, 161, 163, and 164 (see FIG. 3). Accordingly, in a preferred embodiment, IbA proteins have variable positions selected from these positions.

The structure of human IFN-β as reported by Karpasus et al. (supra) indicated that IFN-β forms a dimer consisting of an A-chain and a B-chain.

Thus, in one embodiment, variable residues for the A-chain are as follows: positions 1, 6, 10, 13, 14, 17, 18, 21, 38, 50, 55, 56, 58, 59, 61, 62, 63, 66, 69, 70, 72, 74, 76, 77, 81, 84, 87, 90, 91, 94, 95, 98, 102, 114, 115, 118, 122, 125, 126, 129, 130, 132, 133, 136, 138, 139, 142, 143, 144, 146, 147, 150, 151, 153, 154, 157, 159, 160, 161, 163, and 164 (see FIG. 3). Accordingly, in a preferred embodiment, IbA proteins have variable positions selected from these positions.

Thus, in another embodiment, variable residues for the B-chain are as follows: positions 1, 6, 10, 13, 14, 15, 17, 18, 21, 38, 50, 55, 56, 58, 59, 61, 62, 63, 66, 69, 70, 72, 74, 76, 77, 81, 84, 87, 90, 91, 94, 95, 98, 102, 114, 115, 118, 122, 125, 126, 129, 130, 132, 133, 136, 138, 139, 142, 143, 144, 146, 147, 150, 151, 153, 154, 157, 159, 160, 161, 163, and 164 (see FIG. 3). Accordingly, in a preferred embodiment, IbA proteins have variable positions selected from these positions.

In a preferred embodiment, IbA proteins have variable positions selected solely from core residues of human IFN-β. Alternatively, at least a majority (51%) of the variable positions are selected from core residues, with at least about 75% of the variable positions being preferably selected from core residue positions, and at least about 90% of the variable positions being particularly preferred. A specifically preferred embodiment has only core variable positions altered as compared to human IFN-β.

Particularly preferred embodiments where IbA proteins have variable core positions as compared to human IFN-β are shown in the Figures.

In one embodiment, the variable core positions are altered to any of the other 19 amino acids. In a preferred embodiment, the variable core residues are chosen from Ala, Val, Phe, Ile, Leu, Tyr, Trp and Met. In another preferred embodiment, the variable core residues are chosen from Ala, Val, Leu, Ile, Phe, Tyr, and Trp. In another preferred embodiment, the variable core residues are chosen from Ala, Val, Ieu, Ile, and Gly. In another preferred embodiment, the variable core residues are chosen from Ala, Gly, Ser, Thr, Glu, Asp, Gln, Asn, and Cys.

In a preferred embodiment, the IbA protein of the invention has a sequence that differs from a wild-type human IFN-β protein in at least one amino acid position selected from positions 6, 13, 17, 21, 56, 30 59, 61, 62, 63, 66, 69, 84, 87, 91, 98, 102, 114, 118, 122, 129, 146, 150, 154, 157, 160, and 161; see also FIG. 3, which outlines sets of amino acid positions.

Preferred amino acids for each position, including the human IFN-β residues, are shown in FIGS. 4–16 (SEQ ID NOS:4–24). Thus, for example, for the A-chain of an IbA protein, at position 13, preferred amino acids are Phe, Tyr, Glu, and Ala; at position 17, a preferred amino acid is Asp; at position 69, a preferred amino acid is Val; at position 84 a preferred amino acid is lie; at position 87, a preferred amino acid is Phe; at position 91, a preferred amino acid is lie; at position 98, a preferred amino acid is Phe; at position 118, preferred amino acids are Ala, Val, and Cys; at position 122, preferred amino acids are Ile and Val; at position 146, a preferred amino acid is Ile; at position 157, a preferred amino acid is Leu; and at position 161, preferred amino acids are Ala and Cys.

For the B-chain of an IbA protein, at position13, preferred amino acids are Leu and Glu; at position 17, preferred amino acid are Ala and Thr; at position 56, a preferred amino acid is Leu; at position 63, a preferred amino acid is Phe; at position 84 a preferred amino acid is lie; at position 87, a preferred amino acid is Phe; at position 91, a preferred amino acid is Ile; at position 114, preferred amino acids are Phe and Leu; at position 118, preferred amino acids are Leu and Glu; at position 122, preferred amino acids are Ile and Phe; and at position 161, preferred amino acids are Ala and Glu. Preferred changes are as follows: L6A; L6F; S13F; S13Y; S13L; S13I; S13A; S13G; S13G; S13T; S13C; S13E; C17A; C17L; C17V; C17D; C17T; C17I; C17E; C17S; C17G; L21I; L21V; L21A; L21Y; L21F; A56L; 159V; 159A; 159L; M62I; M62V; M62L; L63A; L63F; L63Y; I66L; I66V; I66A; I69V; I69L; I69A; V84I; V84L; V84A; L87F; L87I; L87Y; L87V; L87A; L87W; V91I; V91A;

V91L; V91F; V91Y; V98A; L98F; G114F; G114L; S118A; S118V; S118C; S118L; S118E; L122I; L122V; L122A; L122F; L122Y; L122W; I129V; I129L; I129A; V146I; V146A; I150V; I150A; I150L; I150F; F154L; F154Y; F157V; I157V; I157L; I157A; L160I; L160V; L160A; L160F; L160Y; T115A; T161V; T161I; T161D; T161C; T161E; and T161G. These may be done either individually or in combination, with any combination being possible. However, as outlined herein, preferred embodiments utilize at least five, and preferably more, variable positions in each IbA protein.

Particularly preferred sequences for IbA proteins are selected from the group consisting of: [V841 and L87F (FIG. 4B and FIG. 10B) (SEQ ID NOS:4,18)]; [V84I, V91I, L98F, L122I, and I157L (see FIG. 5B) (SEQ ID NO:5)]; [S13F, I69V, V84I, V91I, L98F, S118A, L122I, V146I, I157L, and T161A (see FIG. 6B) (SEQ ID NO:6)]; [S13Y, I69V, V84I, V91I, L98F, S118V, L122V, V146I, I157L, and T161A (see FIG. 6C) (SEQ ID NO:7)]; [S13F, V84I, V91I, L98F, S118A, L122I, I157L, and T161A (see FIG. 6D) (SEQ ID NO:8)]; [S13F, C17D, I69V, V84I, V91I, L98F, S118A, L122I, VI146I, I157L, and T161A (see FIG. 7B) (SEQ ID NO:9)]; [S13Y, C17D, 169V, V841, V91I, L98F, S118V, L122A, V146I, I157L, and T161A (see FIG. 7C) (SEQ ID NO:10)]; [S13F, C17D, V84I, V91I, L98F, S118A, L122I, I157L, and T161A (see FIG. 70) (SEQ ID NO:11)]; [S13E, C17D, V84I, V91I, S118C, V146I, and T161C (see FIG. 8B) (SEQ ID NO:12)]; [S13A, V84I, V91I, S118C, V146I, I157L, and T161C (see FIG. 8C) (SEQ ID NO:13)]; [S13E, C17D, V84I, V91I, S118C, and T161C (see FIG. 8D)(SEQ ID NO:14)]; [S13E, C17D, 169V, V84I, V91I, S118A, L122I, V146I, I157L, and T161(see FIG. 9B) (SEQ ID NO:15)]; [S13E, C17D, V84I, V91I, S118A, V146I, and 1157L (see FIG. 9C) (SEQ ID NO:16)]; [S13E, C17D, V84I, V91I, S118A, L122I, I157L, and T161A (see FIG. 9D) (SEQ ID NO:17)]; [A56L, L63F, V84I, L87F, V91I, and L122F (see FIG. 11B) (SEQ ID NO:19)]; [S13L, A56L, V84I, V91I, G114F, S118L, L122I, and T161A (see FIG. 12B) (SEQ ID NO:20)]; [S13L, C17A, A56L, V84I, L87F, V91L, G114F, S118L, L122I, and T161E (see FIG. 13B) (SEQ ID NO:21)]; [S13E, A56L, V84I, V91I, G114L, S118E, and T161E (see FIG. 14B) (SEQ ID NO:22)]; [C17T, A56L, V84I, V84I, V91I, S118E, G114L, S118E, and T161E (see FIG. 15B) (SEQ ID NO:23)]; and [C17T, A56L, V84I, V91I, S118E, and T161E (see FIG. 16B) (SEQ ID NO:24)].

Particularly preferred sequences for the A-chain of an IbA protein are selected from the group consisting of: [V84I and L87F (FIG. 4B) (SEQ ID NO:4)]; [V84I, V91I, L98F, L122I, and I157L (see FIG. 5B) (SEQ ID NO:5)]; [S13F, I69V, V84I, V91I, L98F, S118A, L122I, V146I, I157L, and T161A (see FIG. 6B)(SEQ ID NO:6)]; [S13Y, I69V, V84I, V91I, L98F, S118V, L122V, V146I, I157L, and T161A (see FIG. 6C) (SEQ ID NO:7)]; [S13F, V84I, V91I, L98F, S118A, L122I, I157L, and T161A (see FIG. 6D) (SEQ ID NO:8)]; [S13F, C17D, I69V, V84I, V91I, L98F, S118A, L122I, V146I, I157L, and T161A (see FIG. 7B) (SEQ ID NO:9)]; [S13Y, C17D, I69V, V84I, V91I, L98F, S118V, L122V, V146I, I157L, and T161A (see FIG. 7C) (SEQ ID NO:10)]; [S13F, C17D, V84I, V91I, L98F, S118A, L122I, I157L, and T161A (see FIG. 7D) (SEQ ID NO:11)]; [S13E, C17D, V84I, V91I, S118C, V146I, and T161C (see FIG. 8B) (SEQ ID NO:12)]; [S13A, V84I, V91I, S118C, V146I, I157L, and T161C (see FIG. 8C) (SEQ ID NO:13)]; [S13E, C17D, V84I, V91I, S118C, and T161C (see FIG. 8D) (SEQ ID NO:14)]; [S13E, C17D, I69V, V84I, V91I, S118A, L122I, V146I, I157L, and T161A (see FIG. 9B)(SEQ ID NO:15)]; [S13E, C17D, V84I, V91I, S118A, V146I, and I157L (see FIG. 9C) (SEQ ID NO:16)]; and [S13E, C17D, V84I, V9I, S118A, L122I, I157L, and T161A (see FIG. 9D) (SEQ ID NO:17)].

Particularly preferred sequences for the B-chain of an IbA protein are selected from the group consisting of: [V84I and L87F (FIG. 10B) (SEQ ID NO:18)]; [A56L, L63F, V84I, L87F, V91I, and L122F (see FIG. 11B) (SEQ ID NO:19)]; [S13L, A56L, V84I, V91I, G114F, S118L, L122I, and (see FIG. 12B) (SEQ ID NO:20)]; [S13L, C17A, A56L, V84I, L87F, V91L, G114F, S118L, L122I, and T161E (see FIG. 13B) (SEQ ID NO:21)]; [S13E, A56L, V84I, V91I, G114L, S118E, and T161E (see FIG. 14B) (SEQ ID NO:22)]; [C17T, A56L, V84I, V91I, G114L, S118E, and T161E (see FIG 15B) (SEQ ID NO:23)]; and [C17T, A56L, V84I, V91I, S118E, and T161E (see FIG. 16B) (SEQ ID NO:24)].

In a preferred embodiment, the IbA proteins of the invention are human IFN-β conformers. By "conformer" herein is meant a protein that has a protein backbone 3D structure that is virtually the same but has significant differences in the amino acid side chains. That is, the IbA proteins of the invention define a conformer set, wherein all of the proteins of the set share a backbone structure and yet have sequences that differ by at least 3–5%. The three dimensional backbone structure of an IbA protein thus substantially corresponds to the three dimensional backbone structure of human IFN-β. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the human IFN-β structure, with no more than 1.5 Å being preferred, and no more than 1 Å being particularly preferred. In general, these distances may be determined in two ways. In one embodiment, each potential conformer is crystallized and its three dimensional structure determined. Alternatively, as the former is quite tedious, the sequence of each potential conformer is run in the PDA program to determine whether it is a conformer.

IbA proteins may also be identified as being encoded by IbA nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, an IbA nucleic acid encodes an IbA protein. As will be appreciated by those in the art, due to the degeneracy of the genetic code, an extremely large number of nucleic acids may be made, all of which encode the IbA proteins of the present invention. Thus, having identified a particular amino acid sequence, those skilled in the art could make any number of different nucleic acids, by simply modifying the sequence of one or more codons in a way which does not change the amino acid sequence of the IbA.

In one embodiment, the nucleic acid homology is determined through hybridization studies. Thus, for example, nucleic acids which hybridize under high stringency to the nucleic acid sequence shown in FIG. 1 or its complement and encode a IbA protein is considered an IbA gene.

High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The IbA proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid" herein is meant nucleic acid, originally formed in vitro, in general, by the manipulation of nucleic acid by endonucleases, in a form not normally found in nature. Thus an isolated IbA nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an IbA protein from one organism in a different organism or host cell. Alternatively, the protein may be made at a significantly higher concentration than is normally seen, through the use of an inducible promoter or high expression promoter, such that the protein is made at increased concentration levels. Furthermore, all of the IbA proteins outlined herein are in a form not normally found in nature, as they contain amino acid substitutions, insertions and deletions, with substitutions being preferred, as discussed below.

Also included within the definition of IbA proteins of the present invention are amino acid sequence variants of the IbA sequences outlined herein and shown in the Figures. That is, the IbA proteins may contain additional variable positions as compared to human IFN-β. These variants fall into one or more of three classes: substitutional, insertional or deletional variants. These variants ordinarily are prepared by site specific mutagenesis of nucleotdes in the DNA encoding an IbA protein, using cassette or PCR mutagenesis or other techniques well known in the art, to produce DNA encoding the variant, and thereafter expressing the DNA in recombinant cell culture as outlined above. However, variant IbA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the IbA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed IbA variants screened for the optimal combination of desired activity. Techniques for making substitution mutations at predetermined sites in DNA having a known sequence are well known, for example, M13 primer mutagenesis and PCR mutagenesis. Screening of the mutants is done using assays of IbA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the IbA protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original IbA protein, although variants also are selected to modify the characteristics of the IbA proteins as needed. Alternatively, the variant may be designed such that the biological activity of the IbA protein is altered. For example, glycosylation sites may be altered or removed. Similarly, the biological function may be altered; for example, in some instances it may be desirable to have more or less potent IFN-β activity.

The IbA proteins and nucleic acids of the invention can be made in a number of ways. Individual nucleic acids and proteins can be made as known in the art and outlined below. Alternatively, libraries of IbA proteins can be made for testing.

In a preferred embodiment, sets or libraries of IbA proteins are generated from a probability distribution table. As outlined herein, there are a variety of methods of generating a probability distribution table, including using PDA, sequence alignments, forcefield calculations such as SCMF calculations, etc. In addition, the probability distribution can be used to generate information entropy scores for each position, as a measure of the mutational frequency observed in the library.

In this embodiment, the frequency of each amino acid residue at each variable position in the list is identified. Frequencies can be thresholded, wherein any variant frequency lower than a cutoff is set to zero. This cutoff is preferably 1%, 2%, 5%, 10% or 20%, with 10% being particularly preferred. These frequencies are then built into the IbA library. That is, as above, these variable positions are collected and all possible combinations are generated, but the amino acid residues that "fill" the library are utilized on a frequency basis. Thus, in a non-frequency based library, a variable position that has 5 possible residues will have 20% of the proteins comprising that variable position with the first possible residue, 20% with the second, etc. However, in a frequency based library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create libraries as described herein. SCMF can be used in three ways: the frequencies of amino acids and rotamers for each amino acid are listed at each position; the probabilities are determined directly from SCMF (see Delarue et la. Pac. Symp. Biocomput. 109–21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered list of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53–70 (1995); all of which are expressly incorporated by reference. Similar methods include, but are not limited to, OPLS-AA (Jorgensen, et al., J. Am. Chem. Soc. (1996), v 118, pp 11225–11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, et al., Protein Science (1993), v 2, pp1697–1714; Liwo, et al., Protein Science (1993), v 2, pp1715–1731; Liwo, et al., J. Comp. Chem. (1997), v 18, pp849–873; Liwo, et al., J. Comp. Chem. (1997), v 18, pp874–884; Liwo, et al., J. Comp. Chem. (1998), v 19, pp259–276; Forcefield for Protein Structure Prediction (Liwo, et al., Proc. Natl. Acad. Sci. USA (1999), v 96, pp5482–5485); ECEPP/3 (Liwo et al., J Protein Chem 1994 May;13(4):375–80); AMBER 1.1 force field (Weiner, et al., J. Am. Chem. Soc. v106, pp765–784); AMBER 3.0 force field (U.C. Singh et al., Proc. Natl. Acad. Sci. USA. 82:755–759); CHARMM and CHARMM22 (Brooks, et al., J. Comp. Chem. v4, pp 187–217); cvff3.0 (Dauber-Osguthorpe, et al., (1988) Proteins: Structure, Function and Genetics, v4, pp31–47); cff91 (Maple, et al., J. Comp. Chem. v 5, 162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table can be obtained by a combination of sequence alignments and computational approaches. For example, one can add amino acids found in the alignment of homologous sequences to the result of the computation. Preferable one can add the wild type amino acid identity to the probability table if it is not found in the computation.

As will be appreciated, an IbA library created by recombining variable positions and/or residues at the variable position may not be in a rank-ordered list. In some embodiments, the entire list may just be made and tested. Alternatively, in a preferred embodiment, the IbA library is also in the form of a rank ordered list. This may be done for several reasons, including the size of the library is still too big to generate experimentally, or for predictive purposes. This may be done in several ways. In one embodiment, the library is ranked using the scoring functions of PDA to rank the library members. Alternatively, statistical methods could be used. For example, the library may be ranked by frequency score; that is, proteins containing the most of high frequency residues could be ranked higher, etc. This may be done by adding or multiplying the frequency at each variable position to generate a numerical score. Similarly, the library different positions could be weighted and then the proteins scored; for example, those containing certain residues could be arbitrarily ranked.

In a preferred embodiment, the different protein members of the IbA library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 17. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these positions: (number of oligos for constant positions)+M1+M2+M3+ . . . Mn=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters can be carried out by a number of ways, e.g. by using known pattern recognition methods, comparisons of frequencies of occurence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in pattern recognition; New York, Wiley-lnterscience [1 972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++/Abhijit S. Pandya, Robert B. Macy. Boca Raton, Fla.: CRC Press, 1996; Handbook of pattern recognition & computer vision I edited by C. H. Chen, L. F. Pau, P. S. P. Wang. 2nd ed. Singapore; River Edge, N.J.: World Scientific, c1999; Friedman, Introduction to Pattern Recognition: Statistical, Structural, Neural, and Fuzy Logic Approaches; River Edge, N.J.: World Scientific, c1999, Series title: Series in machine perception and artificial intelligence; vol. 32; all of which are expressly incorporated by reference. In addition, programs used to search for consensus motifs can be used as well.

In addition, correlations and shuffling can be fixed or optimized by altering the design of the oligonucleotides; that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotide start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotide of different lengths.

In a preferred embodiment, the IbA library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811, 238; 5,605,793; 5,837,458 and PCT US/19256, all of which are expressly incorporated by reference in their entirety. This set of sequences can also be an artificial set; for example, from a probability table (for example generated using SCMF) or a Monte Carlo set. Similarly, the "family" can be the top 10 and the bottom 10 sequences, the top 100 sequence, etc. This may also be done using error-prone PCR.

Thus, in a preferred embodiment, in silico shuffling is done using the computational methods described herein. That is, starting with either two libraries or two sequences, random recombinations of the sequences can be generated and evaluated.

In a preferred embodiment, error-prone PCR is done to generate the IbA library. See U.S. Pat. Nos. 5,605,793, 5,811,238, and 5,830,721, all of which are hereby incorporated by reference. This can be done on the optimal sequence or on top members of the library, or some other artificial set or family. In this embodiment, the gene for the optimal sequence found in the computational screen of the primary library can be synthesized. Error prone PCR is then performed on the optimal sequence gene in the presence of oligonucleofides that code for the mutations at the variant positions of the library (bias oligonucleotides). The addition of the oligonucleotdes will create a bias favoring the incorporation of the mutations in the library. Alternatively, only oligonucleotdes for certain mutations may be used to bias the library.

In a preferred embodiment, gene shuffling with error prone PCR can be performed on the gene for the optimal sequence, in the presence of bias oligonucleotides, to create a DNA sequence library that reflects the proportion of the mutations found in the IbA library. The choice of the bias oligonucleotides can be done in a variety of ways; they can be chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions can be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild type gene or other gene can be used, as is schematically depicted in FIG. 18. In this embodiment, a starting gene is used; generally, although this is not required, the gene is usually the wild type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits; the first is that this generally requires fewer oligonucleotides and can result in fewer errors. In addition, it has experimental advantages in that if the wild type gene is used, it need not be synthesized.

In addition, there are several other techniques that can be used, as exemplified in the figures, e.g. FIGS. 19–21. In a preferred embodiment, ligation of PCR products is done.

In a preferred embodiment, a variety of additional steps may be done to the IbA library; for example, further computational processing can occur, different IbA libraries can be recombined, or cutoffs from different libraries can be combined. In a preferred embodiment, an IbA library may be computationally remanipulated to form an additional IbA library (sometimes referred to herein as "tertiary libraries"). For example, any of the IbA library sequences may be chosen for a second round of PDA, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the IbA library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library can be generated from combining different IbA libraries. For example, a probability distribution table from a first IbA library can be generated and recombined, either computationally or experimentally, as outlined herein. A PDA IbA library may be combined with a sequence alignment IbA library, and either recombined (again, computationally or experimentally) or just the cutoffs from each joined to make a new tertiary library. The top sequences from several libraries can be recombined. Sequences from the top of a library can be combined with sequences from the bottom of the library to more broadly sample sequence space, or only sequences distant from the top of the library can be combined. IbA libraries that analyzed different parts of a protein can be combined to a tertiary library that treats the combined parts of the protein.

In a preferred embodiment, a tertiary library can be generated using correlations in an IbA library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode an IbA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the IbA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the IbA protein, a replacement of the naturally occurring secretory leader sequence is desired. In this embodiment, an unrelated secretory leader sequence is operably linked to an IbA encoding nucleic acid leading to increased protein secretion. Thus, any secretory leader sequence resulting in enhanced secretion of the IbA protein, when compared to the secretion of IFN-β and its secretory sequence, is desired. Suitable secretory leader sequences that lead to the secretion of a protein are know in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus.

Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, the expression vector comprises the components described above and a gene encoding an IbA protein. In this aspect, only one species of an IbA protein will be expressed in the cell comprising the expression vector. In one aspect of this embodiment, it is desired to express an optimized A-chain of IFN-β and an optimized B-chain of IFN-β within the same cell and thus, two expression vectors, one comprising a gene coding for an optimized A-chain of IFN-β, the other one comprising a gene coding for an optimized B-chain of IFN-β are introduced into the same host cell. This allows formation of a preferred IbA dimer.

In another aspect of this embodiment, an expression vector is constructed that comprises two IbA genes encoding two different IbA proteins. In this embodiment, one IbA gene encodes an optimized A chain of IFN-β and the second gene encodes an optimized B-chain of IFN-β. In one aspect of this embodiment, a polycistronic gene can be constructed as is known in the art for co-expression in a host cell.

As will be appreciated by those in the art, all combinations are possible and accordingly, as used herein, the combination of components, comprised by one or more vectors, which may be retroviral or not, is referred to herein as a "vector composition".

The IbA nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $(Ca_3PO_4)_2$ precipitation, liposome fusion, lipofectin®, electroporation, viral infection, etc. The IbA nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The IbA proteins of the present invention are produced by culturing a host cell transformed with an expression vector containing nucleic acid encoding an IbAA protein, under the appropriate conditions to induce or cause expression of the IbA protein. The conditions appropriate for IbA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, Pichia Pastoris, etc.

In a preferred embodiment, the IbA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogeneous nucleic acid other than the IbA nucleic acid.

In a preferred embodiment, the IbA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the IbA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD)

sequence and includes an initiation codon and a sequence 3-9 nucleotides in length located 3-11 nucleotides upstream of the initiation codon.

The expression vector may also include a signal peptide sequence that provides for secretion of the IbA protein in a bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to an IbA encoding nucleic acid, are preferred.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, IbA proteins are produced in insect cells. Expression vectors for the transformation of insect cells, and in particular, baculovirus-based expression vectors, are well known in the art.

In a preferred embodiment, IbA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the IbA polypeptides of the invention may be further fused to other proteins, if desired, for example to increase expression or stabilize the protein.

In one embodiment, the IbA nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the IbA proteins may be covalently modified. One type of covalent modification includes reacting targeted amino acid residues of an IbA polypeptide with an organic derivatizing agent that is capable of reacting with selected side chains or the N-or C-terminal residues of an IbA polypeptide. Derivatization with bifunctional agents is useful, for instance, for crosslinking an IbA protein to a water-insoluble support matrix or surface for use in the method for purifying anti-IbA antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79–86 (1983)], acetylaffon of the N-terminal amine, and amidation of any C-terminal carboxyl group.

Another type of covalent modification of the IbA polypeptide included within the scope of this invention comprises altering the native glycosylation pattern of the polypeptide. "Altering the native glycosylation pattern" is intended for purposes herein to mean deleting one or more carbohydrate moieties found in native sequence IbA polypeptide, and/or adding one or more glycosylation sites that are not present in the native sequence IbA polypeptide.

Addition of glycosylation sites to IbA polypeptides may be accomplished by altering the amino acid sequence thereof. The alteration may be made, for example, by the addition of, or substitution by, one or more serine or threonine residues to the native sequence IbA polypeptide (for O-linked glycosylation sites). The IbA amino acid sequence may optionally be altered through changes at the DNA level, particularly by mutating the DNA encoding the IbA polypeptide at preselected bases such that codons are generated that will translate into the desired amino acids.

Another means of increasing the number of carbohydrate moieties on the IbA polypeptide is by chemical or enzymatic coupling of glycosides to the polypeptide. Such methods are described in the art, e.g., in WO87/05330 published Sep. 11, 1987, and in Aplin and Wriston, CRC Crit. Rev. Biochem., pp. 259–306 (1981).

Removal of carbohydrate moieties present on the IbA polypeptide may be accomplished chemically or enzymatically or by mutational substitution of codons encoding for amino acid residues that serve as targets for glycosylabon. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Such derivatized moieties may improve the solubility, absorption, permeability across the blood brain barrier, biological half life, and the like. Such moieties or modifications of IbA polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of IbA comprises linking the IbA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

IbA polypeptides of the present invention may also be modified in a way to form chimeric molecules comprising an IbA polypeptide fused to another, heterologous polypeptide or amino acid sequence. In one embodiment, such a chimeric molecule comprises a fusion of an IbA polypeptide with a tag polypeptide which provides an epitope to which an anti-tag antibody can selectively bind. The epitope tag is generally placed at the amino-or carboxyl-terminus of the IbA polypeptide. The presence of such epitope-tagged forms of an IbA polypeptide can be detected using an antibody against the tag polypeptide. Also, provision of the epitope tag enables the IbA polypepbde to be readily purified by affinity purification using an anti-tag antibody or another type of affinity matrix that binds to the epitope tag. In an alternative embodiment, the chimeric molecule may comprise a fusion of an IbA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptdes include the Flag-peptide [Hopp et al., BioTechnology 6:1204–1210 (1988)]; the KT3 epitope peptde [Martin et al., Science 255:192–1944 (1992)]; tubulin epitope peptide [Skinner et al., J. Biol. Chem. 266:15163–15166 (1991)]; and the T7 gene 10 protein peptde tag [Lutz-Freyermuth et al., Proc. Natl. Acad. Sci. U.S.A. 87:6393–6397 (1990)].

In a preferred embodiment, the IbA protein is purified or isolated after expression. IbA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the IbA protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the IbA protein. In some instances no purification will be necessary.

Once made, the IbA proteins and nucleic acids of the invention find use in a number of applications. In a preferred embodiment, the IbA proteins are administered to a patent to treat an IFN-β-associated disorder.

By "IFN-β associated disorder" or "IFN-β responsive disorder" or "condition" herein is meant a disorder that can be ameliorated by the administration of a pharmaceutical composition comprising an IFN-β or IbA protein, including, but not limited to, multiple sclerosis; idiopathic pulmonary fibrosis; inflammatory diseases; viral diseases; infections caused by papilloma viruses, such as genital warts and condylomata of the uterine cervix; infections caused by hepatitis viruses, such as acute/chronic hepatitis B and non-A, non-B hepatitis (hepatitis C); infections caused by herpes viruses, such as herpes genitalis, herpes zoster, herpes keratitis, and herpes simplex; viral encephalitis; cytomegalovirus pneumonia; prophylaxis of rhinovirus; cancer, including several malignant diseases such as osteosarcoma, basal cell carcinoma, cervical dysplasia, glioma, acute myeloid leukemia, multiple myeloma, Hodgkin's disease, melanoma, renal cancer, liver cancer, and breast cancer.

In a preferred embodiment, a therapeutically effective dose of an IbA protein is administered to a patient in need of treatment. By "therapeutically effective dose" herein is meant a dose that produces the effects for which it is administered. The exact dose will depend on the purpose of the treatment, and will be ascertainable by one skilled in the art using known techniques. In a preferred embodiment, dosages of about 5 μg/kg are used, administered either intraveneously or subcutaneously. As is known in the art, adjustments for IbA protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, in the case of multiple sclerosis, successful administration of an IbA protein prior to onset of the disease results in "treatment" of the disease. As another example, successful administration of an IbA protein after clinical manifestation of the disease to combat the symptoms of the disease comprises treatment" of the disease. "Treatment" also encompasses administration of an IbA protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals, in particular humans, already having the disease or disorder, as well as those prone to having the disease or disorder, including those in which the disease or disorder is to be prevented.

In another embodiment, a therapeutically effective dose of an IbA protein, an IbA gene, or an IbA antibody is administered to a patient having a disease involving inappropriate expression of IFN-β. A "disease involving inappropriate expression of a IFN-β" within the scope of the present invention is meant to include diseases or disorders characterized by an overabundance of IFN-β. This overabundance may be due to any cause, including, but not limited to, overexpression at the molecular level, prolonged or accumulated appearance at the site of action, or increased activity of IFN-β relative to normal. Included within this definition are diseases or disorders characterized by a reduction of IFN-β. This reduction may be due to any cause, including, but not limited to, reduced expression at the molecular level, shortened or reduced appearance at the site of action, or decreased activity of IFN-β relative to normal. Such an overabundance or reduction of IFN-β can be measured relative to normal expression, appearance, or activity of IFN-β according to, but not limited to, the assays described and referenced herein.

The administration of the IbA proteins of the present invention, preferably in the form of a sterile aqueous solution, can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, or multiple sclerosis, the IbA A protein may be directly applied as a solution or spray. Depending upon the manner of introduction, the pharmaceutical composition may be formulated in a variety of ways. The concentration of the therapeutically active IbA protein in the formulation may vary from about 0.1 to 100 weight %. In another preferred embodiment, the concentration of the IbA protein is in the range of 0.003 to 1.0 molar, with dosages from 0.03, 0.05, 0.1, 0.2, and 0.3 millimoles per kilogram of body weight being preferred.

The pharmaceutical compositions of the present invention comprise an IbA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In addition, in one embodiment, the IbA proteins of the present invention are formulated using a process for pharmaceutical compositions of recombinant IFN-β as described in U.S. Pat. No. 5,183,746 which, hereby, is expressly incorporated in its entirety.

In a further embodiment, the IbA proteins are added in a micellular formulation; see U.S. Pat. No. 5,833,948, hereby expressly incorporated by reference in its entirety.

Combinations of pharmaceutical compositions may be administered. Moreover, the compositions may be administered in combination with other therapeutics.

In one embodiment provided herein, antibodies, including but not limited to monoclonal and polyclonal antibodies, are raised against IbA proteins using methods known in the art. In a preferred embodiment, these ant-IbA antibodies are used for immunotherapy. Thus, methods of immunotherapy are provided. By "immunotherapy" is meant treatment of an IFN-β related disorders with an antibody raised against an IbA protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an IbA protein antigen to which antibodies are raised. As appreciated by one of ordinary skill in the art, the IbA protein antigen may be provided by injecting an IbA polypeptide against which antibodies are desired to be raised into a recipient, or contacting the recipient with an IbA protein encoding nucleic acid, capable of expressing the IbA protein antigen, under conditions for expression of the IbA protein antigen.

In another preferred embodiment, a therapeutic compound is conjugated to an antibody, preferably an ant-IbA protein antibody. The therapeutic compound may be a cytotoxic agent. In this method, targeting the cytotoxic agent to tumor tissue or cells, results in a reduction in the number of afflicted cells, thereby reducing symptoms associated with cancer, and IbA protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, IbA proteins are administered as therapeutic agents, and can be formulated as outlined above. Similarly, IbA genes (including both the full-length sequence, partial sequences, or regulatory sequences of the IbA coding regions) can be administered in gene therapy applications, as is known in the art. These IbA genes can include antisense applications, either as gene therapy (i.e. for incorporation into the genome) or as antisense compositions, as will be appreciated by those in the art.

In a preferred embodiment, the nucleic acid encoding the IbA proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short anbsense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143–4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. U.S.A. 87:3410–3414 (1990). For review of gene marking and gene therapy protocols see Anderson et al., Science 256:808–813 (1992).

In a preferred embodiment, IbA genes are administered as DNA vaccines, either single genes or combinations of IbA genes. Naked DNA vaccines are generally known in the art. Brower, Nature Biotechnology, 16:1304–1305 (1998). Methods for the use of genes as DNA vaccines are well known to one of ordinary skill in the art, and include placing an IbA gene or portion of an IbA gene under the control of a promoter for expression in a patent in need of treatment. The IbA gene used for DNA vaccines can encode full-length IbA proteins, but more preferably encodes portions of the IbA proteins including peptides derived from the IbA protein. In a preferred embodiment a patient is immunized with a DNA vaccine comprising a plurality of nucleotide sequences derived from an IbA gene. Similarly, it is possible to immunize a patient with a plurality of IbA genes or portions thereof as defined herein. Without being bound by theory, expression of the polypeptide encoded by the DNA vaccine, cytotoxic T-cells, helper T-cells and antibodies are induced which recognize and destroy or eliminate cells expressing IFN-β proteins.

In a preferred embodiment, the DNA vaccines include a gene encoding an adjuvant molecule with the DNA vaccine. Such adjuvant molecules include cytokines that increase the immunogenic response to the IbA polypeptide encoded by the DNA vaccine. Additional or alternative adjuvants are known to those of ordinary skill in the art and find use in the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLE 1

DESIGN AND CHARACTERIZATION OF NOVEL IbA PROTEINS BY PDA

Summary: Sequences for novel interferon-beta activity proteins (IbA proteins) were designed by simultaneously optimizing residues in the buried core of the protein using Protein Design Automation (PDA) as described in WO98/47089, U.S. Ser. Nos. 09/058,459, 09/127,926, 60/104,612, 60/158,700, 09/419,351, 60/181,630, 60/186,904, and U.S patent application, entitled *Protein Design Automation For Protein Libraries* (Filed: Apr. 14, 2000; Inventor: Bassil Dahiyat), all of which are expressly incorporated by reference in their entirety. Several core designs were completed, with 20–61 residues considered corresponding to $20^{20}$–$20^{61}$ sequence possibilities. Residues unexposed to solvent were designed in order to minimize changes to the molecular surface and to limit the potential for antigenicity of designed novel protein analogues.

Calculations required from 12–19 hours on 16 Silicon Graphics R10000 CPU's. The global optimum sequence from each design was selected for characterization. From 2–11 residues were changed from human IFN-β in the designed proteins, out of 166 residues total.

COMPUTATIONAL PROTOCOLS

Template Structure Preparation:

For this study the crystal structure of human IFN-β as deposited in the PDB data bank was used [PDB record 1AU1; Karpusasetal. Proc. Natl. Acad. Sci. U.S.A. 94(22):11813–8 (1997)]. Karpasus et al. expressed human IFN-β in CHO cells (glycosylated form) and solved the structure by x-ray crystallography to a resolution of 2.2 Ångstrom. The structure of IFN-β is dimeric containing a zinc ion at the interface and both IFN-β monomers (A-chain and B-chain) are glycosylated at asparagine 80. Although both monomers contained 166 amino acid residues, the coordinates for residues 28 to 30 in the B-monomer were not given in the PDB file 1AU1. PDA calculations were performed for the A-chain and B-chain separately. The zinc ion, all water molecules and the carbohydrate moiety as well as all hydrogen atoms that are present in the PDB file 1AU1 were removed from the structure prior to the PDA calculation.

Design Strategies:

Core residues were selected for design since optimization of these positions can improve stability, although stabilization has been obtained from modifications at other sites as well. Core designs also minimize changes to the molecular surface and thus limit the designed protein's potential for antigenicity. PDA calculations were run on 3 core sequences (see FIG. 3) and in a total of 15 core designs (IFN-β A-chain: Core 1, Core 2, Core 2a, Core 3, Core 4, Core 5, and Core 6; IFN-β B-chain: Core 1, Core 2, Core 2a, Core 3, Core 4, Core 5, Core 6 and Core 7; see below).

PDA Calculations

All PDA calculations were performed with salvation model 2. Solvation model 2 is the solvation model described by Street and Mayo [Fold. Design 3:253–258 (1998)]. If possible, Dead End Elimination (DEE) was run to completion to find the PDA ground state. This was done for the PDA calculations for the A-chain and B-chain of Core 1, Core 2 and Core 2a, as defined below. For the calculation of Core 3, Core 4, Core 5, Core 6 and Core 7, DEE was aborted after the rotamer sequence space was reduced to less than $10^{25}$ sequences. The DEE calculation was for all the given Core calculation followed by Monte Carlo (MC) minimization and a list of the 1000 lowest energy sequences was generated.

A similar procedure was used for the B-chain, where in a first step the side chain of Lys 33 was minimized for 50 steps followed by an additional 50 steps of minimization of the complete B-chain structure. As the coordinates of residues 28 to 30 are missing in the B-chain, the N-terminus of Cys 31 and the C-terminus of Arg 27 were saturated with a hydrogen atom and the NH₂-group in Cys 31 and the COOH group in Arg 27 were kept fixed during minimization to prevent them from moving too far away from their initial positions.

Before the PDA calculations were started an initial preparation of the structure was performed. For the A-chain, the side chains of Phe 50, Glu 61, Lys 115, Met 117 were minimized with Biograf for 50 steps using conjugate gradient procedure without a Coulomb potential. this is followed by an additional 50 steps of conjugate gradient minimization without a Coulomb potential for the complete structure of the A-chain using Biograf. This minimization procedure was chosen to remove initial bad contacts in the structure.

The PDA calculations for all the designs were run using the a2hl p0 rotamer library. This library is based on the backbone-dependent rotamer library of Dunbrack and Karplus (Dunbrack and Karplus, J. Mol. Biol. 230(2):543–74 (1993); hereby expressly incorporated by reference) but includes more rotamers for the aromatic and hydrophobic amino acids; $X_1$ and X2 angle values of rotamers for all the aromatic amino acids and $X_1$ angle values for all the other hydrophobic amino acids were expanded ±1 standard deviation about the mean value reported in the Dunbrack and Karplus library. Typical PDA parameters were used: the van der Waals scale factor was set to 0.9, the H-bond potential well-depth was set to 8.0 kcal/mol, the solvation potential was calculated using type 2 solvation with a nonpolar burial energy of 0.048 kcal/mol and a nonpolar exposure multiplication factor of 1.6, and the secondary structure scale factor was set to 0.0 (secondary structure propensities were not considered). Calculations required from 12–24 hours on 16 Silicon Graphics R10000 CPU's.

Monte Carlo Analysis

Monte Carlo analysis of the sequences produced by PDA shows the ground state (optimal) amino acid and amino acids allowed for each variable position and their frequencies of occurrence (see FIGS. 4 through 29).

EXAMPLE 2

PDA Calculations for the A-chain of IFN-β

Different PDA calculations were performed for the core region of the A-chain of IFN-β. In these calculations the number of positions included in the PDA design were varied and the effect of different PDA parameters on the resulting protein sequences, especially the ground state sequence (SEQ ID NO:4), was analyzed.

A-chain Core 1 Design

By visual inspection, the following residues were identified as belonging to the core of the protein: Leu 6, Gln 10, Asn 14, Cys 17, Leu 21, Ala 55, Ala 56, Thr 58, Ile 59, Met 62, Leu 63, Ile 66, Ile 69, Phe 70, Val 84, Leu 87, Val 91, Gln 94, Leu 98, Ser 118, Leu 122, Tyr 125, Tyr 126, Ile 129, Leu 133, Ala 142, Trp 143, Val 146, Ile 150, Asn 153, Phe 154, Ile 157, and Leu 160. In the first calculation, Cys 17 was not included. Also excluded from the PDA design were Phe 70, Trp 143, and Phe 154, as they are known to be important in the stabilization of the core region, and Gln 10, Thr 58, Gln 94, Ser 118 were excluded as they form side chain H-bonds. Furthermore, residues Tyr 125, Tyr 126 and Asn 153 were not considered as these amino acids are highly conserved in IFN-ps from different organisms as well as Ala 142 as its mutation to Thr is known to lead to loss of function.

Thus, the following positions were included in the PDA design (see also FIG. 3):

```
 6   21  55  56  59  62  63  66  69  84  87  91
Leu Leu Ala Ala Ile Met Leu Ile Ile Val Leu Val 98 122 129 133 146 150 157 160
Leu Leu Ile Leu Val Ile Ile Leu
```

Met 62 was allowed to change to any PHOBIC amino acid (Ala, Val, Leu, Ile, Phe, Tyr, Trp, Met) and the other residues were allowed to change to Ala, Val, Leu, Ile, Phe, Tyr, Trp and the PDA core solvation potential was used including surface area calculation.

The PDA calculation resulted in the following ground state sequence (SEQ ID NO:4):

```
 6   21  55  56  59  62  63  66  69  84  87  91
Leu Leu Ala Ala Ile Met Leu Ile Ile Ile Phe Val 98 122 129 133 146 150 157 160
Leu Leu Ile Leu Val Ile Ile Leu
```

This sequence shows two mutations from the wild type IFN-β sequence, V84I and L87F (see FIG. 4B) (SEQ ID NO:4).

Using Monte Carlo technique a list of low energy sequences was generated. The analysis of the lowest 1000 protein sequences generated by Monte Carlo leads to the mutation pattern shown in FIG. 4A. Thus, any protein sequence showing mutations at the positions according to FIG. 4A will potentially generate a more stable and active IbA. In particular those protein sequences found among the list of the lowest 101 MC generated sequences (data not shown) have a high potential to result in a more stable and active IbA. A preferred IbA sequence is shown in FIG. 4B (SEQ ID NO:4).

A-chain Core 2 Design

To allow more flexibility, all residues that have heavy side chain atoms within a distance of 4 Angstrom of any heavy side chain atom of the amino acids used in the Core 1 calculation were added to the PDA calculation. Thus, Met 1, Gln 10, Asn 14, Cys 17, Phe 38, Phe 50, Thr 58, Glu 61, Phe 70, Glu 81, Gln 94, Ile 95, Leu 102, Lys 115, Tyr 125, Tyr 126, Leu 130, Tyr 138, Thr 144, Arg 147, Leu 151, Asn 153, Phe 154, Arg 159, Thr 161, Tyr 163, and Leu 164 were treated as wild type, such that the conformation of the amino acid side chain could change but not the identity Gln 10, Asn 14, Cys 17, Phe 38, Phe 50, Thr 58, Phe 70, Gln 94, Tyr 125, Tyr 126, Thr 144, Asn 153, Phe 154, Thr 161, and Leu 164 were treated with the PDA core potential for surface area calculation. Ile 95, Leu 102, Arg 147, Leu 151, and Tyr 163 were treated with the PDA boundary potential for surface area calculation. Met 1, Glu 61, Glu 81, Lys 115, Leu 130, Tyr 138, and Arg 159 were treated with the PDA surface potential, but no surface area was calculated.

Thus, the following positions were included in the PDA design (see also FIG. 3):

```
 1   6   10  14  17  21  38  50  55  56  58  59
Met Leu Gln Asn Cys Leu Phe Phe Ala Ala Thr Ile 61  62   63  66  69  70  81  84 87   91  94  95
Glu Met Leu Ile Ile Phe Glu Val Leu Val Gln Ile
```

-continued

```
 98 102 115 122 125 126 129 130 133 138 144 146
Leu Leu Lys Leu Tyr Tyr Ile Leu Leu Tyr Thr Val 147 150 151 153 154 157 159 160 161 163 164
Arg Ile Leu Asn Phe Ile Arg Leu Thr Tyr Leu
```

The PDA calculation resulted in the following ground state sequence (SEQ ID NO:5):

```
  1   6  10  14  17  21  38  50  55  56  58  59
Met Leu Gln Asn Cys Leu Phe Phe Ala Ala Thr Ile 61  62  63  66  69  70  81  84  87  91  94  95
Glu Met Leu Ile Ile Phe Glu Ile Leu Ile Gln Ile 98 102 115 122 125 126 129 130 133 138 144 146
Phe Leu Lys Ile Tyr Tyr Ile Leu Leu Tyr Thr Val 147 150 151 153 154 157 159 160 161 163 164
Arg Ile Leu Asn Phe Leu Arg Leu Thr Tyr Leu
```

This sequence shows five mutations from the wild type sequence, V84I, V91I, L98F, L122I, and I157L (see FIG. 5B) (SEQ ID NO:5).

Using Monte Carlo technique a list of low energy sequences was generated. The analysis of the lowest 1000 protein sequences generated by Monte Carlo leads to the mutation pattern shown in FIG. 5A. Thus, any protein sequence showing mutations at the positions according to FIG. 5A will potentially generate a more stable and active IbA. In particular those protein sequences found among the list of the lowest 101 MC generated sequences (data not shown) have a high potential to result in a more stable and active IbA. A preferred IbA sequence is shown in FIG. 5B (SEQ ID NO:5).

A-chain Core 2a Design

A calculation similar to Core 2 was performed but now all wild type residues were treated with the PDA core potential including the surface area calculation. This calculation yields the same ground state sequence (SEQ ID NO:5) as resulted from Core 2.

```
  1   6  10  14  17  21  38  50  55  56  58  59
Met Leu Gln Asn Cys Leu Phe Phe Ala Ala Thr Ile 61  62  63  66  69  70  81  84  87  91  94  95
Glu Met Leu Ile Ile Phe Glu Ile Leu Ile Gln Ile 98 102 115 122 125 126 129 130 133 138 144 146
Phe Leu Lys Ile Tyr Tyr Ile Leu Leu Tyr Thr Val 147 150 151 153 154 157 159 160 161 163 164
Arg Ile Leu Asn Phe Leu Arg Leu Thr Tyr Leu
```

A-chain Core 3 Design

A slightly larger core region than that used in core 2 was defined. The residues Ser 13, Cys 17, Gly 114, Ser 118, Ala 142, Trp 143, Phe 154, and Thr 161 were added to the PDA design used in core 2a and allowed to change their identity. Ser 13, Ala 142, Trp 143, Phe 154 and Thr 161 could change to any PHOBIC residues except methionine; Cys 17 to any PHOBIC residue plus cysteine, but not to methionine; Gly 114 could become any PHOBIC residue plus glycine, but not methionine; Ser 118 could become any PHOBIC residue plus serine, but no methionine. All these eight were treated with the PDA core potential for surface area calculation. In addition, the following residues were added and treated as wild type using the PDA core potential for surface area calculation: Gln 18, Gln 72, Ser 74, Ser 76, Thr 77, Asn 90, Tyr 132, Lys 136, and Ser 139.

Thus, the following positions were included in the PDA design (see also FIG. 3):

```
  1   6  10  13  14  17  18  21  38  50  55  56
Met Leu Gln Ser Asn Cys Gln Leu Phe Phe Ala Ala 58  59  61  62  63  66  69  70  72  74  76  77
Thr Ile Glu Met Leu Ile Ile Phe Gln Ser Ser Thr 81  84  87  90  91  94  95  98 102 114 115 118
Glu Val Leu Asn Val Gln Ile Leu Leu Gly Lys Ser 122 125 126 129 130 132 133 136 138 139 142 143
Leu Tyr Tyr Ile Leu Tyr Leu Lys Tyr Ser Ala Trp 144 146 147 150 151 153 154 157 159 160 161 163
Thr Val Arg Ile Leu Asn Phe Ile Arg Leu Thr Tyr

164
Leu
```

The PDA calculation resulted in the following ground state sequence (SEQ ID NO:6):

```
  1   6  10  13  14  17  18  21  38  50  55  56
Met Leu Gln Phe Asn Cys Gln Leu Phe Phe Ala Ala 58  59  61  62  63  66  69  70  72  74  76  77
Thr Ile Glu Met Leu Ile Val Phe Gln Ser Ser Thr 81  84  87  90  91  94  95  98 102 114 115 118
Glu Ile Leu Asn Ile Gln Ile Phe Leu Gly Lys Ala 122 125 126 129 130 132 133 136 138 139 142 143
Ile Tyr Tyr Ile Leu Tyr Leu Lys Tyr Ser Ala Trp 144 146 147 150 151 153 154 157 159 160 161 163
Thr Ile Arg Ile Leu Asn Phe Leu Arg Leu Ala Tyr

164
Leu
```

This sequence shows 10 mutations from the wild type sequence, S13F, I69V, V84I, V91I, L98F, S118A, L122I, V146I, I157L, and T161A (see FIG. 6B) (SEQ ID NO:6).

Using Monte Carlo technique a list of low energy sequences was generated. The analysis of the lowest 1000 protein sequences generated by Monte Carlo leads to the mutation pattern shown in FIG. 6A. Thus, any protein sequence showing mutations at the positions according to FIG. 6A will potentially generate a more stable and active IbA. In particular those protein sequences found among the list of the lowest 101 MC generated sequences (data not shown) have a high potential to result in a more stable and active IbA. Preferred IbA sequences are shown in FIGS. 6B, 6C, and 6D (SEQ ID NOS: 6–8).

A-chain Core 4 Design

The newly added residues Ser 13, Cys 17, Ser 118, and Thr 161 were now allowed to change to any of the following amino acids: Ala, Val, Leu, Ile, Phe, Tyr, Trp, Asp, Asn, Glu, Gln, Lys, Ser, Thr, His, and Arg, but they were still treated with the PDA core potential for surface area calculation. Otherwise this calculation is identical to Core 3.

The PDA calculation resulted in the following ground state sequence (SEQ ID NO:9):

```
  1   6  10  13  14  17  18  21  38  50  55  56
Met Leu Gln Phe Asn Asp Gln Leu Phe Phe Ala Ala 58  59  61  62  63  66  69  70  72  74  76  77
Thr Ile Glu Met Leu Ile Val Phe Gln Ser Ser Thr 81  84  87  90  91  94  95  98 102 114 115 118
Glu Ile Leu Asn Ile Gln Ile Phe Leu Gly Lys Ala 122 125 126 129 130 132 133 136 138 139 142 143
Ile Tyr Tyr Ile Leu Tyr Leu Lys Tyr Ser Ala Trp 144 146 147 150 151 153 154 157 159 160 161 163
Thr Ile Arg Ile Leu Asn Phe Leu Arg Leu Ala Tyr

164
Leu
```

This sequence shows 11 mutations from the wild type sequence, S13F, C17D, I69V, V84I, V91I, L98F, S118A, L122I, V146I, I157L, and T161A (see FIG. 7B) (SEQ ID NO:9).

Using Monte Carlo technique a list of low energy sequences was generated. The analysis of the lowest 1000 protein sequences generated by Monte Carlo leads to the mutation pattern shown in FIG. 7A. Thus, any protein sequence showing mutations at the positions according to FIG. 7A will potentially generate a more stable and active IbA. In particular those protein sequences found among the list of the lowest 101 MC generated sequences (data not shown) have a high potential to result in a more stable and active IbA. Preferred IbA sequences are shown in FIGS. 7B, 7C, and 7D (SEQ ID NOS:9–11).

A-chain Core 5 Design

A slightly different change in the identities of the amino acids than in Core4 calculation was now allowed. Leu 6, Leu 21, Ala 55, Ala 56, Ile 59, Leu 63, Ile 66, Ile 69, Val 84, Val 91, Leu 122, Ile 129, Leu 133, Ala 142, Trp 143, Val 146, Ile 150, Phe 154, Ile 157, and Leu 160 could change to any PHOBIC residue except methionine. Met 62 was allowed to change to any PHOBIC amino acid residue; Leu 87, Leu98, and Gly 114 were allowed to change to Ala, Val, Leu, Ile, Gly; and Ser 13, Cys 17, Ser 118, and Thr 161 could change to Ala, Gly, Ser, Thr, Glu, Asp, Gln, Asn, or Cys. All the other residues were treated as wild type as was done in the Core 4 calculation.

The PDA calculation resulted in the following ground state sequence (SEQ ID NO:12):

```
  1   6  10  13  14  17  18  21  38  50  55  56
Met Leu Gln Glu Asn Asp Gln Leu Phe Phe Ala Ala 58  59  61  62  63  66  69  70  72  74  76  77
Thr Ile Glu Met Leu Ile Ile Phe Gln Ser Ser Thr 81  84  87  90  91  94  95  98 102 114 115 118
Glu Ile Leu Asn Ile Gln Ile Leu Leu Gly Lys Ser 122 125 126 129 130 132 133 136 138 139 142 143
Leu Tyr Tyr Ile Leu Tyr Leu Lys Tyr Ser Ala Trp 144 146 147 150 151 153 154 157 159 160 161 163
Thr Ile Arg Ile Leu Asn Phe Ile Arg Leu Cys Tyr

164
Leu
```

This sequence shows 7 mutations from the wild type sequence, S13E, C17D, V84I, V91I, S118C, V146I, and T161C (see FIG. 8B) (SEQ ID NO:12).

Using Monte Carlo technique a list of low energy sequences was generated. The analysis of the lowest 1000 protein sequences generated by Monte Carlo leads to the mutation pattern shown in FIG. 8A. Thus, any protein sequence showing mutations at the positions according to FIG. 8A will potentially generate a more stable and active IbA. In particular those protein sequences found among the list of the lowest 101 MC generated sequences (data not shown) have a high potential to result in a more stable and active IbA. Preferred IbA sequences are shown in FIGS. 8B, 8C, and 8D (SEQ ID NOS:12–14). A DNA library can be generated to mirror the probability table of FIG. 8A that comprises at least one sequence that is more stable and/or active than wild type IFN-β.

A-chain Core 6 Design

A similar calculation to Core 5 was performed where now at positions 13, 17, 113, and 117 no cysteine was allowed to occur.

The PDA calculation resulted in the following ground state sequence (SEQ ID NO:15):

```
  1   6  10  13  14  17  18  21  38  50  55  56
Met Leu Gln Glu Asn Asp Gln Leu Phe Phe Ala Ala 58  59  61  62  63  66  69  70  72  74  76  77
Thr Ile Glu Met Leu Ile Val Phe Gln Ser Ser Thr 81  84  87  90  91  94  95  98 102 114 115 118
Glu Ile Leu Asn Ile Gln Ile Leu Leu Gly Lys Asn 122 125 126 129 130 132 133 136 138 139 142 143
Ile Tyr Tyr Ile Leu Tyr Leu Lys Tyr Ser Ala Trp 144 146 147 150 151 153 154 157 159 160 161 163
Thr Ile Arg Ile Leu Asn Phe Leu Arg Leu Ala Tyr

164
Leu
```

This sequence shows 10 mutations from the wild type sequence, S13E, C17D, I69V, V84I, V91I, S118A, L122I, V146I, I157L, and T161A (see FIG. 9B) (SEQ ID NO:15).

Using Monte Carlo technique a list of low energy sequences was generated. The analysis of the lowest 1000 protein sequences generated by Monte Carlo leads to the mutation pattern shown in FIG. 9A. Thus, any protein sequence showing mutations at the positions according to FIG. 9A will potentially generate a more stable and active IbA. In particular those protein sequences found among the list of the lowest 101 MC generated sequences (data not shown) have a high potential to result in a more stable and active IbA. Preferred IbA sequences are shown in FIGS. 9B, 9C, and 9D (SEQ ID NOS:15–17). A DNA library can be generated to mirror the probability table of FIG. 9A that comprises at least one sequence that is more stable and/or active than wild type IFN-β.

EXAMPLE 3

PDA Calculations for the B-chain of IFN-β

For the B-chain, PDA calculations similar to those of the A-chain were performed.

B-chain Core 1 Design

The same positions as for the A-chain Core 1 calculation were used in the PDA design for the B-chain: Leu 6, Leu 21, Ala 55, Ala 56, Ile 59, Met 62, Leu 63, Ile 66, Ile 69, Val 84, Leu 98, Leu 122, Ile 129, Leu 133, Val 146, Ile 150, Ile 157, and Leu 160.

The PDA calculation resulted in the following ground state sequence (SEQ ID NO:18):

```
 6  21  55  56  59  62  63  66  69  84  87  91
Leu Leu Ala Ala Ile Met Leu Ile Ile Ile Phe Val 98 122 129 133 146 150 157 160
Leu Leu Ile Leu Val Ile Ile Leu
```

This sequence shows two mutations from the wild type IFN-β sequence, V84I and L87F, and is identical with the ground state sequence generated for the A-chain (see FIG. 10B) (SEQ ID NO:18).

Using Monte Carlo technique a list of low energy sequences was generated. The analysis of the lowest 1000 protein sequences generated by Monte Carlo leads to the mutation pattern shown in FIG. 10A. Thus, any protein sequence showing mutations at the positions according to FIG. 10A will potentially generate a more stable and active IbA. In particular those protein sequences found among the list of the lowest 101 MC generated sequences (data not shown) have a high potential to result in a more stable and active IbA. A preferred IbA sequence is shown in FIG. 10B (SEQ ID NO:18). A DNA library can be generated to mirror the probability table of FIG. 10A that comprises at least one sequence that is more stable and/or active than wild type IFN-β.

B-chain Core 2 Design

A calculation similar to that for the A-chain Core 2 design was performed for the B-chain.

The PDA calculation resulted in the following ground state sequence (SEQ ID NO:19):

| | | | | | | | | | | | |
|---|---|---|---|---|---|---|---|---|---|---|---|
| 1 | 6 | 10 | 14 | 17 | 21 | 38 | 50 | 55 | 56 | 58 | 59 |
| Met | Leu | Gln | Asn | Cys | Leu | Phe | Phe | Ala | Leu | Thr | Ile |
| 61 | 62 | 63 | 66 | 69 | 70 | 81 | 84 | 87 | 91 | 94 | 95 |
| Glu | Met | Phe | Ile | Ile | Phe | Glu | Ile | Phe | Ile | Gln | Ile |
| 98 | 102 | 115 | 122 | 125 | 126 | 129 | 130 | 133 | 138 | 144 | 146 |
| Leu | Leu | Lys | Phe | Tyr | Tyr | Ile | Leu | Leu | Tyr | Thr | Val |
| 147 | 150 | 151 | 153 | 154 | 157 | 159 | 160 | 161 | 163 | 164 | |
| Arg | Ile | Leu | Asn | Phe | Ile | Arg | Leu | Thr | Tyr | Leu | |

This sequence shows six mutations from the wild type sequence, A56L, L63F, V84I, L87F, V91I, and L122F (see FIG. 11B) (SEQ ID NO:19).

Using Monte Carlo technique a list of low energy sequences was generated. The analysis of the lowest 1000 protein sequences generated by Monte Carlo leads to the mutation pattern shown in FIG. 11A. Thus, any protein sequence showing mutations at the positions according to FIG. 11A will potentially generate a more stable and active IbA. In particular those protein sequences found among the list of the lowest 101 MC generated sequences (data not shown) have a high potential to result in a more stable and active IbA. A preferred IbA sequence is shown in FIG. 11B (SEQ ID NO:19). A DNA library can be generated to mirror the probability table of FIG. 11A that comprises at least one sequence that is more stable and/or active than wild type IFN-β.

B-chain Core 2a Design

A calculation similar to that for the A-chain Core 2a design was performed for the B-chain. This calculation yields the same ground state sequence (SEQ ID NO:i9) as resulted from Core 2.

| | | | | | | | | | | | |
|---|---|---|---|---|---|---|---|---|---|---|---|
| 1 | 6 | 10 | 14 | 17 | 21 | 38 | 50 | 55 | 56 | 58 | 59 |
| Met | Leu | Gln | Asn | Cys | Leu | Phe | Phe | Ala | Ala | Thr | Ile |
| 61 | 62 | 63 | 66 | 69 | 70 | 81 | 84 | 87 | 91 | 94 | 95 |
| Glu | Met | Leu | Ile | Ile | Phe | Glu | Ile | Phe | Ile | Gln | Ile |
| 98 | 102 | 115 | 122 | 125 | 126 | 129 | 130 | 133 | 138 | 144 | 146 |
| Leu | Leu | Lys | Phe | Tyr | Tyr | Ile | Leu | Leu | Tyr | Thr | Val |
| 147 | 150 | 151 | 153 | 154 | 157 | 159 | 160 | 161 | 163 | 164 | |
| Arg | Ile | Leu | Asn | Phe | Ile | Arg | Leu | Thr | Tyr | Leu | |

This sequence shows six mutations from the wild type sequence, A56L, L63F, V84I, L87F, V91I, and L122F.

B-chain Core 3 Design

A calculation similar to that for the A-chain Core 3 was performed for the B-chain, but instead of residue Gln 18, Phe15 was included in the wild type PDA residue list.

The PDA calculation resulted in the following ground state sequence (SEQ ID NO:20):

| | | | | | | | | | | | |
|---|---|---|---|---|---|---|---|---|---|---|---|
| 1 | 6 | 10 | 13 | 14 | 15 | 17 | 21 | 38 | 50 | 55 | 56 |
| Met | Leu | Gln | Leu | Asn | Phe | Cys | Leu | Phe | Phe | Ala | Leu |
| 58 | 59 | 61 | 62 | 63 | 66 | 69 | 70 | 72 | 74 | 76 | 77 |
| Thr | Ile | Glu | Met | Leu | Ile | Ile | Phe | Gln | Ser | Ser | Thr |
| 81 | 84 | 87 | 90 | 91 | 94 | 95 | 98 | 102 | 114 | 115 | 118 |
| Glu | Ile | Leu | Asn | Ile | Gln | Ile | Leu | Leu | Phe | Lys | Leu |
| 122 | 125 | 126 | 129 | 130 | 132 | 133 | 136 | 138 | 139 | 142 | 143 |
| Ile | Tyr | Tyr | Ile | Leu | Tyr | Leu | Lys | Tyr | Ser | Ala | Trp |
| 144 | 146 | 147 | 150 | 151 | 153 | 154 | 157 | 159 | 160 | 161 | 163 |
| Thr | Val | Arg | Ile | Leu | Asn | Phe | Ile | Arg | Leu | Ala | Tyr |
| 164 | | | | | | | | | | | |
| Leu | | | | | | | | | | | |

This sequence shows 8 mutations from the wild type sequence, S13L, A56L, V84I, V91I, G114F, S118L, L122I, and T161A (see FIG. 12B) (SEQ ID NO:20).

Using Monte Carlo technique a list of low energy sequences was generated. The analysis of the lowest 1000 protein sequences generated by Monte Carlo leads to the mutation pattern shown in FIG. 12A. Thus, any protein sequence showing mutations at the positions according to FIG. 12A will potentially generate a more stable and active IbA. In particular those protein sequences found among the list of the lowest 101 MC generated sequences (data not shown) have a high potential to result in a more stable and active IbA. A preferred IbA sequence is shown in FIG. 12B (SEQ ID NO:20). A DNA library can be generated to mirror the probability table of FIG. 12A that comprises at least one sequence that is more stable and/or active than wild type IFN-β.

B-chain Core 4 Design

A calculation similar to that for the A-chain Core 4 design was performed for the B-chain, but instead of residue Gln 18, Phe 15 was included in the wild type PDA residue list.

The PDA calculation resulted in the following ground state sequence (SEQ ID NO:21):

```
  1   6  10  13  14  15  17  21  38  50  55  56
Met Leu Gln Leu Asn Phe Ala Leu Phe Phe Ala Leu 58  59  61  62  63  66  69  70  72  74  76  77
Thr Ile Glu Met Leu Ile Ile Phe Gln Ser Ser Thr 81  84  87  90  91  94  95  98 102 114 115 118
Glu Ile Phe Asn Leu Gln Ile Leu Leu Phe Lys Leu 122 125 126 129 130 132 133 136 138 139 142 143
Ile Tyr Tyr Ile Leu Tyr Leu Lys Tyr Ser Ala Trp 144 146 147 150 151 153 154 157 159 160 161 163
Thr Val Arg Ile Leu Asn Phe Ile Arg Leu Glu Tyr

164
Leu
```

This sequence shows 10 mutations from the wild type sequence, S13L, C17A, A56L, V84I, L87F, V91L, G114F, S118L, L122I, and T161E (see FIG. 13B) (SEQ ID NO:21).

Using Monte Carlo technique a list of low energy sequences was generated. The analysis of the lowest 1000 protein sequences generated by Monte Carlo leads to the mutation pattern shown in FIG. 13A. Thus, any protein sequence showing mutations at the positions according to FIG. 13A will potentially generate a more stable and active IbA. In particular those protein sequences found among the list of the lowest 101 MC generated sequences (data not shown) have a high potential to result in a more stable and active IbA. A preferred IbA sequence is shown in FIG. 13B (SEQ ID NO:21). A DNA library can be generated to mirror the probability table of FIG. 13A that comprises at least one sequence that is more stable and/or active than wild type IFN-β.

B-chain Core 5 Design

A calculation similar to that for the A-chain Core 5 design was performed for the B-chain. Now, Gln 18 was included in the wild type PDA residue list, exactly as was done in the Core 5 calculation for the A-chain.

The PDA calculation resulted in the following ground state sequence (SEQ ID NO:22):

```
  1   6  10  13  14  17  18  21  38  50  55  56
Met Leu Gln Glu Asn Cys Gln Leu Phe Phe Ala Leu 58  59  61  62  63  66  69  70  72  74  76  77
Thr Ile Glu Met Leu Ile Ile Phe Gln Ser Ser Thr 81  84  87  90  91  94  95  98 102 114 115 118
Glu Ile Leu Asn Ile Gln Ile Leu Leu Leu Lys Glu 122 125 126 129 130 132 133 136 138 139 142 143
Leu Tyr Tyr Ile Leu Tyr Leu Lys Tyr Ser Ala Trp 144 146 147 150 151 153 154 157 159 160 161 163
Thr Val Arg Ile Leu Asn Phe Ile Arg Leu Glu Tyr

164
Leu
```

This sequence shows 7 mutations from the wild type sequence, S13E, A56L, V84I, V91I, G114L, S118E, and T161E (see FIG. 14B) (SEQ ID NO:22).

Using Monte Carlo technique a list of low energy sequences was generated. The analysis of the lowest 1000 protein sequences generated by Monte Carlo leads to the mutation pattern shown in FIG. 14A. Thus, any protein sequence showing mutations at the positions according to FIG. 14A will potentially generate a more stable and active IbA. In particular those protein sequences found among the list of the lowest 101 MC generated sequences (data not shown) have a high potential to result in a more stable and active IbA. A preferred IbA sequence is shown in FIG. 14B (SEQ ID NO:22). A DNA library can be generated to mirror the probability table of FIG. 14A that comprises at least one sequence that is more stable and/or active than wild type IFN-β.

B-chain Core 6 Design

A similar calculation similar to that for the A-chain Core 6 design was performed for the B-chain.

The PDA calculation resulted in the following ground state sequence (SEQ ID NO:23):

```
  1   6  10  13  14  17  18  21  38  50  55  56
Met Leu Gln Ser Asn Thr Gln Leu Phe Phe Ala Leu 58  59  61  62  63  66  69  70  72  74  76  77
Thr Ile Glu Met Leu Ile Ile Phe Gln Ser Ser Thr 81  84  87  90  91  94  95  98 102 114 115 118
Glu Ile Leu Asn Ile Gln Ile Leu Leu Leu Lys Glu 122 125 126 129 130 132 133 136 138 139 142 143
Leu Tyr Tyr Ile Leu Tyr Leu Lys Tyr Ser Ala Trp 144 146 147 150 151 153 154 157 159 160 161 163
Thr Val Arg Ile Leu Asn Phe Ile Arg Leu Glu Tyr

164
Leu
```

This sequence shows 7 mutations from the wild type sequence, C17T, A56L, V84I, V91I, G114L, S118E, and T161E (see FIG. 15B) (SEQ ID NO:23).

Using Monte Carlo technique a list of low energy sequences was generated. The analysis of the lowest 1000 protein sequences generated by Monte Carlo leads to the mutation pattern shown in FIG. 15A. Thus, any protein sequence showing mutations at the positions according to FIG. 15A will potentially generate a more stable and active IbA. In particular those protein sequences found among the list of the lowest 101 MC generated sequences (data not shown) have a high potential to result in a more stable and active IbA. A preferred IbA sequence is shown in FIG. 15B (SEQ ID NO:23). A DNA library can be generated to mirror the probability table of FIG. 15A that comprises at least one sequence that is more stable and/or active than wild type IFN-β.

B-chain Core 7 Design

A similar calculation similar to that of the B-chain Core 6 design was performed. Now Gly 114 is treated as a wild type residue.

The PDA calculation resulted in the following ground state sequence (SEQ ID NO:24):

```
  1   6  10  13  14  17  18  21  38  50  55  56
Met Leu Gln Ser Asn Thr Gln Leu Phe Phe Ala Leu 58  59  61  62  63  66  69  70  72  74  76  77
Thr Ile Glu Met Leu Ile Ile Phe Gln Ser Ser Thr 81  84  87  90  91  94  95  98 102 114 115 118
Glu Ile Leu Asn Ile Gln Ile Leu Leu Gly Lys Glu 122 125 126 129 130 132 133 136 138 139 142 143
```

-continued

Leu Tyr Tyr Ile Leu Tyr Leu Lys Tyr Ser Ala Trp 144 146 147 150 151 153 154 157 159 160 161 163
Thr Val Arg Ile Leu Asn Phe Ile Arg Leu Glu Tyr

164
Leu

This sequence shows 6 mutations from the wild type sequence, C17T, A56L, V84I, V91I, S118E, and T161E (see FIG. 16B) (SEQ ID NO:24). With the exception of position 114, now remaining glycine, the ground state sequence is identical to that of Core 6 for the B-chain.

Using Monte Carlo technique a list of low energy sequences was generated. The analysis of the lowest 1000 protein sequences generated by Monte Carlo leads to the mutation pattern shown in FIG. 16A. Thus, any protein sequence showing mutations at the positions according to FIG. 16A will potentially generate a more stable and active IbA. In particular those protein sequences found among the list of the lowest 101 MC generated sequences (data not shown) have a high potential to result in a more stable and active IbA. A preferred IbA sequence is shown in FIG. 16B (SEQ ID NO:24). A DNA library can be generated to mirror the probability table of FIG. 16A that comprises at least one sequence that is more stable and/or active than wild type IFN-β.

I claim:

1. A non-naturally occurring interferon-beta activity (IbA) protein comprising at least fifteen amino acid substitutions as compared to human IFN-β protein (SEQ ID NO: 1), wherein said substitutions are selected from amino acid residues at positions 6, 13, 17, 21, 56, 59, 61, 62, 63, 66, 69, 84, 87, 91, 98, 102, 114, 118, 122, 129, 146, 150, 154, 157, 160, and 161, wherein said protein exhibits at least 50% of the biological activity of human IFN-β protein.

2. The non-naturally occurring IbA protein according to claim 1, wherein said amino acid substitutions are selected from positions 13, 17, 56, 63, 69, 84, 87, 91, 98, 114, 118, 122, 146, 157, and 161.

3. The non-naturally occurring IbA protein according to claim 2, wherein said substitutions are selected from the group of substitutions consisting of S13F, S13Y, S13E, S13A, S13L, C17D, C17A, C17T, A56L, L63F, I69V, V84I, V91I, L98F, G114F, G114L, S118L, S118E, S118A, S118V, S118C, L122I, L122F, L122V, V146I, I157L, T161A, T161E, and T161C.

4. The non-naturally occurring IbA protein according to claim 1 comprising substitutions at positions 13, 17, 69, 84, 87, 91, 98, 118, 122, 146, 157, and 161.

5. The non-naturally occurring IbA protein according to claim 4, wherein said substitutions are selected from the group of substitutions consisting of S13F, S13Y, S13E, S13A, C17D, I69V, V84I, L87F, V91I, L98F, S118A, S118V, S118C, L122I, L122F, I157L, T161A, and T161C.

6. The non-naturally occurring IbA protein according to claim 1 comprising substitutions at positions 13, 17, 56, 63, 84, 87, 91, 114, 118, 122, and 161.

7. The non-naturally occurring IbA protein according to claim 6, wherein said substitutions are selected from the group of substitutions consisting of S13E, S13L, C17A, C17T, A56L, L63F, V84I, L87F, V91I, G114F, G114L, S118L, S118E, L122I, L122F, T161A, and T161E.

8. A pharmaceutical composition comprising an IbA protein according to claim 1 and a pharmaceutical carrier.

9. A non-naturally occurring protein according to claim 1 wherein said biological activity is the ability to bind to an IFN receptor.

10. A non-naturally occurring protein according to claim 1 wherein said biological activity is the ability to inhibit cell proliferation.

11. A non-naturally occurring protein according to claim 1 wherein said biological activity is the ability to inhibit viral infections.

12. A recombinant nucleic acid encoding the non-naturally occurring IbA protein of claim 1.

13. An expression vector comprising the recombinant nucleic acid of claim 12.

14. A host cell comprising the recombinant nucleic acid of claim 12.

15. A host cell comprising the expression vector of claim 13.

16. A method of producing a non-naturally occurring IbA protein comprising culturing the host cell of claim 15 under conditions suitable for expression of said nucleic acid.

17. The method according to claim 16 further comprising recovering said IbA protein.

* * * * *

SEQUENCE LISTING

<160> NUMBER OF SEQ ID NOS: 24

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 757
<212> TYPE: DNA
<213> ORGANISM: Homo sapiens

<400> SEQUENCE: 2
atgaccaaca agtgtctcct ccaaattgct ctcctgttgt gcttctccac tacagctctt      60
tccatgagct acaacttgct tggattccta caaagaagca gcaattttca gtgtcagaag     120
ctcctgtggc aattgaatgg gaggcttgaa tattgcctca aggacaggat gaactttgac     180

```
atccctgagg agattaagca gctgcagcag ttccagaagg aggacgccgc attgaccatc    240
tatgagatgc tccagaacat ctttgctatt ttcagacaag attcatctag cactggctgg    300
aatgagacta ttgttgagaa cctcctggct aatgtctatc atcagataaa ccatctgaag    360
acagtcctgg aagaaaaact ggagaaagaa gattttacca ggggaaaact catgagcagt    420
ctgcacctga aaagatatta tgggaggatt ctgcattacc tgaaggccaa ggagtacagt    480
cactgtgcct ggaccatagt cagagtggaa atcctaagga acttttactt cattaacaga    540
cttacaggtt acctccgaaa ctgaagatct cctagcctgt ccctctggga ctggacaatt    600
gcttcaagca ttcttcaacc agcagatgct gtttaagtga ctgatggcta atgtactgca    660
aatgaaagga cactagaaga ttttgaaatt tttattaaat tatgagttat ttttatttat    720
ttaaatttta ttttggaaaa taaattattt ttggtgc                             757
```

<210> SEQ ID NO 3
<211> LENGTH: 21
<212> TYPE: PRT
<213> ORGANISM: Homo sapiens

<400> SEQUENCE: 3

Met Thr Asn Lys Cys Leu Leu Gln Ile Ala Leu Leu Leu Cys Phe Ser
1               5                   10                  15

Thr Thr Ala Leu Ser
        20

<210> SEQ ID NO 4
<211> LENGTH: 166
<212> TYPE: PRT
<213> ORGANISM: Artificial Sequence
<220> FEATURE:
<223> OTHER INFORMATION: synthetic

<400> SEQUENCE: 4

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Phe Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
            165

<210> SEQ ID NO 5

```
<211> LENGTH: 166
<212> TYPE: PRT
<213> ORGANISM: Artificial Sequence
<220> FEATURE:
<223> OTHER INFORMATION: synthetic

<400> SEQUENCE: 5

Met Ser Tyr Asn Leu Leu Gly Phe Leu Gln Arg Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

Arg Gly Lys Leu Met Ser Ser Leu His Ile Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Leu Asn Arg Leu
145                 150                 155                 160

Thr Gly Tyr Leu Arg Asn
                165

<210> SEQ ID NO 6
<211> LENGTH: 166
<212> TYPE: PRT
<213> ORGANISM: Artificial Sequence
<220> FEATURE:
<223> OTHER INFORMATION: synthetic

<400> SEQUENCE: 6

Met Ser Tyr Asn Leu Leu Gly Phe Leu Gln Arg Ser Phe Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Val Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

Arg Gly Lys Leu Met Ala Ser Leu His Ile Lys Arg Tyr Tyr Gly Arg
        115                 120                 125

Ile Leu His Tyr Leu Lys Ala Lys Glu Tyr Ser His Cys Ala Trp Thr
130                 135                 140

Ile Ile Arg Val Glu Ile Leu Arg Asn Phe Tyr Phe Leu Asn Arg Leu
```

145             150             155             160

Ala Gly Tyr Leu Arg Asn
                165

<210> SEQ ID NO 7
<211> LENGTH: 166
<212> TYPE: PRT
<213> ORGANISM: Artificial Sequence
<220> FEATURE:
<223> OTHER INFORMATION: synthetic

<400> SEQUENCE: 7

Met Ser Tyr Asn Leu Leu Gly Phe Leu Gln Arg Ser Tyr Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Val Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

Arg Gly Lys Leu Met Val Ser Leu His Val Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Ile Arg Val Glu Ile Leu Arg Asn Phe Tyr Phe Leu Asn Arg Leu
145                 150                 155                 160

Ala Gly Tyr Leu Arg Asn
                165

<210> SEQ ID NO 8
<211> LENGTH: 166
<212> TYPE: PRT
<213> ORGANISM: Artificial Sequence
<220> FEATURE:
<223> OTHER INFORMATION: synthetic

<400> SEQUENCE: 8

Met Ser Tyr Asn Leu Leu Gly Phe Leu Gln Arg Ser Phe Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

```
Arg Gly Lys Leu Met Ala Ser Leu His Ile Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Leu Asn Arg Leu
145                 150                 155                 160

Ala Gly Tyr Leu Arg Asn
                165

<210> SEQ ID NO 9
<211> LENGTH: 166
<212> TYPE: PRT
<213> ORGANISM: Artificial Sequence
<220> FEATURE:
<223> OTHER INFORMATION: synthetic

<400> SEQUENCE: 9

Met Ser Tyr Asn Leu Leu Gly Phe Leu Gln Arg Ser Phe Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Val Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

Arg Gly Lys Leu Met Ala Ser Leu His Ile Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Ile Arg Val Glu Ile Leu Arg Asn Phe Tyr Phe Leu Asn Arg Leu
145                 150                 155                 160

Ala Gly Tyr Leu Arg Asn
                165

<210> SEQ ID NO 10
<211> LENGTH: 166
<212> TYPE: PRT
<213> ORGANISM: Artificial Sequence
<220> FEATURE:
<223> OTHER INFORMATION: synthetic

<400> SEQUENCE: 10

Met Ser Tyr Asn Leu Leu Gly Phe Leu Gln Arg Ser Tyr Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Val Phe Arg Gln Asp Ser Ser Ser Thr Gly Trp Asn
65                  70                  75                  80
```

```
Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

Arg Gly Lys Leu Met Val Ser Leu His Val Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Ile Arg Val Glu Ile Leu Arg Asn Phe Tyr Phe Leu Asn Arg Leu
145                 150                 155                 160

Ala Gly Tyr Leu Arg Asn
                165

<210> SEQ ID NO 11
<211> LENGTH: 166
<212> TYPE: PRT
<213> ORGANISM: Artificial Sequence
<220> FEATURE:
<223> OTHER INFORMATION: synthetic

<400> SEQUENCE: 11

Met Ser Tyr Asn Leu Leu Gly Phe Leu Gln Arg Ser Phe Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Phe Lys Thr Val Leu Glu Glu Lys Leu Glu Lys Glu Asp Phe Thr
            100                 105                 110

Arg Gly Lys Leu Met Ala Ser Leu His Ile Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Leu Asn Arg Leu
145                 150                 155                 160

Ala Gly Tyr Leu Arg Asn
                165

<210> SEQ ID NO 12
<211> LENGTH: 166
<212> TYPE: PRT
<213> ORGANISM: Artificial Sequence
<220> FEATURE:
<223> OTHER INFORMATION: synthetic

<400> SEQUENCE: 12

Met Ser Tyr Asn Leu Leu Gly Phe Leu Gln Arg Ser Glu Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
```

```
                    35                  40                  45
Gln Phe Gln Lys Glu Asp Ala Ala Leu Thr Ile Tyr Glu Met Leu Gln
            50                  55                  60

Asn Ile Phe Ala Ile Phe Arg Gln Asp Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Cys Ser Leu His Leu Lys Arg Tyr Tyr Gly Arg
                115                 120                 125

Ile Leu His Tyr Leu Lys Ala Lys Glu Tyr Ser His Cys Ala Trp Thr
                130                 135                 140

Ile Ile Arg Val Glu Ile Leu Arg Asn Phe Tyr Phe Ile Asn Arg Leu
145                 150                 155                 160

Cys Gly Tyr Leu Arg Asn
                165

<210> SEQ ID NO 13
<211> LENGTH: 166
<212> TYPE: PRT
<213> ORGANISM: Artificial Sequence
<220> FEATURE:
<223> OTHER INFORMATION: synthetic

<400> SEQUENCE: 13

Met Ser Tyr Asn Leu Leu Gly Phe Leu Gln Arg Ser Ala Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
                35                  40                  45

Gln Phe Gln Lys Glu Asp Ala Ala Leu Thr Ile Tyr Glu Met Leu Gln
            50                  55                  60

Asn Ile Phe Ala Ile Phe Arg Gln Asp Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Cys Ser Leu His Leu Lys Arg Tyr Tyr Gly Arg
                115                 120                 125

Ile Leu His Tyr Leu Lys Ala Lys Glu Tyr Ser His Cys Ala Trp Thr
                130                 135                 140

Ile Ile Arg Val Glu Ile Leu Arg Asn Phe Tyr Phe Leu Asn Arg Leu
145                 150                 155                 160

Cys Gly Tyr Leu Arg Asn
                165

<210> SEQ ID NO 14
<211> LENGTH: 166
<212> TYPE: PRT
<213> ORGANISM: Artificial Sequence
<220> FEATURE:
<223> OTHER INFORMATION: synthetic

<400> SEQUENCE: 14
```

Met Ser Tyr Asn Leu Leu Gly Phe Leu Gln Arg Ser Glu Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Cys Ser Leu His Leu Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Val Arg Val Glu Ile Leu Arg Asn Phe Tyr Phe Ile Asn Arg Leu
145                 150                 155                 160

Cys Gly Tyr Leu Arg Asn
                165

<210> SEQ ID NO 15
<211> LENGTH: 166
<212> TYPE: PRT
<213> ORGANISM: Artificial Sequence
<220> FEATURE:
<223> OTHER INFORMATION: synthetic

<400> SEQUENCE: 15

Met Ser Tyr Asn Leu Leu Gly Phe Leu Gln Arg Ser Glu Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Val Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ala Ser Leu His Ile Lys Arg Tyr Tyr Gly Arg
            115                 120                 125

Ile Leu His Tyr Leu Lys Ala Lys Glu Tyr Ser His Cys Ala Trp Thr
            130                 135                 140

Ile Ile Arg Val Glu Ile Leu Arg Asn Phe Tyr Phe Leu Asn Arg Leu
145                 150                 155                 160

Ala Gly Tyr Leu Arg Asn
                165

<210> SEQ ID NO 16
<211> LENGTH: 166

-continued

```
<212> TYPE: PRT
<213> ORGANISM: Artificial Sequence
<220> FEATURE:
<223> OTHER INFORMATION: synthetic

<400> SEQUENCE: 16

Met Ser Tyr Asn Leu Leu Gly Phe Leu Gln Arg Ser Glu Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ala Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Ile Arg Val Glu Ile Leu Arg Asn Phe Tyr Phe Leu Asn Arg Leu
145                 150                 155                 160

Thr Gly Tyr Leu Arg Asn
                165

<210> SEQ ID NO 17
<211> LENGTH: 166
<212> TYPE: PRT
<213> ORGANISM: Artificial Sequence
<220> FEATURE:
<223> OTHER INFORMATION: synthetic

<400> SEQUENCE: 17

Met Ser Tyr Asn Leu Leu Gly Phe Leu Gln Arg Ser Glu Asn Phe Gln
1               5                   10                  15

Asp Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ala Ser Leu His Ile Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Leu Asn Arg Leu
145                 150                 155                 160
```

Ala Gly Tyr Leu Arg Asn
            165

<210> SEQ ID NO 18
<211> LENGTH: 166
<212> TYPE: PRT
<213> ORGANISM: Artificial Sequence
<220> FEATURE:
<223> OTHER INFORMATION: synthetic

<400> SEQUENCE: 18

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Phe Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
            165

<210> SEQ ID NO 19
<211> LENGTH: 166
<212> TYPE: PRT
<213> ORGANISM: Artificial Sequence
<220> FEATURE:
<223> OTHER INFORMATION: synthetic

<400> SEQUENCE: 19

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Leu Leu Thr Ile Tyr Glu Met Phe Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Phe Leu Ala Asn Ile Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Phe Lys Arg Tyr Tyr Gly Arg

-continued

```
                115                 120                 125
Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 20
<211> LENGTH: 166
<212> TYPE: PRT
<213> ORGANISM: Artificial Sequence
<220> FEATURE:
<223> OTHER INFORMATION: synthetic

<400> SEQUENCE: 20

Met Ser Tyr Asn Leu Leu Gly Phe Leu Gln Arg Ser Leu Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Leu Leu Thr Ile Tyr Glu Met Leu Gln
    50                  55                  60

Asn Ile Phe Ala Ile Phe Arg Gln Asp Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
            100                 105                 110

Arg Phe Lys Leu Met Leu Ser Leu His Ile Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Ala Gly Tyr Leu Arg Asn
                165

<210> SEQ ID NO 21
<211> LENGTH: 166
<212> TYPE: PRT
<213> ORGANISM: Artificial Sequence
<220> FEATURE:
<223> OTHER INFORMATION: synthetic

<400> SEQUENCE: 21

Met Ser Tyr Asn Leu Leu Gly Phe Leu Gln Arg Ser Leu Asn Phe Gln
1               5                   10                  15

Ala Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Leu Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80
```

Glu Thr Ile Ile Glu Asn Phe Leu Ala Asn Leu Tyr His Gln Ile Asn
                85                  90                  95

His Leu Lys Thr Val Leu Glu Glu Lys Leu Glu Lys Glu Asp Phe Thr
               100                 105                 110

Arg Phe Lys Leu Met Leu Ser Leu His Ile Lys Arg Tyr Tyr Gly Arg
           115                 120                 125

Ile Leu His Tyr Leu Lys Ala Lys Glu Tyr Ser His Cys Ala Trp Thr
       130                 135                 140

Ile Val Arg Val Glu Ile Leu Arg Asn Phe Tyr Phe Ile Asn Arg Leu
145                 150                 155                 160

Glu Gly Tyr Leu Arg Asn
                165

<210> SEQ ID NO 22
<211> LENGTH: 166
<212> TYPE: PRT
<213> ORGANISM: Artificial Sequence
<220> FEATURE:
<223> OTHER INFORMATION: synthetic

<400> SEQUENCE: 22

Met Ser Tyr Asn Leu Leu Gly Phe Leu Gln Arg Ser Glu Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Leu Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Ile Glu Asn Leu Leu Ala Asn Ile Tyr His Gln Ile Asn
                85                  90                  95

His Leu Lys Thr Val Leu Glu Glu Lys Leu Glu Lys Glu Asp Phe Thr
               100                 105                 110

Arg Leu Lys Leu Met Glu Ser Leu His Leu Lys Arg Tyr Tyr Gly Arg
           115                 120                 125

Ile Leu His Tyr Leu Lys Ala Lys Glu Tyr Ser His Cys Ala Trp Thr
       130                 135                 140

Ile Val Arg Val Glu Ile Leu Arg Asn Phe Tyr Phe Ile Asn Arg Leu
145                 150                 155                 160

Glu Gly Tyr Leu Arg Asn
                165

<210> SEQ ID NO 23
<211> LENGTH: 166
<212> TYPE: PRT
<213> ORGANISM: Artificial Sequence
<220> FEATURE:
<223> OTHER INFORMATION: synthetic

<400> SEQUENCE: 23

Met Ser Tyr Asn Leu Leu Gly Phe Leu Gln Arg Ser Ser Asn Phe Gln
1               5                   10                  15

Thr Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

```
Gln Phe Gln Lys Glu Asp Ala Leu Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Ile Glu Asn Leu Leu Ala Asn Ile Tyr His Gln Ile Asn
                 85                  90                  95

His Leu Lys Thr Val Leu Glu Glu Lys Leu Glu Lys Glu Asp Phe Thr
             100                 105                 110

Arg Leu Lys Leu Met Glu Ser Leu His Leu Lys Arg Tyr Tyr Gly Arg
         115                 120                 125

Ile Leu His Tyr Leu Lys Ala Lys Glu Tyr Ser His Cys Ala Trp Thr
         130                 135                 140

Ile Val Arg Val Glu Ile Leu Arg Asn Phe Tyr Phe Ile Asn Arg Leu
145                 150                 155                 160

Glu Gly Tyr Leu Arg Asn
                165

<210> SEQ ID NO 24
<211> LENGTH: 166
<212> TYPE: PRT
<213> ORGANISM: Artificial Sequence
<220> FEATURE:
<223> OTHER INFORMATION: synthetic

<400> SEQUENCE: 24

Met Ser Tyr Asn Leu Leu Gly Phe Leu Gln Arg Ser Ser Asn Phe Gln
 1               5                  10                  15

Thr Gln Lys Leu Leu Trp Gln Leu Asn Gly Arg Leu Glu Tyr Cys Leu
             20                  25                  30

Lys Asp Arg Met Asn Phe Asp Ile Pro Glu Glu Ile Lys Gln Leu Gln
         35                  40                  45

Gln Phe Gln Lys Glu Asp Ala Leu Leu Thr Ile Tyr Glu Met Leu Gln
     50                  55                  60

Asn Ile Phe Ala Ile Phe Arg Gln Asp Ser Ser Ser Thr Gly Trp Asn
 65                  70                  75                  80

Glu Thr Ile Ile Glu Asn Leu Leu Ala Asn Ile Tyr His Gln Ile Asn
                 85                  90                  95

His Leu Lys Thr Val Leu Glu Glu Lys Leu Glu Lys Glu Asp Phe Thr
             100                 105                 110

Arg Gly Lys Leu Met Glu Ser Leu His Leu Lys Arg Tyr Tyr Gly Arg
         115                 120                 125

Ile Leu His Tyr Leu Lys Ala Lys Glu Tyr Ser His Cys Ala Trp Thr
         130                 135                 140

Ile Val Arg Val Glu Ile Leu Arg Asn Phe Tyr Phe Ile Asn Arg Leu
145                 150                 155                 160

Glu Gly Tyr Leu Arg Asn
                165
```